(12) United States Patent
Haselkorn et al.

(10) Patent No.: US 6,399,342 B1
(45) Date of Patent: Jun. 4, 2002

(54) CYANOBACTERIAL AND PLANT ACETYL-COA CARBOXYLASE

(75) Inventors: Robert Haselkorn; Piotr Gornicki, both of Chicago, IL (US)

(73) Assignee: Arch Development Corp., Chicago, IL (US)

( * ) Notice: Subject to any disclaimer, the term of this patent is extended or adjusted under 35 U.S.C. 154(b) by 0 days.

(21) Appl. No.: 09/433,043

(22) Filed: Oct. 25, 1999

Related U.S. Application Data

(62) Division of application No. 08/475,879, filed on Jun. 7, 1995, now Pat. No. 5,972,644, which is a division of application No. 07/956,700, filed on Oct. 2, 1992, now Pat. No. 5,539,092.

(51) Int. Cl.$^7$ ............................. C12P 21/06; C12N 1/20; C12N 15/00; C12N 5/00; C07H 21/04

(52) U.S. Cl. ............... 435/183; 435/252.33; 435/320.1; 435/69.1; 435/325; 435/419; 536/23.1; 536/23.7; 530/350

(58) Field of Search ................................ 435/69.1, 183, 435/252.33, 320.1, 325, 419; 536/23.1, 23.7; 530/350

(56) References Cited

U.S. PATENT DOCUMENTS

| | | |
|---|---|---|
| 4,535,060 A | 8/1985 | Comai ..................... 435/172.3 |
| 4,757,011 A | 7/1988 | Chaleff et al. ............ 435/172.1 |
| 4,769,061 A | 9/1988 | Comai .......................... 71/86 |
| 4,940,835 A | 7/1990 | Shah et al. ................. 800/205 |
| 4,971,908 A | 11/1990 | Kishore et al. ........... 435/172.1 |

FOREIGN PATENT DOCUMENTS

| | | |
|---|---|---|
| CA | 2048040 | 1/1992 |
| EP | 0 469 810 A1 | 2/1992 |
| WO | WO 93/11243 | 6/1993 |

OTHER PUBLICATIONS

Aebersold et. al, Internal amino acid sequence analysis of proteins separated by one or two–dimensional gel electrophoresis after in situ protease, *Proc. Natl. Acad. Sci. USA* 84:6970–6974, 1987.

Al–Feel et. al, Cloning of the yeast FAS3 gene and primary structure of yeast acetyl–CoA carboxylase, *Proc. Natl. Acad. Sci. USA*, 89:4534–4538, 1992.

Alix, Laboratory Methods; A Rapid Procedure for Cloning Genes from λ Libraries by Complementation of *E. coli* Defective Mutants: Application to the fabE Region of the *E. coli* Chromosome, *DNA* 8:(10)779–789, 1989.

Bai, et. al, Analysis of the biotin–binding site on acetyl–CoA carboxylase from rat, *Eur. J. Biochem.* 182:239–245, 1989.

Buhler et. al, Improved Purification and Further Characterization of Acetyl–CoA Carboxylase from Cultured Cells of Parsley (*Petroselinum hortense*) *Eur. J. Biochem.* 133:335–339, 1983.

Craig et. al, Genetic engineering of micro–algae, Micro–Algal Biotechnology Cambridge University Press, 16:415–455, 1988.

Eichholtz et. al, Expression of Mouse Dihydrofolate Reductase Gene Confers Methotrexate Resistance in Transgenic Petunia Plants, *Somatic Cell and Molecular Genetics*, 13:(1)67–76, 1987.

Evenson et. al, Purification and Characterization of Acetyl–CoA Carboxylase from Diclofop–Resistant and Susceptible Italian Ryegrass (*Lolium Multiflorum*), *Plant Physiol*, 99(1 Suppl):59, Abstract #351, 1992.

Golden, Genetic Engineering of the cyanobacterial Chromosome, *J. Bacteriol*, 165:(964)215–231, 1986.

Guchhait et.al, Acetyl Coenzyme A Carboxylase System of *Escherichia coli, J. Biol. Chem.* 249:(20)6633–6645, 1974.

Harwood, Fatty Acid Metabolism, *Ann. Rev. Plant Physiol. Plant Mol. Biol.*, 39:101–138, 1988.

Harwood, Medium and Long–Chain Fatty Acid Synthesis in, The Metabolism, Structure, and Function of Plant Lipids, Edited by: Stumpf et. al, 465–472.

Haymerle et.al, Efficient construction of cDNA libraries in plasmid expression vectors using an adaptor strategy, *Nucleic Acids Research*, 14:(21)8615–8624, 1986.

Jaye et. al, Isolation of a human anti–haemophilic factor IX cDNA clone using a unique 52–base synthetic oligonucleotide probe deduced from the amino acid sequence of bovine factor IX, *Nucleic Acids Research* 11:(8)2325–2335, 1983.

Knowles, The Mechanism of Biotin–Dependent Enzymes, *Annu. Rev. Biochem.* 58:195–221, 1989.

Kondo et. al, Acetyl–CoA carboxylase from *Escherichia coli*: Gene organization and nucleotide sequence of the biotin carboxylase subunit, *Proc. Natl. Acad. Sci. USA* 88:9730–9733, 1991.

Lamppa et. al, Structure and Developmental Regulation of a Wheat Gene Encoding the Major Chlorophyll a/b–BInding Polypeptide, *Mole. Cell. Bio.*, 5:(6)1370–1378, 1985.

Li et.al, The Gene Encoding the Biotin Carboxylase Subunit of *Escherichia coli* Acetyl–CoA Carboxylase, *J. Biol. Chem.*, 267:(2)855–863, 1992.

(List continued on next page.)

Primary Examiner—Tekchand Saidha
(74) Attorney, Agent, or Firm—Fulbright & Jaworski, LLP

(57) ABSTRACT

The present invention provides isolated and purified polynucleotides that encode plant and cyanobacterial polypeptides that participate in the carboxylation of acetyl-CoA. Isolated cyanobacterial and plant polypeptides that catalyze acetyl-CoA carboxylation are also provided. Processes for altering acetyl-CoA carboxylation, increasing herbicide resistance of plants and identifying herbicide resistant variants of acetyl-CoA carboxylase are also provided.

13 Claims, 18 Drawing Sheets

OTHER PUBLICATIONS

Lichtenthaler, Mode of Action of Herbicides Affecting Acety;–CoA Carboxylase and Fatty Acid Biosynthesis, *Z. Naturforsch*, 45c:521–528, 1990.

Livine et. al, Acetyl–Coenzyme A Carboxylase from the Marine Prymnesiophyte *Isochrysis galbana, Plant Cell Physiol*, 31:(6)851–858, 1990.

Lopez–Casillas et. al, Structure of the coding sequence and primary amino acid sequence of acetyl–coenzyme A carboxylase, *Proc. Natl. Acad. Sci. USA*, 85:5784–5788, 1988.

Lopez–Casillas et. al, Heterogeneity at the 5' End of Rat Acetyl–coenzyme A Carboxylase mRNA, *J. Biological Chem.*, 264:(13)7176–7184, 1989.

Luo et. al, Structural features of the acetyl–CoA carboxylase gene: Mechanisms for the generation of mRNAs with 5' end heterogeneity, *Proc. Natl. Acad. Sci. USA*, 86:4042–4046, 1989.

Muramatsu et. al, Nucleotide sequence of the fabE gene and flanking regions containing a bent DNA sequence of *Escherichia coli, Nucleic Acids Research*, 17:(10)3982, 1989.

Palosarri et. al, Comparison of Acetyl–Coenzyme A Carboxylase From Graminicide–Tolerant and Susceptible Maize Lines, *Plant Physiol.*, 99(1Suppl):59, Abstract #352, 1992.

Pecker et. al, A single polypeptide catalyzing the conversion of phytoene to $\zeta$–carotene is transcriptionally regulated during tomato fruit ripening, *Proc. Natl. Acad. Sci. USA*, 89:4962–4966, 1992.

Post–Beittenmiller et. al, In Vivo Pools of Free and Acylated Acyl Carrier Proteins in Spinach, *J. Biol. Chem.*, 266:(3)1858–1865, 1991.

Roessler et. al, Characterization of the Gene for Acetyl–CoA Carboxylase From the Alga *Cyclotella Cryptica, Plant Physiol.*, 99(1 Suppl):19 Abstract #113, 1992.

Roessler et. al, Purification and Characterization of Acetyl-CoA Carboxylase from the Diatom *Cyclotella cryptica, Plant Physiol.*, 92:73–78, 1990.

Samols et. al, Evolutionary Conservation among Biotin Enzymes, *J. Biol. Chem.*, 263:6461–6464, 1988.

Slabas et. al, Rapid Purification of a High Molecular Weight Subunit Polypeptide Form of Rape Seed Acetyl CoA Carboxylase, *Plant Science*, 39:177–182, 1985.

Sedlak, Iowa State Scientist Clone A Key Plant Oil Production Gene, *Gene Engineering News*, May 1991.

Takai et. al, Primary Structure of Chicken Liver Acetyl–CoA Carboxylase Deduced from cDNA Sequence, *J. Biol. Chem.*, 263:(6)2651–2657, 1988.

Vasil et. al, Herbicide Resistant Fertile Transgenic Wheat Plants Obtained By Microprojectile Bombardment of Regenerable Embryogenic Callus, *Bio/Technology*, 10:667–674, 1992.

Wurtele et. al, Plants Contain Multiple Biotin Enzymes: Discovery of 3–Methylcrotonyl–CoA Carboxylase, Propionyl–CoA Carboxylase and Pyruvate Carboxylase in the Plant Kingdom,*Archives of Biochemistry and Biophysics*, 278:(1)179–186, 1990.

Slabas et al., "The Biochemistry and Molecular Biology of Plant Lipid Biosynthesis," *Plant Molecular Biology*, 19:169–191, 1992.

Egin–Buehler et al., "Comparison of Acetyl Coenzyme A Carboxylases (ED 6.4.1.2) From Parsley (*Petroselinum Hortense*) Cell Cultures and Wheat Germ," *Arch Biochem Biophys.*, 203(1):90–100, 1980 (Abstract).

Egli et al., "A 223 kDa Subunit of Acetyl–CoA Carboxylase is Encoded by the Accl Gene," *Maize Genetics Cooperation Newsletter*, 66:94–95, 1992.

Egli et al., "Purification of Maize Leaf Acetyl–CoA Carboxylase," *Maize Genetics Cooperation Newsletter*, 65:95, 1991.

Egli et al., "Purification and Characterization of Maize Acetyl–CoA Carboxylase," *Plant Physiology*, 96(1):92(581), 1991.

Gornicki et al., "Genes for Two Subunits of Acetyl Coenzyme A Carboxylase of Anabaena sp. Strain PCC 7120: Biotin Carboxylase and Biotin Carboxyl Carrier Protein," *Journal of Bacteriology*, 175(16):5268–5272, 1993.

Nicolau et al., "Use of Streptavidin to Detect Biotin–Containing Proteins in Plants," *Anal Biochem.*, 149(2):448–453, 1985.

Alban et al., "Purification and characterization of 3–methylcrotonyl–coenzyme A carboxylase from higher plant mitochondria," *Plant. Physiol.*, 102:957–965, 1993.

Best, E.A., and Knauf, V.C., "Organization and nucleotide sequence of the genes encoding the biotin carboxyl carrier protein and biotin cargboxylase protein of *Pseudomonas aeruginosa* acetyl coenzyme A carboxylase," *J. Bacteriol.*, 175:6881–6889, 1993.

Bettey et al., "Purification and characterization of acetylcoA carboxylase from developing pea embryos," *J. Plant. Physiol.*, 140:513–520, 1992.

Browner et al., "Sequence analysis, biogenesis and mitochonoriald import of the alpha–subunit of rat liver propionyl–CoA carboxylase," *J. Biol. Chem.*, 264:12680–12685.

Chen et al., Purification and characterization of 3–methylocrotonyl–CoA carboxylase from somatic embryos of *Dacuscarota.*, *Arch. Biochem. Biophys.*, 305:103–109, 1993.

Chirala, S.S., "Coordinated regulation and inositol–mediated and fatty acid–mediated repression of fatty acid synthase genes in *Saccharomyces cerevisiae*,"*proc. Natl. Acad. Sci. USA*, 89:10232–10236, 1992.

Egin–Buhler, B. and Ebel, J., "Comparison of acetyl–CoA carboxylase from parsley cell culture and from wheat germ," *Eur. J. Biochem.*, 133:335–339, 1983.

Egli et al., "Characterization of maize acetyl–coenzyme A carboxylase," *Plant. Physiol.*, 101:499–506, 1993.

Fall, R.R., "Analysis of microbiol biotin proteins," *Meth. Enzymol.*, 62:390–398, 1979.

FIG. 1A

```
ATGCTGGCGTTATATAGAAAAATTTATTGAACGTCCGCGCCACATGAATTTCAAATTTTGGCTGATAATTACGGCAATGTGATTCACT   1980
 A  G  V  Y  I  E  K  F  I  E  R  P  R  H  I  E  F  Q  I  L  A  D  N  Y  G  N  V  I  H  L
TGGGTGAGAGGGATTGCTCAATTCAGCTCGTAACCAAAAGTTACTAGAGAGAAGCCCCAGCCCTTGGACTCAGACCTAAGGGAAA    2070
 G  E  R  D  C  S  I  Q  R  R  N  Q  K  L  E  E  A  P  S  A  L  D  S  D  L  R  E  K
AAATGGGACAAGGCGGGTGAAAGCGGCTCAGTTTATCAATTACGCCGGGGCAGGTACTATCGAGTTTTGCTAGATAGATCCGGTCAGT  2160
 M  G  Q  A  A  V  K  A  A  Q  F  I  N  Y  A  G  T  I  E  F  L  L  D  R  S  G  Q  F
TTTACTTATGGAGATGAACACCCGGATTCAAGTAGAACATCCGTAACTGAGAGTTACTGGAGTGGATTTATTGGTTGAGCAAATCA    2250
 Y  F  M  E  M  N  T  R  I  Q  V  E  H  P  V  T  E  M  V  T  G  V  D  L  L  V  E  Q  I  R
GAATTGCCCAAGGGAAAGACTAGAACTAAGCAAGTAGTTTACGCGTCATGCGATCGAATGTCGCATCAATGCCGAAGACC        2340
 I  A  Q  G  E  R  L  R  L  T  Q  D  Q  V  L  R  G  H  A  I  E  C  R  I  N  A  E  D  P
CAGACCACGAGATTCCGCCCAGCACCCGGACGCATAGGGGTTATCTTCCCCCTGGCGTGCCTGGATTGACTCCACGTTACA        2430
 Q  T  T  R  D  F  R  P  A  P  G  R  I  S  G  Y  L  P  P  G  G  P  G  V  R  I  D  S  H  V  Y  T
CGGATTACCAAATTCCGCCTACTACGATTCCTTAATTGGTAAATTGATCGTTGGGCCCTGATCGCTACTGCTATTAACCGCATGA    2520
 D  Y  Q  I  P  P  Y  D  S  L  I  G  K  L  I  V  W  G  P  D  R  A  T  A  I  N  R  M  K
AACGCGCCCTCAGGGAATGCGCCATCACTGGATTACTACAACCATTGGGTTCATCAAAGAATTATGGAAAATCCCCAATTTTACAAG  2610
 R  A  L  R  E  C  A  I  T  G  L  P  T  T  I  G  F  H  Q  R  I  M  E  N  P  Q  F  L  Q  G
GTAATGTGTCTACTAGTTTTGTGCAGGAGATGAATAAATAGGGTAATGGGTAATAGAGTTTCAATCACCAATTACC           2700
 V  N  V  S  S  T  S  F  V  Q  E  M  N  K  *    *  W  V  M  G  N  R  V  S  I  T  N  Y  Q
AATTCCCTAACTCATCCGTGCCAACATCGTCAGTAATCCTTGCTGGCCTAGAAGAACTTCTGCAACAGGCTAAAAATACCAACACAC  2790
 F  P  N  S  S  V  P  T  S  S  V  I  L  A  G  L  E  E  L  L  A  T  G  *
AATGGGGGTGATATCAACACCACCTATTGGTGGGATGATTTTCGCAAGGGAATGAGAAATGGTTCAGTCGGCCAAGCAATTAAGTTGAA 2880
GGGCAAACGGTTCAGATTGACTTGCGGATACCAGGTCAGAATGGTCAGAATAAACAGAAATGTCATCACTCCAATACAGGGCCAAG    2970
AATCCAAACGCTCAGGTTAACACCAGTCATCGATCTAAGCTACTATTTGTGAATTTACAAAAAACTGCAAGCAAAGCTGAAAATTTA    3060
AGCTT                                                                                  3065
```

FIG. 1B

```
ATGCGTTTCA ACAAGATCCT GATCGCCAAT CGCGGCGAAA TCGCCCTGCG CATTCTCCGC

ACTTGTCAAG AACTCGGGAT CGGCACGATC GCCGTTCACT CCACTGTGGA TCGCAACGCG

CTCCATGTGC AGTTAGCGGA CGAAGCGGTC TGTATTGGCG AAGCGGCCAG CAGCAAAAGC

TATCTCAATA TCCCCAACAT CATTGCGGCG GCCCTGACCC CTAATGCCAG CGCCATTCAC

CCCGGCTATG GCTTCTTGGC GGAGAATGCC CGCTTTGCAG AAATCTGCGC CGATCACCAT

CTCACCTTTA TTGGCCCCAG CCCCGATTCG ATTCGAGCCA TGGGCGATAA ATCCACCGCT

AAGGAAACAA TGCAGCGGGT CGGCGTTCCG ACGATTCCGG GCAGTGACGG TCTGCTGACG

GATGTTGATT CGGCTGCCAA AGTTGCTGCC GAGATCGGCT ATCCCGTCAT GATCAAAGCG

ACGGCGGGGG GCGGTGGTCG CGGTATGCGG CTGGTGCGTG ACCCTGCAGA TCTGGAAAAA

CTGTTCCTTG CTGCCCAAGG AGAAGCCGAG GCAGCTTTTG GGAATCCAGG ACTGTATCTC

GAAAAATTTA TCGATCGCCC ACGCCACGTT GAATTTCAGA TCTTGGCCGA TGCCTACGGC

AATGTAGTGC ATCTAGGCGA GCGCGATTGC TCCATTCAAC GTCGTCACCA AAAGCTGCTC

GAAGAAGCCC CCAGTCCGGC GCTATCGGCA GACCTGCGGC AGAAAATGGG CGATGCCGCC

GTCAAAGTCG CTCAAGCGAT CGGCTACATC GGTGCCGGCA CCGTGGAGTT TCTGGTCGAT

GCGACCGGCA ACTTCTACTT CATGGAGATG AATACCCGCA TCCAAGTCGA GCATCCAGTC

ACAGAAATGA TTACGGGACT GGACTTGATT GCGGAGCAGA TTCGGATTGC CCAAGGCGAA

GCGCTGCGCT TCCGGCAAGC CGATATTCAA CTGCGCGGCC ATGCGATCGA ATGCCGTATC

AATGCGGAAG ATCCGGAATA CAATTTCCGG CCGAATCCTG GCCGCATTAC AGGCTATTTA

CCGCCCGGCG GCCCCGGCGT TCGTGTCGAT TCCCATGTTT ATACCGACTA CGAAATTCCG

CCCTATTACG ATTCGCTGAT TGGCAAATTG ATTGTCTGGG GTGCAACACG GGAAGAGGCG

ATCGCGCGGA TGCAGCGTGC TCTGCGGGAA TGCGCCATCA CCGGCTTGCC GACGACCCTT

AGTTTCCATC AGCTGATGTT GCAGATGCCT GAGTTCCTGC GCGGGGAACT CTATACCAAC
```

FIG. 2A

TTTGTTGAGC AGGTGATGCT ACCTCGGATC CTCAAGTCCT AG amino acid sequence

MRFNKILIAN RGEIALRILR TCEELGIGTI AVHSTVDRNA LHVQLADEAV CIGEAASSKS

YLNIPNIIAA ALTRNASAIH PGYGFLAENA RFAEICADHH LTFIGPSPDS IRAMGDKSTA

KETMQRVGVP TIPGSDGLLT DVDSAADVAA EIGYPVMIKA TAGGGGRGMR LVREPADLEK

LFLAAQGEAE AAFGNPGLYL EKFIDRPRHV EFQILADAYG NVVELGERDC SIQRRHQKLL

EEAPSPALSA DLRQKMGDAA VKVAQAIGYI GAGTVEFLVD ATGNFYFMEM NTRIQVEHPV

TEMITGLDLI AEQIRIAQGE ALRFRQADIQ LRGHAIECRI NAEDPEYNFR PNPGRITGYL

PPGGPGVRVD SHVYTDYEIP PYYDSLIGKL IVWGATREEA IARMQRALRE CAITGLPTTL

SFHQLMLQMP EFLRGELYTN FVEQVMLPRI LKS

FIG. 2B

```
Wh ACC  ..............................................................       70
Rt ACC  MDEPSPLAKTLELNQHSRFIIGSVSEDNSEDEIS-NLVKLDLEEKEGSLSPASVSSDTLSDLGISALQDG
Ch ACC  MEESSQPAKPLEMNPHSRFIIGSVSEDNSEDETSSLVKLDLLEEKERSLSPVSVCSDSLSDLGLPSAQDG
Yt ACC  ..............................................................MSEESLFESSP
Sy ACC  ..............................................................
An ACC  ..............................................................
Ec ACC  ..............................................................
Hm PCCA ..............................................................
Rt PCCA ..............................................................
Yt PC   ........................................................MPYRERFC

Wh ACC                                                                         140
Rt ACC  LAFHMRSSMSGLHLVKQGRKRKKIDSQRDFTVASPAEFVTRFGGNKVIEKVLIANNGIAABKCMRSIRRW
Ch ACC  LANHMRPSMSGLHLVKQGRDRKKVDQRDFTVASPAEFVTRFGGNRVIEKVLIANNGIAAVKCMRSIRRW
Yt ACC  QKMEYEITNYSERHTELPGHFIGLNTVDKLEESPLRDFVKSHGGHTVISKILIANNGIAAVKEIRSVRKW
Sy ACC                                         MRFNKILIANRGEIALRLRTCEEL
An ACC                                         MKRFKILIANRGEIALRILRACEEM
Ec ACC                                         MLDKIVIANRGEIALRILRACKEL
Hm PCCA MLSAALRTLKHVLYYSRQCLMVSRNLGSVGYDPNEKTFDKILVANRGEIACRVIRTCKKM
Rt PCCA AIRWCRNSGRSSQQLLWTLKRAPVYSQQCLVVSRSLSSVEYEPKEKTFDKILIANRGEIACRVIKTCRKM
Yt PC   MSQRKFAGLRDNFNLLGEK-NKILVANRGEIPIRIFRTAHEL
                                       *  ** *  *
```

FIG. 3A

```
                                                                              210
Wh ACC  ........................SYEMFRNERAIRFVVMVTPEDLKANAEYIKMADHYPVPGGANNNNYANVELILDIAKRIPVQAVWAGWG
Rt ACC  ........................SYEMFRNERAIRFVVMVTPEDLKANAEYIKMADHYPVPGGPNNNNYANVELILDIAKRIPVQAVWAGWG
Ch ACC  ........................AYETFGDDRTVQFVAMATPEDLEANAEYIRMADQYIEVPGGTNNNNYANVDLIVDIAERADVDAVWAGWG
Yt ACC  ........................GIGTIAVHSTVD--RNALHVQLADEAVCIGEAASS------------KSYLNIPNIIAAALTRNASAIHPGTG
Sy ACC  ........................GIATIAVHSTVD--RNALHVQLADEAVCIGEPASA------------KSYLNIPNIIAAALTRNASAIHPGYG
An ACC  ........................GIKTVAVHSSAD--RDLKHVLLADETVCIGPAPSV------------KSYLNIPAIISAAEITGAVAIHPGYG
Ec ACC  ........................GIKTVAIHSDVD--ASSVHVKMADEAVCVGPAPTS------------KSYLNMDAIMEAIKKTRAQAVHPGYG
Hm PCCA ........................GIRTVAIHSDVD--ASSVHVKMADEAVCVGPAPTS------------KSYLNMDAIMEAIKKTGAQAVHPGYG
Rt PCCA ........................SMQTVAIYSHED--RLSTHKQKADEAYVIGEVGQYTPV---------GAYLAIDEIISIAQKHQVDFIHPGYG
Yt PC                                                                                              * *
                                     *                                                  *
                                                                                                    280
Wh ACC  ........................HASENPKLPELL--LKNGIAFMGPPSQAMWALGDKIASSIVAQTAGIPTLPWSGSGSGLRVDWQENDFSKRI
Rt ACC  ........................HASENPKLPELL--HKNGIAFMGPPSQAMWALGDKIASSIVAQTAGIPTLPWNGSGLRVDWQENDLQKRI
Ch ACC  ........................HASENPLLPEKLSQSKRKVIFIGPGPGNAMRSLGDKISSTIVAQSAKVPCIPWSGTGVDTVH--VDEKTGL
Yt ACC  ........................FLAENARFAEIC--ADHHLTFIGPSPDSIRAMGDKSTAKETMQRVGVPTIPGSDG-L
Sy ACC  ........................FLSENAKFAEIC--ADHHIAFIGPTPEAIRLMGDKSTAKETMQKAGVPTCPGSEG-L
An ACC  ........................FLSENANFAEQV--ERSGFIFIGPKAETIRLMGDKVSAIAAMKKAGVPCVPGSDGPL
Ec ACC  ........................FLSENKEFARCL--AAEDVVFIGPDTHAIQAMGDKIESKLLAKKAEVNTIPGFDG-V
Hm PCCA ........................FLSENKEFAKCL--AAEDVTFIGPDTHAIQAMGDKIESKLLAKRAKVNTIPGFDG-V
Rt PCCA ........................FLSENSEFADKV--VKAGITWIGPAEVIDSVGDKVSARNLAAKANVPTVPGTPG-P
Yt PC
         ***                           **          ***            *
```

FIG. 3B

```
Wh ACC   ..........................VMIKASWGGGGKGIRKVHNDDEVRALFKQVQGEVPGS----      350
Rt ACC   LNVPQDLYEKGYVKDVDDGLKAAEEVGYPVMIKASEGGGGKGIRKVNNADDFPNLFRQVQAEVPGS----
Ch ACC   LNVPQELYEKGYVKDADDGLRAAEEVGYPVMIKASEGGGGKGIRKVNNADDFPNLFRQFQAEVPGS----
Yt ACC   VSVDDDIYQKGCCTSPEDGLQKAKRIGFPVMIKASEGGGGKGIRQVEREEDFIALYHQAANEIPGS----
Sy ACC   ----LTDVDSAAKVAAEIGYPVMIKATAGGGGRGMRLVREPADLEKLFLAAQGEAEAAFGNP
An ACC   ----VETEQEGLELAKDIGYPVMIKATAGGGGRGMRLVRSPDEFVKLFLAAQGEAGAAFGNA
Ec ACC   ----GDDMDKNRAIAKRIGYPVIIKASGGGGRGMRVVRGDAELAQSISMTRAEAKAAFSND
Hm PCCA  ----VKDAEEAVRIAREIGYPVMIKASAGGGGKGMRIAWDDEETRDGFRLSSQEAASSFGDD
Rt PCCA  ----LKDADEAVRIAREIGYPVMIKASAGGGGKGMRIPWDDEETRDGFRFSSQEAASSFGDD
Yt PC    ----IETVEEALDFVNEYGYPVIIKAAFGGGGRGMRVVREGDDVADAFQRATSEARTAFGNG
                   *       ****  ***  *****  **        *

Wh ACC   PIFIMKVASQSRHLEVQLLCDKHGNVAALHSRDCSVQRRHQKIIEEGPITVAPPETIKELEQAARRLAKC      420
Rt ACC   PIFVMRLAKQSRHLEVQILADQYGNAISLFGRDCSVQRRHQKIIEEAPAAIATPAVFEHMEQCAVKLAKM
Ch ACC   PIFVMRLAKQSRHLEVQILADQYGNAISLFGRDCSGQRRHQKIIEEAPASIATSVVFEHMEQCAVKLAKM
Yt ACC   PIFIMKLAGRARHLEVQLLADQYGTNISLFGRDCSVQRRHQKIIEEAPVTIAKAETFHEMEKAAVRLGKL
Sy ACC   GLYLEKFIDRPRHVEFQILADAYGNVVHLGERDCSIQRRHQKLLEEAPSPALSADLRQKMGDAAVKVAQA
An ACC   GVYIEKFIERPRHIEFQILADQYGNVIHLGERDCSIQRRHQKLLEEAPSPALDSDLREKMGQAAVKAAQF
Ec ACC   MVYMEKYLENPRHVEIQVLADGQGNAIYLAERDCSMQRRHQKVVEEAPAPGITPELRRYIGERCAKACVD
Hm PCCA  RLLIEKFIDNPRHIEIQVLGDKHGNALWLNERECSIQRRNQKVVEEAPSIFLDAETRRAMGEQAVALARA
Rt PCCA  RLLIEKFIDNPRHIEIQVLGDKHGNALWLNERECSIQRRNQKVVEEAPSIFLDPETRRAMGEQAVAWPKA
Yt PC    TCFVERFLDKPKHIEVQLLADNHGNVVHLFERDCSVQRRHQKVVEVAPAKTLPREVRDAILTDAVKLAKE
            *   *        **  ***    *  * **  ***  **          *     **
```

FIG. 3C

```
Wh  ACC    VQYQGAATVEYLYSMETGEYFFLELNPRLQVEHPVTEWIAEINLPASQVVVGMGIPLYNIPEIRRFYGIE 490
Rt  ACC    VGYVSAGTVEYLYSQD-GSFYFLELNPRLQVEHPCTEMVADVNLPAAQLQIAMGIPLFRIKDIRMMYGVS
Ch  ACC    VGYVSAGTVEYLYSQD-GSFYFLELNPRLQVEHPCTEMVADVNLPAAQLQIAMGIPLFRIKDIRVMYGVS
Yt  ACC    VGYVSAGTVEYLYSHDDGKFYFLELNPRLQVEHPTTEMVSGVNLPAAQLQIAMGIPMHRISDIRTLYGMN
Sy  ACC    IGYIGAGTVEFLVD-ATGNFYFMEMNTRIQVEHPVTEMITGLDLIAEQIRIAQGEALRFRQADIQ-----
An  ACC    INYAGAGTIEFLLD-RSGQFYFMEMNTRIQVEHPVTEMTGVDLLVEQIRIAQGERLRLTQDQVV------
Ec  ACC    IGYRGAGTFEFLF--ENGEFYFIEMNTRIQVEHPVTEMITGVDLIKEQMRIAAGQPLSIKQEEVH-----
Hm  PCCA   VKYSSAGTVEFLVDSK-KNFYFLEMNTRLQVEHPVTECIHWPGPSPGKTVLQEHLSGTNKLIFA------
Rt  PCCA   VKYSSAGTVEFLVDSQ-KNFYFLEMNTRLQVEHPVTECITGLDLVQEMILVAKGYPLRHKQEDIP-----
Yt  PC     CGYRNAGTAEFLVDNQ-NRHYFIEINPRIQVEHTITEEITGIDIVAAQIQIAAGASLPQLGLFQDKIT--
                *      *  *   *       ** *    *  * *****  **           *

Wh  ACC    HGGGYHAWKEISAVATKFDLDKAQSVKPKGHCVAVRVTSEDPDDGFK-PTSGRVEELNFKSKPNVWAYF- 560
Rt  ACC    PWGDAPIDFENSAHVPC------------PRGHVIAARITSENPDEGFK-PSSGTVQELNFRSNKNVWGYF-
Ch  ACC    PWGDGSIDFENSAHVPC------------PRGHVIAARITSENPDEGFK-PSSGTVQELNFRSNKNVWGYF-
Yt  ACC    PHSASEIDFEFKTQDAT---KKQRRPIPKGHCTACRITSEDPNDGFK-PSGGTLHELNFRSSSNVWGYG-
Sy  ACC    -------------------------LRGHAIECRINAEDPEYNF-RPNPGRITG--YLPPGG-PGVRV
An  ACC    -------------------------LRGHAIECRINAEDPDHDF-RPAPGRISG--YLPPGG-PGVRI
Ec  ACC    -------------------------VRGHAVECRINAEDPN-TF-LPSPGKITR--FHAPGG-FGVRW
Hm  PCCA   -------------------------FNGWAVECRVYAEDPYKSFGLPSIGRLSQ--YQEPLHLPGCRV
Rt  PCCA   -------------------------ISGWAVECRVYAEDPYKSFGLPSIGRLSQ--YQEPIHLPGVRV
Yt  PC     -------------------------TRGFAIQCRITTEDPAKNFQ-PDTGRIEV--YRSAGG-NGVRL
                                         *   *    *  *          *              *
```

FIG. 3D

```
Wh ACC    ---SVKSGGAIHEFSDSQFGHVFAFGESRSLAIANMVLGLKEIQIRGEIRTNVDYTVDLLNAAEYRENMI  630
Rt ACC    ---SVAAAGGLHEFADSQFGHCFSWGENREEAISNMVVALKELSIRGDGRTTVEYLIKLLETESFQLNRI
Ch ACC    ---SVAAAGGLHEFADSQFGHCFSWGENREEAISNMVVALKELSIRGDFRTTVEYLIKLLETESFQQNRI
Yt ACC    ---SVGNNGNIHSFSDSQFGHIFAFGENRQASRKHMVVALKELSIRGDFRTTVEYLIKLLETEDFEDNTI
Sy ACC    DS-HVYTDYEIPPYYDSLIGKLIVWGATREEAIARMQRALRECAITG-LPTTLSFHQLMLQMPEFLRGEL
An ACC    DS-HVYTDYQIPPYYDSLIFKLIVWGPDRATAINRMRKALRECAITG-LPTTIGFHQRIMENPQFLQGNV
Ec ACC    ES-HIYAGYTVPPYYDSMIGKLICYGENRDVAIARMKNALQELIIDG-IKTNVDLQIRIMDNENFQHGGT
Hm PCCA   DS-GIQPGSDISIYYDPMISKLITYGSDRTEALKRMADALDNYVIRG-VTHNIALLREVIINSRFVKGDI
Rt PCCA   DS-GIQPGSDISIYHDPMISKLVTYGSDRAEALKRMEDALDSYVIRG-VTHNIPLLREVIINTRFVKGDI
Yt PC     DGGNAYAGTIISPHYDSMLVKCSCSGSTYEIVRRKMIRALIEFRIRG-VKTNIPFLLTLLTNPVFIEGTY
              *                                       *         *  **     *

Wh ACC    HTGWLDSRIAMRVRAERPPWYLSVVGGALYEASSRSSSVVTDYVGYLSKGQIPPK------------  700
Rt ACC    DTGWLDRLIAEKVQAERPDTMLGVVCGALHCADVNLRNSISNGLHSLERGQVLPA------------
Ch ACC    DTGWLDRLIAEKVQAERPDTMLGVVCGALHVADVSFRNSVSNFLHSLERGQVLPA------------
Yt ACC    TTGWLDDLITHKMTAEKPDPTLAVICGAATKAFLASEEARHKYIESLQKGQVLSK------------
Sy ACC    YTNFVEQVMLPRILKS
An ACC    STSFVQEMNK
Ec ACC    NIHYLEKKLGLQEK
Hm PCCA   STKFLSDVYPDGFKGHMLTKSEKNQLLAIASSLFVAFQLRAQHFQENSRMPVIKPDIANWELSVKLHDKV
Rt PCCA   STKFLSDVYPDGFKGHMLTPSERDQLLAIASSLFVASQLRAQRFQEHSRVPVIRPDVAKWELSVKLHDED
Yt PC     WGTFIDDTPQLFQMVSSQNRAQKLLHYLADVADNGSSIKGQIGLPKLKSNPSVPH-#-SYNMYPRVYEDF
Kp ODA                                                       PLDFNEIRQLLTTIAQTDIAEV
                                                           -##-NAIDDVLTVAL
```

FIG. 3E

```
Wh ACC    --HISLVNLTVTLNIDGSKYTIETVRGGPRSYKLRINESEVEAEIHFLRDGGLLMQLDGNSHVIYAETEA  770
Rt ACC    --HTLLNTVDVELIYEGIKYVLKVTRQSPNSYVVIMNGSCVEVDVHRLSDGGLLLSYDGSSYTTYMKEEV
Ch ACC    --HTLLNTVDVELIYEGRKYVLKVTRQSPNSYVVIMNSSCVEVDVHRLSDGGLLLSYDGSSYTTYMKEEV
Yt ACC    --DLLQTMFPVDFIHEGKRYKFTVAKSGNDRYTLFINGSKCDIILRQLSDGGLLIAIGGKSHTIYWKEEV
An ACC    TLKSDDFELTVRKAVGVNNSVVPVVTAPLSGVGSGLPSAIPIVAHAAPSPSPEPGTSRAADHAVTSSGS
Ec ACC    MDIRKIKLIELVEESGISELEISEGEESVRISRAAPAASFPVMQQAYAAPMMQQPAQSNAAAPATVPS
Hm PCCA   HTVVASNNGSVFSVEVDGSKLNVTSTWNLASPLLSVSVDGTQRTVQCLSREAGGNMSIQFLGTVYKVNIL
Rt PCCA   HTVVASNNGPTFNVEVDGSKLNVTSTWNLASPLLSVNVDGTQRTVQCLSPDAGGNMSIQFLGTVYKVHIL
Yt PC     QKMRETYGDLSVLPTRSFLSPLETDEEIEVVIEQGKTLIIKLQAVGDLNKKTGEREVYFDLNGEMRKIRV
Kp ODA    FPQPGLKFLENRHNPAAFEPVPQAEAAQPVAKAEKPAASGVYTVEVEGKAFVVKVSDGGDVSQLTAAAPA
PS TC                MKLKVTVNGTAYDVDVDVDKSHENPMGTILFGGG

840
Wh ACC    AGTRLLINGRTCLLQKEHDPSRLLADTPCKLLRFLVADGSHVVADTPYAEVEAMKM..........
Rt ACC    DRYRITIGNKTCVFEKENDPSVMRSPSAGKLIQYIVEDGGHVFAGQCYAEIEVMKMVMTLTAVESGCIHY
Ch ACC    DRYRITIGNKTCVFEKENDPSILRSPSAGKLIQYVVEDGGHVFAGQCFAEIEVMKMVMTLTAGESGCIHY
Yt ACC    AATRLSVDSMTTLLEVENDPTQLRTPSPGKLVKFLVENGEHIIKGQPYAEIEVMKMQMPLVSQENGIVQL
An ACC    QPGAKIIDQKLAEVASPMVGTFYRAPAPGE--AVFVEVGDRIRQGQTVCIIEAMKM..........
Ec ACC    MEAPAAAEISGHIVRSPMVGTFYRTPSPDA--KAFIEVGQKVNVGDTLCIVEAMKMMNQIEADKSGTVKA
Hm PCCA   TRLAAELNKFMLEKVTEDTSSVLRSPMPGVVAVSVKPGDAVAEGQEICVIEAMKMQNSMTAGKTGTVKS
Rt PCCA   TKLAAWLNKFMLEKVPKDTSSVLRSPKPGVVVAVSVKPGDMVAEGQEICVIEAMKMQNSMTAGKMGKVKL
Yt PC     ADRSQKVETVTKSKADMHDPLHIGAPMAGVIVEVKVHKGSLIKKGQPVAVLSAMKMEMIISSPSDGQVKE
Kp ODA    PAPAPAPASAPAAAAPAGAGTPVTAPLAGTVSKILVKEGDTVKAGQTVLVLEAMKMETEIRAAQAGTVRG
PS TC     TGGAPAPRAAGGAGAGEGEIPAPLAGTVSKILVKEGDTVKAGQTVLVLEAMKMETEINAPTDGKVEK
                  *         *           *     *    *    *     * ***
```

FIG. 3F

```
Wh ACC    ........................................................:900
Rt ACC    VKRPGAALDPGCVIAKMALDNPSKVQQAELHTGSLPQIQSTALRGEKLHRIF
Ch ACC    VKRPGAVLDPGCVIAKLQLDDPSRVQQAELHTGTLPQIQSTALRGEKLHRIF
Yt ACC    LKQPGSTIVAGDIMAIMTLDDPSKVKHALPFEGMLPDFGSPVIEGTKPAYKF
An ACC    ---------------------------------------------------
Ec ACC    ILVESGQPVEFDEPLVVIE
Hm PCCA   VHCQAGDTVGEGDLLVELE
Rt PCCA   VHCKAGDTVGEGDLLVELE
Yt PC     VFVSDGENVDSSDLLVLLEDQVPVETKA
Kp ODA    IAVKAGDAVAVGDTLMTLA
PS TC     VLVKERDAVQGGQGLIKIG
```

FIG. 3G

```
GTGATGATCAAGGCATCATGGGGTGGGGGTGGTAAAGGAAGGTACATAATGATGAGGTCAGAGCATTGTTAAGCAAGTG         90
 V  M  I  K  A  S  W  G  G  G  G  V  K  E  G  T  *  *  *  *  *  S  H  C  *  A  S

CAAGGAGAAGTCCCCGGATCGCCTATATTTATTATGAAGGTGGCCATCTCAGAGTGGACATGCTCTGTGACAAGCAT        180
 Q  E  V  P  G  S  P  I  F  I  M  K  V  A  S  Q  S  R  H  L  E  V  Q  L  L  C  D  K  H

GGCAACGTGGCAGCACTGCACAGTCGAGACTGTAGTGTTCAAAGAAGGCATCAAAAGATCATTGAGGAGGGACCAATTACAGTTGCTCCT    270
 G  N  V  A  A  L  H  S  R  D  C  S  V  Q  R  R  H  Q  K  I  I  E  E  G  P  I  T  V  A  P

CCAGAAACAATTAAAGAGCTTGAGCAGGCGGCAAGGCGACTAGCTAAATGTGTGCAATATCAGGGTACAGTGGAATATCTGTAC    360
 P  E  T  I  K  E  L  E  Q  A  A  R  R  L  A  K  C  V  Q  Y  Q  G  A  T  V  E  Y  L  Y

AGCATGGAAACAGGCGAATACTATTCCTGGAGCTTAATCCAAGGTTGCAGGTAGAAACACCCTGTGACCGAATGGATTGCTGAAATAAAC    450
 S  M  E  T  G  E  Y  Y  F  L  E  L  N  P  R  L  Q  V  E  H  P  V  T  E  W  I  A  E  I  N

C
                          T
TTACCTGCCATCTCAAGTTGTAGTAGGAATGGGCATACCACTCTACAACATTCCAGAGATCAGAAGACGCTTTTATGGAATAGAACATGGAGGT   540
 L  P  A  S  Q  V  V  V  G  M  G  I  P  L  Y  N  I  P  E  I  R  R  F  Y  G  I  E  H  G  G

C                          G
                                  C                          G
GGCTATCATGCTTGGAAGGAAATATCAGTGTTGCAACTAAATTGATTTGGACAAAGCACAGTCTGTAAAGCCAAAAGGTCATTGTGTA       630
 G  Y  H  A  W  K  E  I  S  A  V  A  T  K  F  D  L  D  K  A  Q  S  V  K  P  K  G  H  C  V
```

FIG. 6A

```
                                                                                        A
                                                                                        G
                                                                                        G
GCAGTTAGAGTTACTAGCGGAGGATCCAGATGATGGGTTTAAGCCTACCAGTGGAAGAGTAGAAGAGCTGAACTTTAAAAGTAAACCCAAT  720
 A  V  R  V  T  S  E  D  P  D  D  G  F  K  P  T  S  G  R  V  E  E  L  N  F  K  S  K  P  N

C         G                                           C                      C
           T         A                                           T                      T
GTTTGGGGCCTATTTCTCCGTTAAGTCCGGAGGTGCAATTCACGAGTTCTCTGATTCCCAGTTGGTCATGTTTTTGCTTTTGGGGAATCT   810
 V  W  A  Y  F  S  V  K  S  G  G  A  I  H  E  F  S  D  S  Q  F  G  H  V  F  A  F  G  E  S
           T         R
           A
                                       A
                                       A
                                       K
AGGTCATTGGCAATAGCCAATATGGTACTTGGGTTAAAAGAGATCCAAATTCGTGGAGAGATACGCACTAATGTTGACTACACTGTGGAT  900
 R  S  L  A  I  A  N  M  V  L  G  L  K  E  I  Q  I  R  G  E  I  R  T  N  V  D  Y  T  V  D

T     C
                                                                  A     T
CTCTTGAATGCTGCAGAGTACCGAGAGAAATATGATTCACACTGGTTGGCTAGACAGCAGAATAGCTATGCGCGTTAGAGCAGAGAGGCCC  990
 L  L  N  A  A  E  Y  R  E  N  M  I  H  T  G  W  L  D  S  R  I  A  M  R  V  R  A  E  R  P

CCATGGTACCTTTCAGTTGTTGGTGGAGCTCTATATGAAGCATCAAGCAGGAGCTCGAGTGTTGTAACCGATTATGTTGGTTATCTCAGT  1080
 P  W  Y  L  S  V  V  G  G  A  L  Y  E  A  S  S  R  S  S  S  V  V  T  D  Y  V  G  Y  L  S
```

FIG. 6B

```
AAAGGTCAAATACCACCAAAGCACACATCTCTCTTGTCAATTGACTGTAACACTGAATTAGATGGGAGCAAATATGAGATTGAGACAGTA  1170
K  G  Q  I  P  P  K  H  I  S  L  V  N  L  T  V  T  L  N  I  D  G  S  K  Y  T  I  E  T  V
                         C                                      C
         A               T
                 CG

CGAGGTGGACCCGTAGCTACACAAATTAAGAATTAATGAATCAGAGGTTGAGGCCAGAGATACATTTCCTGCGAGATGGCGGACTCTTAATG  1260
R  G  G  P  R  S  Y  K  L  R  I  N  E  S  E  V  E  A  E  I  H  F  L  R  D  G  G  L  L  M
                                                                                       P
                              A                                S
                                                 CG
                                                      G
                                                      T

CAGTTGGATGGAAACAGTCATGTAATTTACGCCGAGACAGAAGCTGCTGGCACGGCCTTCTAATCAATGGGAGAACATGCTTATTACAG  1350
Q  L  D  G  N  S  H  V  I  Y  A  E  T  E  A  A  G  T  R  L  L  I  N  G  R  T  C  L  L  Q
S                                                                            A
                                                                             G
                                              S
                        T
                        C

AAAGAGCACGATCCTTCCAGGTTGTTGGCTGATACACCGTGCAAACTTCTTCGGTTTTTGGTCGCGGATGGTTCTCATGTGGTTGCTGAT  1440
K  E  H  D  P  S  R  L  L  A  D  T  P  C  K  L  L  R  F  L  V  A  D  G  S  H  V  V  A  D
                                                                             S
                  T                              A  G
                  T                              A  G

ACGCCCATATGCCGAGGTGGAAGGCCATGAAAAATG
T  P  Y  A  E  V  E  A  M  K  M
```

FIG. 6C

TCTAGACTTTAACGAGATTCGTCAACTGCTGACAACTATTGCACAAACAGATATCGGCGAAGTAACGCTCAAAAGTGATGATTTTGAACT 90
L  D  F  N  E  I  R  Q  L  L  T  T  I  A  Q  T  D  I  A  E  V  T  L  K  S  D  D  F  E  L

AACGGTGCGTAAAGCTGTTGGTGTGTGAATAATAGTGTTGTGCCGGTTGTGACAGCACCCTTGAGTGGTGGTAGGTTCGGAGATTGCCATC 180
T  V  R  K  A  V  G  V  N  N  S  V  V  P  V  V  T  A  P  L  S  G  V  V  G  S  G  L  P  S

GGCTATACCGATTGTAGCCCATGCTGCCCCATCTCCAGAGCCGGGAACAAGCCGTGCTGCTGATCATGTGTCACGAGTTCTGG 270
A  I  P  I  V  A  H  A  A  P  S  P  S  P  E  P  G  T  S  R  A  A  D  H  A  V  T  S  S  G

CTCACAGCCAGGAGCAAAAATCATTGACCAAAAAATTAGCAGAAGTGGCTTCCCCAATGGTGGGAACATTTTACCGGCGGCTCCTGCACCAGG 360
S  Q  P  G  A  K  I  I  D  Q  K  L  A  E  V  A  S  P  M  V  G  T  F  Y  R  A  P  A  P  G

TGAAGCGGTATTTGTGGAAGTCGGCGATCGCATCGACAAGGTCAAACCGTCTGCATCATCGAAGGATGAAAAUG
E  A  V  F  V  E  V  G  D  R  I  R  Q  G  G  Q  T  V  C  I  I  E  A  M  K  M

FIG. 8

CYANOBACTERIAL AND PLANT ACETYL-COA CARBOXYLASE

This is a divisional of application U.S. Ser. No. 08/475,879 filed Jun. 7, 1995, now issued as U.S. Pat. No. 5,972,644, which is a divisional of U.S. Ser. No. 07/956,700 filed Oct. 2, 1992, now issued as U.S. Pat. No. 5,539,092.

The United States Government has certain rights in the present invention pursuant to Grant No. 90-34190-5207 from the United States Department of Agriculture through the midwest biotechnology consortium.

TECHNICAL FIELD OF THE INVENTION

The present invention relates to polynucleotides and polypeptides of acetyl-CoA carboxylase in cyanobacteria and plants. Polynucleotides encoding acetyl-CoA carboxylase have use in conferring herbicide resistance and in determining the herbicide resistance of plants in a breeding program.

BACKGROUND OF THE INVENTION

Acetyl-CoA carboxylase (ACC) is the first enzyme of the biosynthetic pathway to fatty acids. It belongs to a group of carboxylases that use biotin as cofactor and bicarbonate as a source of the carboxyl group. ACC catalyzes the addition of $CO_2$ to acetyl-CoA to yield malonyl-CoA in two steps as shown below.

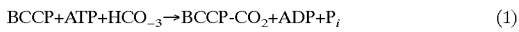

$$BCCP + ATP + HCO_3^- \rightarrow BCCP\text{-}CO_2 + ADP + P_i \quad (1)$$

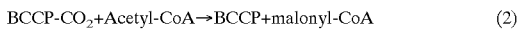

$$BCCP\text{-}CO_2 + Acetyl\text{-}CoA \rightarrow BCCP + malonyl\text{-}CoA \quad (2)$$

First, biotin becomes carboxylated at the expense of ATP. The carboxyl group is then transferred to Ac-CoA [Knowles, 1989]. This irreversible reaction is the committed step in fatty acid synthesis and is a target for multiple regulatory mechanisms. Reaction (1) is catalyzed by biotin carboxylase (BC); reaction (2) by transcarboxylase (TC); BCCP=biotin carboxyl carrier protein.

ACC purified from *E.coli* contains three distinct, separable components: biotin carboxylase (BC), a dimer of 49-kD monomers, biotin carboxyl carrier protein (BCCP) a dimer of 17-kD monomers and transcarboxylase (TC), a tetramer containing two each of 33-kD and 35-kD subunits. The biotin prosthetic group is covalently attached to the γ-amino group of a lysine residue of BCCP. The primary structure of *E.coli* BCCP and BC is known (fabE and fabG genes, respectively, have been cloned and sequenced) [Alix, 1989; Maramatsu, et al., 1989; Li, et al., 1992]. In bacteria, fatty acids are primarily precursors of phospholipids rather than storage fuels, and so ACC activity is coordinated with cell growth and division.

Rat and chicken ACC consist of a dimer of about 265 kD (rat has also a 280 kD isoform) subunits that contains all of the bacterial enzyme activities. Both mammalian and avian ACC are cytoplasmic enzymes and their substrate is transported out of mitochondria via citrate. ACC content and/or activity varies with the rate of fatty acid synthesis or energy requirements in different nutritional, hormonal and developmental states. ACC mRNA is transcribed using different promoters and can be regulated by alternative splicing. ACC catalytic activity is regulated allosterically by a number of metabolites and by reversible phosphorylation of the enzyme. The primary structure of rat and chicken enzymes, and the primary structure of the 5'-untranslated region of mRNA have been deduced from cDNA sequences [Lopez-Casillas, et al., 1988; Takai, et al., 1988]. The primary structure of yeast ACC has also been determined [Feel, et al., 1992].

Studies on plant ACC are far less advanced [Harwood, 1988]. It was originally thought that plant ACC consisted of low molecular weight dissociable subunits similar to those of bacteria. Those results appeared to be due to degradation of the enzyme during purification. More recent results indicate that the wheat enzyme, as well as those from parsley and rape, are composed of two about 220 kD monomers, similar to the enzyme from rat and chicken [Harwood, 1988; Egin-Buhler, et al., 1983; Wurtelle, et al., 1990; Slabas, et al., 1985]. The plant ACC is located entirely in the stroma of plastids, where all plant fatty acid synthesis occurs. No plant gene encoding ACC has been reported to date. The gene must be nuclear because no corresponding sequence is seen in the complete chloroplast DNA sequences of tobacco, liverwort or rice. ACC, like the vast majority of chloroplast proteins which are encoded in nuclear DNA, must be synthesized in the cytoplasm and then transported into the chloroplast, probably requiring a chloroplast transport sequence. Although the basic features of plant ACC must be the same as those of prokaryotic and other eucaryotic ACCs, significant differences can be also expected due, for example, to differences in plant cell metabolism and ACC cellular localization.

Structural similarities deduced from the available amino acid sequences suggest strong evolutionary conservation among biotin carboxylases and biotin carboxylase domains of all biotin-dependent carboxylases. On the contrary, the BCCP domains show very little conservation outside the sequence E(A/V)MKM (lysine residue is biotinylated) which is found in all biotinylated proteins including pyruvate carboxylase and propionyl-CoA carboxylase [Knowles, 1989; Samols, et al., 1988]. It is likely that the three functional domains of ACC located in *E.coli* on separate polypeptides are present in carboxylases containing two (human propionyl-CoA carboxylase) or only one (yeast pyruvate carboxylase, mammalian, avian and probably also plant ACC) polypeptide as a result of gene fusion during evolution.

Several years ago it was shown that aryloxyphenoxypropionates and cyclohexanediones, powerful herbicides effective against monocot weeds, inhibit fatty acid biosynthesis in sensitive plants. Recently it has been determined that ACC is the target enzyme for both of these classes of herbicide. Dicotyledonous plants are resistant to these compounds, as are other eukaryotes and prokaryotes. The mechanisms of inhibition and resistance of the enzyme are not known [Lichtenthaler, 1990].

It has occurred to others that the evolutionary relatedness of cyanobacteria and plants make the former useful sources of cloned genes for the isolation of plant cDNAs. For example, Pecker et al used the cloned gene for the enzyme phytoene desaturase, which functions in the synthesis of carotenoids, from cyanobacteria as a probe to isolate the cDNA for that gene from tomato [Pecker, et al., 1992].

BRIEF SUMMARY OF THE INVENTION

In one aspect the present invention provides an isolated and purified polynucleotide of from about 1350 to about 40,000 base pairs that encodes a polypeptide having the ability to catalyze the carboxylation of a biotin carboxyl carrier protein of a cyanobacterium. Preferably, that polypeptide is a subunit of acetyl-CoA carboxylase and participates in the carboxylation of acetyl-CoA. In a preferred embodiment, a cyanobacterium is Anabaena or Synechococcus. The biotin carboxyl carrier protein preferably includes the amino acid residue sequence shown in SEQ ID NO:111 or a functional equivalent thereof.

In another preferred embodiment, the polypeptide has the amino acid residue sequence of FIG. 1 or FIG. 2. The polynucleotide preferably includes the DNA sequence of SEQ ID NO:1, the DNA sequence of SEQ ID NO:1 from about nucleotide position 1300 to about nucleotide position 2650 or the DNA sequence of SEQ ID NO:5.

In another aspect, the present invention provides an isolated and purified polynucleotide of from about 480 to about 40,000 base pairs that encodes a biotin carboxyl carrier protein of a cyanobacterium and, preferably Anabaena. The biotin carboxyl carrier protein preferably includes the amino acid residue sequence of SEQ ID NO:111 and the polynucleotide preferably includes the DNA sequence of SEQ ID NO:110.

Another polynucleotide provided by the present invention encodes a plant polypeptide having the ability to catalyze the carboxylation of acetyl-CoA. A plant polypeptide is preferably (1) a monocotyledonous plant polypeptide such as a wheat, rice, maize, barley, rye, oats or timothy grass polypeptide or (2) a dicotyledonous plant polypeptide such as a soybean, rape, sunflower, tobacco, Arabiodopsis, petunia, Canola, pea, bean, tomato, potato, lettuce, spinach, alfalfa, cotton or carrot polypeptide. Preferably, that polypeptide is a subunit of ACC and participates in the carboxylation of acetyl-CoA.

Such a polynucleotide preferably includes the nucleotide sequence of SEQ ID NO:108 and encodes the amino acid residue sequence of SEQ ID NO:109.

In yet another aspect, the present invention provides an isolated and purified DNA molecule comprising a promoter operatively linked to a coding region that encodes (1) a polypeptide having the ability to catalyze the carboxylation of a biotin carboxyl carrier protein of a cyanobacterium, (2) a biotin carboxyl carrier protein of a cyanobacterium or (3) a plant polypeptide having the ability to catalyze the carboxylation of acetyl-CoA, which coding region is operatively linked to a transcription-terminating region, whereby said promoter drives the transcription of said coding region.

In another aspect, the present invention provides an isolated polypeptide having the ability to catalyze the carboxylation of a biotin carboxyl carrier protein of a cyanobacterium such as Anabaena or Synechococcus. Preferably a biotin carboxyl carrier protein includes the amino acid sequence of SEQ ID NO:111 and the polypeptide has the amino acid residue .sequence of FIG. 1 or FIG. 2 (SEQ ID NO:5 and SEQ ID NO:6).

The present invention also provides (1) an isolated and purified biotin carboxyl carrier protein of a cyanobacterium such as Anabaena, which protein includes the amino acid residue sequence of SEQ ID NO:111 and (2) an isolated and purified plant polypeptide having a molecular weight of about 220 kD, dimers of which have the ability to catalyze the carboxylation of acetyl-CoA.

In yet another aspect, the present invention provides a process of increasing the herbicide resistance of a monocotyledonous plant comprising transforming the plant with a DNA molecule comprising a promoter operatively linked to a coding region that encodes a herbicide resistant polypeptide having the ability to catalyze the carboxylation of acetyl-CoA, which coding region is operatively linked to a transcription-terminating region, whereby the promoter is capable of driving the transcription of the coding region in a monocotyledonous plant.

Preferably, a polypeptide is an acetyl-CoA carboxylase enzyme and, more preferably, a dicotyledonous plant acetyl-CoA carboxylase. In a preferred embodiment, a coding region includes the DNA sequence of SEQ ID NO:108 and a promoter is CaMV35.

The present invention also provides a transformed plant produced in accordance with the above process as well as a transgenic plant and a transgenic plant seed having incorporated into its genome a transgene that encodes a herbicide resistant polypeptide having the ability to catalyze the carboxylation of acetyl-CoA.

In yet another aspect, the present invention provides a process of altering the carboxylation of acetyl-CoA in a cell comprising transforming the cell with a DNA molecule comprising a promoter operatively linked to a coding region that encodes a plant polypeptide having the ability to catalyze the carboxylation of acetyl-CoA, which coding region is operatively linked to a transcription-terminating region, whereby the promoter is capable of driving the transcription of the coding region in the cell.

In a preferred embodiment, a cell is a cyanobacterium or a plant cell and a plant polypeptide is a monocotyledonous plant acetyl-CoA carboxylase enzyme such as wheat acetyl-CoA carboxylase enzyme. The present invention also provides a transformed cyanobacterium produced in accordance with such a process.

The present invention still further provides a process for determining the inheritance of plant resistance to herbicides of the aryloxyphenocypropionate or cyclohexanedione class, which process comprises the steps of:
  (a) measuring resistance to herbicides of the aryloxyphenocypropionate or cyclohexanedione class in a parental plant line and in progeny of the parental plant line;
  (b) purifying DNA from said parental plant line and the progeny;
  (c) digesting the DNA with restriction enzymes to form DNA fragments;
  (d) fractionating the fragments on a gel;
  (e) transferring the fragments to a filter support;
  (f) annealing the fragments with a labelled RFLP probe consisting of a DNA molecule that encodes acetyl-CoA carboxylase or a portion thereof; and
  (g) detecting the presence of complexes between the fragments and the RFLP probe; and
  (h) correlating the herbicide resistance of step (a) with the complexes of step (g) and thereby the inheritance of herbicide resistance.

Preferably, the acetyl-CoA carboxylase is a dicotyledonous plant acetyl-CoA carboxylase enzyme or a mutated monocotyledonous plant acetyl-CoA carboxylase that confers herbicide resistance or a hybrid acetyl-CoA carboxylase comprising a portion of a dicotyledonous plant acetyl-CoA carboxylase, a portion of a dicotyledonous plant acetyl-CoA carboxylase or one or more domains of a cyanobacterial acetyl-CoA carboxylase.

In still yet another aspect, the present invention provides a process for identifying herbicide resistant variants of a plant acetyl-CoA carboxylase comprising the steps of:
  (a) transforming cyanobacteria with a DNA molecule that encodes a monocotyledonous plant acetyl-CoA carboxylase enzyme to form transformed cyanobacteria;
  (b) inactivating cyanobacterial acetyl-CoA carboxylase;
  (c) exposing the transformed cyanobacteria to a herbicide that inhibits acetyl-CoA carboxylase activity;
  (d) identifying transformed cyanobacteria that are resistant to the herbicide; and
  (e) characterizing DNA that encodes acetyl-CoA carboxylase from the cyanobacteria of step (d).

BRIEF DESCRIPTION OF THE DRAWINGS

In the drawings which form a portion of the specification:

FIG. 1 shows the complete nucleotide sequence (SEQ ID NO:1) of a HindIII fragment that includes the fabG gene coding biotin carboxylase from the cyanobacterium Anabaena 7120, along with the amino acid sequence (SEQ ID NO:2–4) deduced from the coding sequence of the DNA.

FIG. 2 shows the nucleotide sequence (SEQ ID NO:5) of the coding region of the fabG gene from the cyanobacterium Anacystis nidulans R2, along with the amino acid sequence (SEQ ID NO:6) deduced from the coding sequence of the DNA.

FIG. 3 shows an alignment of the amino acid sequences (SEQ ID NOS:6–107 and 109) of the BC proteins from both cyanobacteria and from E. coli, the BCCP proteins from Anabaena and from E. coli, along with the ACC enzymes from rat and chicken and several other biotin-containing carboxylases. Stars indicate positions that are identical in all sequences or all but one. The conventional one letter abbreviations for amino acids are used. The BC domains are indicated by a solid underline, the BCCP domains by a dashed underline. The symbol # indicates sequences not related to BC and, therefore, not considered in the alignment. The wheat ACC sequence deduced from the sequence of our cloned cDNA fragment is on the top line. Abbreviations used in the Figure are: Wh ACC, wheat ACC; Rt, rat; Ch, chicken; Yt, yeast; Sy ACC, Synechococcus BC; An ACC, Anabaena BC and BCCP proteins; EC ACC, E. coli BC and BCCP; Hm PCCA, human propionyl CoA carboxylase; Rt PCCA, rat propionyl CoA carboxylase; Yt PC, yeast pyruvate carboxylase.

FIG. 6 shows the nucleotide sequence (SEQ ID NO:108) of a portion of the wheat cDNA corresponding to ACC. The amino acid sequence (SEQ ID NO:109) deduced from the nucleotide sequence is also shown. The underlined sequences correspond to the primer sites shown in FIG. 5. A unique sequence was found for the BC domain, suggesting that a single mRNA was the template for the final amplified products. For the sequence between the BC and BCCP domains, three different variants were found among four products sequenced, suggesting that three different gene transcripts were among the amplified products. This is not unexpected because wheat is hexaploid, i.e. it has three pairs of each chromosome.

FIG. 8 shows the nucleotide sequence (SEQ ID NO:110) of a PCR product corresponding to a portion of the fabE gene encoding about 75% of the biotin carboxyl carrier protein from the cyanobacterium Anabaena, along with the amino acid sequence (SEQ ID NO:111) deduced from the coding sequence. The underlined sequences correspond to the primer sites shown in FIG. 7.

DETAILED DESCRIPTION OF THE INVENTION

I. Definitions

Figure 4:
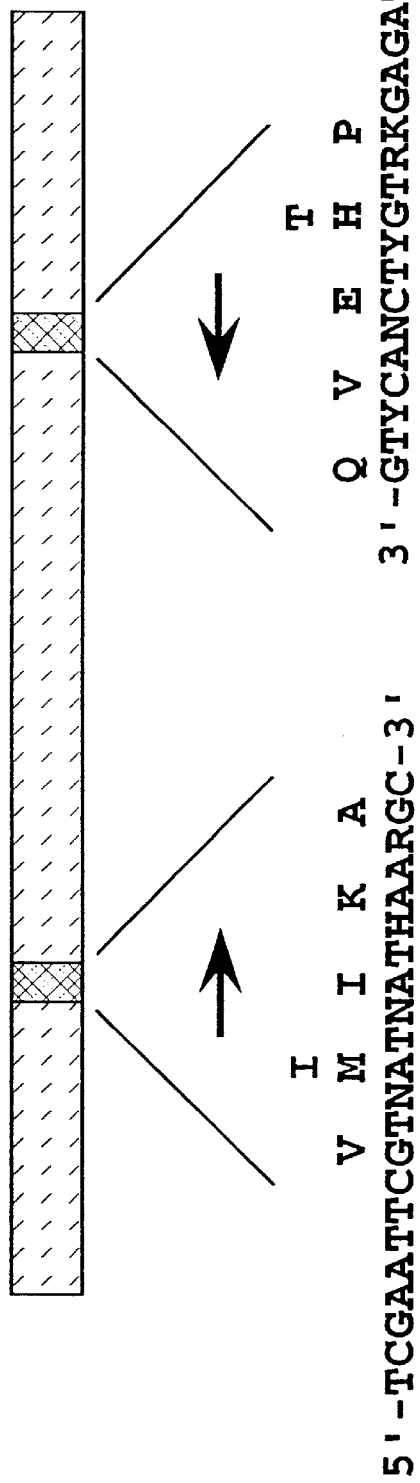
FIG. 4 shows the conserved amino acid sequences used to design primers for the PCR to amplify the BC domain of ACC from wheat. The sequences of the oligonucleotide primers (SEQ ID NOS:112 and 113) are also shown. In this and other figures showing primer sequences, A means adenine, C means cytosine, G means guanine, T means thymine, N means all four nucleotides, Y means T or C, R means A or G, K means G or T, M means A or C, W means A or T, and H means A,C or T.

The following words and phrases have the meanings set forth below.

Expression: The combination of intracellular processes, including transcription and translation undergone by a coding DNA molecule such as a structural gene to produce a polypeptide.

Promoter: A recognition site on a DNA sequence or group of DNA sequences that provide an expression control element for a structural gene and to which RNA polymerase specifically binds and initiates RNA synthesis (transcription) of that gene.

Regeneration: The process of growing a plant from a plant cell (e.g. plant protoplast or explant).

Structural gene: A gene that is expressed to produce a polypeptide.

Transformation: A process of introducing an exogenous DNA sequence (e.g. a vector, a recombinant DNA molecule) into a cell or protoplast in which that exogenous DNA is incorporated into a chromosome or is capable of autonomous replication.

Transformed cell: A cell whose DNA has been altered by the introduction of an exogenous DNA molecule into that cell.

Transgenic cell: Any cell derived or regenerated from a transformed cell or derived from a transgenic cell. Exemplary transgenic cells include plant calli derived from a transformed plant cell and particular cells such as leaf, root, stem, e.g. somatic cells, or reproductive (germ) cells obtained from a transgenic plant.

Transgenic plant: A plant or progeny thereof derived from a transformed plant cell or protoplast, wherein the plant DNA contains an introduced exogenous DNA molecule not originally present in a native, non-transgenic plant of the same strain. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast as being a transgenic plant, and that usage will be followed herein.

Vector: A DNA molecule capable of replication in a host cell and/or to which another DNA segment can be operatively linked so as to bring about replication of the attached segment. A plasmid is an exemplary vector.

Certain polypeptides are disclosed herein as amino acid residue sequences. Those sequences are written left to right in the direction from the amino to the carboxy terminus. In accordance with standard nomenclature, amino acid residue sequences are denominated by either a single letter or a three letter code as indicated below.

| Amino Acid Residue | 3-Letter Code | 1-Letter Code |
|---|---|---|
| Alanine | Ala | A |
| Arginine | Arg | R |

-continued

| Amino Acid Residue | 3-Letter Code | 1-Letter Code |
| --- | --- | --- |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The present invention provides polynucleotides and polypeptides relating to a whole or a portion of acetyl-CoA carboxylase (ACC) of cyanobacteria and plants as well as processes using those polynucleotides and polypeptides.

II. Polynucleotides

As used herein the term "polynucleotide" means a sequence of nucleotides connected by phosphodiester linkages. A polynucleotide of the present invention can comprise from about 2 to about several hundred thousand base pairs. Preferably, a polynucleotide comprises from about 5 to about 150,000 base pairs. Preferred lengths of particular polynucleotides are set hereinafter.

A polynucleotide of the present invention can be a deoxyribonucleic acid (DNA) molecule or a ribonucleic acid (RNA) molecule. Where a polynucleotide is a DNA molecule, that molecule can be a gene or a cDNA molecule. Nucleotide bases are indicated herein by a single letter code: adenine (A), guanine (G), thymine (T), cytosine (C), and uracil (U).

A. Cyanobacteria

In one embodiment, the present invention contemplates an isolated and purified polynucleotide of from about 1350 to about 40,000 base pairs that encodes a polypeptide having the ability to catalyze the carboxylation of a biotin carboxyl carrier protein of a cyanobacterium.

Preferably, a biotin carboxyl carrier protein (BCCP) is derived from a cyanobacterium such as Anabaena or Synechococcus. A preferred Anabaena is Anabaena 7120. A preferred Synechococcus is *Anacystis nidulans* R2 (Synechococcus sp. strain pcc7942). A biotin carboxyl carrier protein preferably includes the amino acid residue sequence shown in SEQ ID NO:111 or a functional equivalent thereof.

Figure 1A:
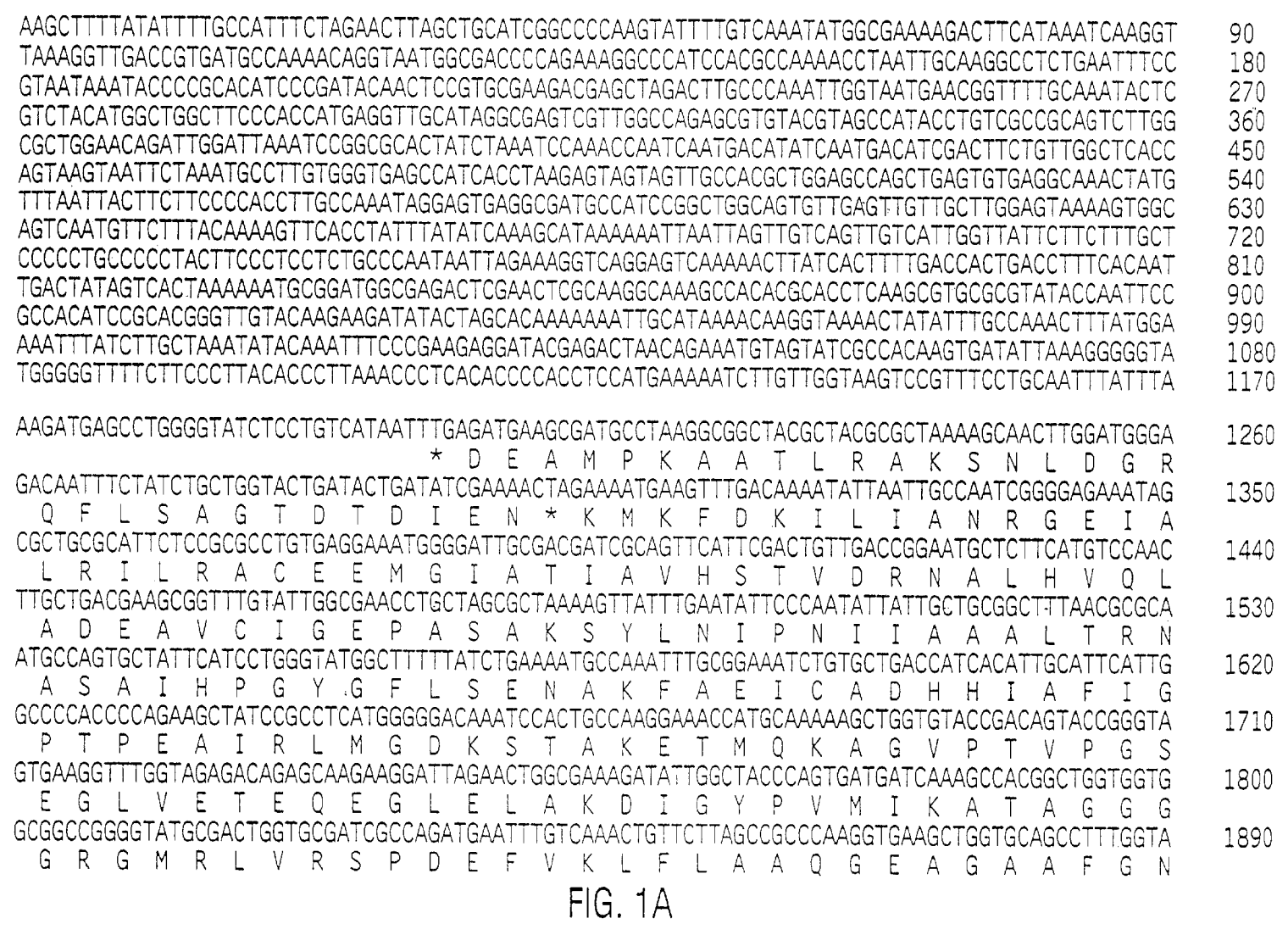

Preferably, a polypeptide is a biotin carboxylase enzyme of a cyanobacterium, which enzyme is a subunit of acetyl-CoA carboxylase and participates in the carboxylation of acetyl-CoA. In a preferred embodiment, a polypeptide encoded by such a polynucleotide has the amino acid residue sequence of FIG. 1 or FIG. 2, (SEQ ID NO:5 and SEQ ID NO:6) or a functional equivalent of those sequences.

A polynucleotide preferably includes the DNA sequence of SEQ ID NO:1 (FIG. 1) or the DNA sequence of SEQ ID NO:1 (FIG. 1) from about nucleotide position 1300 to about nucleotide position 2650.

The polynucleotide of SEQ ID NO:1 contains a gene that encodes the enzyme biotin carboxylase (BC) from the cyanobacterium Anabaena. This gene was cloned in the following way: total DNA from Anabaena was digested with various restriction enzymes, fractionated by gel electrophoresis, and blotted onto GeneScreen Plus (DuPont). The blot was hybridized at low stringency (1 M NaCl, 57° C.) with a probe consisting of a SstII-PstI fragment containing about 90% of the coding region of the fabG gene from *E. coli*. This probe identified a 3.1-kb HindIII fragment in the Anabaena digest that contained similar sequences. A mixture of about 3-kb HindIII fragments of Anabaena DNA was purified, then digested with NheI, yielding a HindIII-NheI fragment of 1.6 kb that hybridized with the fabG probe. The 1.6-kb region was purified by gel electrophoresis and cloned into pUC18.

Plasmid minipreps were made from about 160 colonies, of which four were found to contain the 1.6-kb HindIII-NheI fragment that hybridized with the fabG probe. The 1.6-kb Anabaena fragment was then used as probe to screen, at high stringency (1 M NaCl, 65° C.), a cosmid library of Anabaena DNA inserts averaging 40 kb in size. Five were found among 1920 tested, all of which contained the same size HindIII and NheI fragments as those identified by the *E. coli* probe previously. From one of the cosmids, the 3.1-kb HindIII fragment containing the Anabaena fabG gene was subcloned into pUC18 and sequenced using the dideoxy chain termination method. The complete nucleotide sequence of this fragment is shown in FIG. 1 (SEQ ID NO:1 and SEQ ID NO:2).

A similar procedure was used to clone the fabG gene from Synechococcus. In this case, the initial Southern hybridization showed that the desired sequences were contained in part on an 0.8-kb BamHI-PstI fragment. This size fragment was purified in two steps and cloned into the plasmid Bluescript KS. Minipreps of plasmids from 200 colonies revealed two that contained the appropriate fragment of Synechococcus DNA. This fragment was used to probe, at high stringency, a library of Synechococcus inserts in the cosmid vector pWB79. One positive clone was found among 1728 tested. This cosmid contained a 2-kb BamHI and a 3-kb PstI fragment that had previously been identified by the *E. coli* fabG probe in digests of total Synechococcus DNA. Both fragments were subcloned from the cosmid into Bluescript KS and 2.4 kb, including the coding part of the fabG gene, were sequenced. The complete sequence of the coding region of the Synechococcus fabG gene is shown in FIG. 2 (SEQ ID NO:5 and SEQ ID NO:6).

In another aspect, the present invention provides an isolated and purified polynucleotide of from about 480 to about 40,000 base pairs that encodes a biotin carboxyl carrier protein of a cyanobacterium. That biotin carboxyl carrier protein preferably includes the amino acid residue sequence of FIG. 8 (SEQ ID NO:111) or a functional equivalent thereof. A preferred polynucleotide that encodes that polypeptide includes the DNA sequence of SEQ ID NO:110 (FIG. 8).

B. Plants

Another polynucleotide contemplated by the present invention encodes a plant polypeptide having the ability to catalyze the carboxylation of acetyl-CoA. Such a plant polypeptide is preferably a monocotyledonous or a dicotyledonous plant acetyl-CoA carboxylase enzyme.

An exemplary and preferred monocotyledonous plant is wheat, rice, maize, barley, rye, oats or timothy grass. An exemplary and preferred dicotyledonous plant is soybean, rape, sunflower, tobacco, Arabidopsis, petunia, pea, Canola, bean, tomato, potato, lettuce, spinach, alfalfa, cotton or carrot.

A monocotyledonous plant polypeptide is preferably wheat ACC, which ACC includes the amino acid residue sequence of SEQ ID NO:109 (FIG. 6) or a functional equivalent thereof. A preferred polynucleotide that encodes such a polypeptide includes the DNA sequence of SEQ ID NO:108 (FIG. 6).

Amino acid sequences of biotin carboxylase (BC) from Anabaena and Synechococcus show great similarity with amino acid residue sequences from other ACC enzymes as well as with the amino acid residue sequences of other biotin-containing enzymes (See FIG. 3). Based on that homology, the nucleotide sequences shown in FIG. 4 (SEQ ID NO:112 and SEQ ID NO:113) were chosen for the construction of primers for polymerase chain reaction amplification of a corresponding region of the gene for ACC from wheat. Those primers have the nucleotide sequences shown below:

Primer 1

5' TCGAATTCGTNATNATHAARGC 3' (SEQ ID NO:112);

Primer 2

5' GCTCTAGAGKRTGYTCNACYTG 3' (SEQ ID NO:113);

where N is A, C, G or T; H is A, C or T; R is A or G; Y is T or C and K is G or T. Primers 1 and 2 comprise a 14-nucleotide specific sequence based on a conserved amino acid sequence and an 8-nucleotide extension at the 5'-end of the primer to provide anchors for rounds of amplification after the first round and to provide convenient restriction sites for analysis and cloning.

cDNA amplification began with a preparation of total polyA-containing mRNA from eight day-old green plants (*Triticum aestivum* var. Era as described in [Lamppa, et al., 1992]). The first strand of cDNA was synthesized using random hexamers as primers for AMV reverse transcriptase following procedures described in [Haymerle, et al., 1986], with some modifications. Reverse transcriptase was inactivated by heat and low molecular weight material was removed by filtration.

The PCR was initiated by the addition of polymerase at 95° C. Amplification was for 45 cycles, each 1 min at 95°, 1 min at 42–46° and 2 min at 72° C. Both the reactions using Anabaena DNA and the single-stranded wheat cDNA as template yielded about 440 base pair (bp) products. The wheat product was eluted from a gel and reamplified using the same primers. That product, also 440 bp, was cloned into the Invitrogen (San Diego, Calif.) vector pCR1000 using their A/T tail method, and sequenced.

In eukaryotic ACCs, a BCCP domain is located about 300 amino acids away from the end of the BC domain, on the C-terminal side. Therefore, it is possible to amplify the cDNA covering the interval between the BC and BCCP domains using primers from the C-terminal end of the BC domain and the conserved MKM region of the BCCP. The BC primer was based on the wheat cDNA sequence obtained as described above. Those primers, each with 6- or 8-base 5'-extensions, are shown below and in FIG. 5.

Primer 3

5' GCTCTAGAATACTATTTCCTG 3' (SEQ ID NO:114)

Primer 4

5' TCGAATTCWNCATYTTCATNRC 3' (SEQ ID NO:115)

N, R and Y are as defined above. W is A or T. The BC primer (Primer 3) was based on the wheat cDNA sequence obtained as described above. The MKM primer (primer 4) was first checked by determining whether it would amplify the fabE gene coding BCCP from Anabaena DNA. This PCR was primed at the other end by using a primer based on the N-terminal amino acid residue sequence as determined on protein purified from Anabaena extracts by affinity chromatography. Those primers are shown below and in FIG. 7.

Primer 5

5' GCTCTAGAYTTYAAYGARATHMG 3' (SEQ ID NO:116)

Primer 4

5' TCGAATTCWNCATYTTCATNRC 3' (SEQ ID NO:115)

H, N, R, T, Y and W are as defined above. M is A or C. This amplification (using the conditions described above) yielded the correct fragment of the Anabaena fabE gene, which was used to identify cosmids that contained the entire fabE gene and flanking DNA. An about 4 kb XbaI fragment containing the gene was cloned into the vector Bluescript KS for sequencing.

Primers 3 and 4 were then used to amplify the intervening sequence in wheat cDNA. Again, the product of the first PCR was eluted and reamplified by another round of PCR, then cloned into the Invitrogen vector pCRII.

The complete 1.1 kb of the amplified DNA was sequenced, shown in FIG. 6, (SEQ ID NO:108) nucleotides 376–1473. The nucleotide sequence of the BC domain is also shown in FIG. 6, (SEQ ID NO:108) nucleotides 1–422. Three clones of the BC domain gave the sequence shown. Four clones of the 1.1-kb fragment differed at several positions, corresponding to three closely related sequences, all of which are indicated in the Figure. Most of the sequence differences are in the third codon position and are silent in terms of the amino acid sequence.

The amino acid sequence of the polypeptide predicted from the cDNA sequence for this entire fragment of wheat cDNA (1473 nucleotides) is compared with the amino acid sequences of other ACC enzymes and related enzymes from various sources in FIG. 3. The most significant identities are with the ACC of rat, chicken and yeast, as shown in the table below. Less extensive similarities are evident with the BC subunits of bacteria and the BC domains of other enzymes such as pyruvate carboxylase of yeast and propionyl CoA carboxylase of rat. The amino acid identities between wheat ACC and other biotin-dependent enzymes, within the BC domain (amino acid residues 312–630 in FIG. 3) are shown below in Table 1.

TABLE 1

|  | % identity with wheat ACC | % identity with rat ACC |
|---|---|---|
| rat ACC | 58 | (100) |
| chicken ACC | 57 |  |
| yeast ACC | 56 |  |
| Synechococcus ACC | 32 |  |
| Anabaena ACC | 30 |  |
| E. coli ACC | 33 |  |
| rat propionyl CoA carboxylase | 32 | 31 |
| yeast pyruvate carboxylase | 31 |  |

C. Probes and Primers

In another aspect, DNA sequence information provided by the invention allows for the preparation of relatively short DNA (or RNA) sequences having the ability to specifically hybridize to gene sequences of the selected polynucleotides disclosed herein. In these aspects, nucleic acid probes of an appropriate length are prepared based on a consideration of a selected ACC gene sequence, e.g., a sequence such as that shown in FIGS. 1, 2, 6 or 8 (SEQ ID NO:110 and SEQ ID NO:111). The ability of such nucleic acid probes to specifically hybridize to an ACC gene sequence lend them particular utility in a variety of embodiments. Most importantly, the probes can be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of an ACC gene from a cyanobacterium or a plant using PCR technology. Segments of ACC genes from other organisms can also be amplified by PCR using such primers.

To provide certain of the advantages in accordance with the present invention, a preferred nucleic acid sequence employed for hybridization studies or assays includes sequences that are complementary to at least a 10 to 30 or so long nucleotide stretch of an ACC sequence, such as that shown in FIGS. 1, 2, 6 or 8 (SEQ ID NO:110 and SEQ ID NO:111). A size of at least 10 nucleotides in length helps to ensure that the fragment will be of sufficient length to form a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102, herein incorporated by reference, or by excising selected DNA fragments from recombinant plasmids containing appropriate inserts and suitable restriction sites.

Accordingly, a nucleotide sequence of the invention can be used for its ability to selectively form duplex molecules with complementary stretches of the gene. Depending on the application envisioned, one will desire to employ varying conditions of hybridization to achieve varying degree of selectivity of the probe toward the target sequence. For applications requiring a high degree of selectivity, one will typically desire to employ relatively stringent conditions to form the hybrids, for example, one will select relatively low salt and\or high temperature conditions, such as provided by 0.02M–0.15M NaCl at temperatures of 50° C. to 70° C. These conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate an ACC coding sequences for related species, functional equivalents, or the like, less stringent hybridization conditions will typically be needed in order to allow formation of the heteroduplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a polynucleotide of the present invention in combination with an appropriate label for detecting hybrid formation. A wide variety of appropriate labels are known in the art, including radioactive, enzymatic or other ligands, such as avidin/biotin, which are capable of giving a detectable signal.

In general, it is envisioned that a hybridization probe described herein is useful both as a reagent in solution hybridization as well as in embodiments employing a solid phase. In embodiments involving a solid phase, the test DNA (or RNA) is adsorbed or otherwise affixed to a selected matrix or surface. This fixed nucleic acid is then subjected to specific hybridization with selected probes under desired conditions. The selected conditions depend as is well known in the art on the particular circumstances and criteria required (e.g., on the G+C contents, type of target nucleic acid, source of nucleic acid, size of hybridization probe). Following washing of the matrix to remove nonspecifically bound probe molecules, specific hybridization is detected, or even quantified, by means of the label.

D. Expression Vector

The present invention contemplates an expression vector comprising a polynucleotide of the present invention. Thus, in one embodiment an expression vector is an isolated and purified DNA molecule comprising a promoter operatively linked to an coding region that encodes a polypeptide having the ability to catalyze the carboxylation of a biotin carboxyl carrier protein of a cyanobacterium, which coding region is operatively linked to a transcription-terminating region, whereby the promoter drives the transcription of the coding region.

As used herein, the term "operatively linked" means that a promoter is connected to an coding region in such a way that the transcription of that coding region is controlled and regulated by that promoter. Means for operatively linking a promoter to a coding region are well known in the art.

Where an expression vector of the present invention is to be used to transform a cyanobacterium, a promoter is selected that has the ability to drive and regulate expression in cyanobacteria. Promoters that function in bacteria are well known in the art. An exemplary and preferred promoter for the cyanobacterium Anabaena is the glnA gene promoter. An exemplary and preferred promoter for the cyanobacterium Synechococcus is the psbAI gene promoter. Alternatively, the cyanobacterial fabG gene promoters themselves can be used.

Where an expression vector of the present invention is to be used to transform a plant, a promoter is selected that has the ability to drive expression in plants. Promoters that function in plants are also well known in the art. Useful in expressing the polypeptide in plants are promoters that are inducible, viral, synthetic, constitutive as described by Poszkowski et al., *EMBO J.*, 3:2719 (1989) and Odell et al., *Nature*, 313:810 (1985), and temporally regulated, spatially regulated, and spatiotemporally regulated as given in Chua et al., *Science*, 244:174–181 (1989).

A promoter is also selected for its ability to direct the transformed plant cell's or transgenic plant's transcriptional activity to the coding region. Structural genes can be driven by a variety of promoters in plant tissues. Promoters can be near-constitutive, such as the CaMV 35S promoter, or tissue specific or developmentally specific promoters affecting dicots or monocots.

Where the promoter is a near-constitutive promoter such as CaMV 35S, increases in polypeptide expression are found in a variety of transformed plant tissues (e.g. callus, leaf, seed and root). Alternatively, the effects of transformation can be directed to specific plant tissues by using plant integrating vectors containing a tissue-specific promoter.

An exemplary tissue-specific promoter is the Lectin promoter, which is specific for seed tissue. The Lectin protein in soybean seeds is encoded by a single gene (Le1) that is only expressed during seed maturation and accounts for about 2 to about 5 percent of total seed mRNA. The Lectin gene and seed-specific promoter have been fully characterized and used to direct seed specific expression in transgenic tobacco plants. See. e.g., Vodkin et al., *Cell,* 34:1023 (1983) and Lindstrom et al., *Developmental Genetics,* 11:160 (1990).

An expression vector containing a coding region that encodes a polypeptide of interest is engineered to be under control of the Lectin promoter and that vector is introduced into plants using, for example, a protoplast transformation method. Dhir et al., *Plant Cell Reports,* 10:97 (1991). The expression of the polypeptide is directed specifically to the seeds of the transgenic plant.

A transgenic plant of the present invention produced from a plant cell transformed with a tissue specific promoter can be crossed with a second transgenic plant developed from a plant cell transformed with a different tissue specific promoter to produce a hybrid transgenic plant that shows the effects of transformation in more than one specific tissue.

Exemplary tissue-specific promoters are corn sucrose synthetase 1 (Yang et al. *Proc. Natl. Acad. Sci, U.S.A.,* 87:4144–48 (1990)), corn alcohol dehydrogenase 1 (Vogel et al., *J. Cell Biochem.,* (supplement 13D, 312) (1989)), corn zein 19KD gene (storage protein) (Boston et al., *Plant Physiol.,* 83:742–46), corn light harvesting complex (Simpson, *Science,* 233:34 (1986), corn heat shock protein (O'Dell et al., *Nature,* 313:810–12 (1985), pea small subunit RuBP Carboxylase (Poulsen et al., *Mol. Gen. Genet.,* 205:193–200 (1986); Cashmore et al., *Gen. Eng. of Plants,* Plenum Press, New York, 29–38 (1983), Ti plasmid mannopine synthase (Langridge et al., *Proc. Natl. Acad. Sci. USA,* 86:3219–3223 (1989), Ti plasmid nopaline synthase (Langridge et al., *Proc. Natl. Acad. Sci. USA,* 86:3219–3223 (1989), petunia chalcone isomerase (Van Tunen et al., *EMBO J.,* 7:1257 (1988), bean glycine rich protein 1 (Keller et al., *EMBO J.,* 8:1309–14 (1989), CaMV 35s transcript (O'Dell et al., *Nature,* 313:810–12 (1985) and Potato patatin (Wenzler et al., *Plant Mol. Biol.,* 12:41–50 (1989). Preferred promoters are the cauliflower mosaic virus (CaMV 35S) promoter and the S-E9 small subunit RuBP carboxylase promoter.

The choice of which expression vector and ultimately to which promoter a polypeptide coding region is operatively linked depends directly on the functional properties desired, e.g. the location and timing of protein expression, and the host cell to be transformed. These are well known limitations inherent in the art of constructing recombinant DNA molecules. However, a vector useful in practicing the present invention is capable of directing the expression of the polypeptide coding region to which it is operatively linked.

Typical vectors useful for expression of genes in higher plants are well known in the art and include vectors derived from the tumor-inducing (Ti) plasmid of *Agrobacterium tumefaciens* described by Rogers et al., *Meth. in Enzymol.,* 153:253–277 (1987). However, several other plant integrating vector systems are known to function in plants including pCaMVCN transfer control vector described by Fromm et al., *Proc. Natl. Acad. Sci. USA,* 82:5824 (1985). Plasmid pCaMVCN (available from Pharmacia, Piscataway, N.J.) includes the cauliflower mosaic virus CaMV 35S promoter.

In preferred embodiments, the vector used to express the polypeptide includes a selection marker that is effective in a plant cell, preferably a drug resistance selection marker. One preferred drug resistance marker is the gene whose expression results in kanamycin resistance; i.e., the chimeric gene containing the nopaline synthase promoter, Tn5 neomycin phosphotransferase II and nopaline synthase 3' nontranslated region described by Rogers et al., in *Methods For Plant Molecular Biology,* A. Weissbach and H. Weissbach, eds., Academic Press Inc., San Diego, Calif. (1988).

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

Means for preparing expression vectors are well known in the art. Expression (transformation vectors) used to transform plants and methods of making those vectors are described in U.S. Pat. Nos. 4,971,908, 4,940,835, 4,761,061 and 4,757,011, the disclosures of which are incorporated herein by reference. Those vectors can be modified to include a coding sequence in accordance with the present invention.

A variety of methods has been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

A coding region that encodes a polypeptide having the ability to catalyze the carboxylation of a biotin carboxyl carrier protein of a cyanobacterium is preferably a biotin carboxylase enzyme of a cyanobacterium, which enzyme is a subunit of acetyl-CoA carboxylase and participates in the carboxylation of acetyl-CoA. In a preferred embodiment, such a polypeptide has the amino acid residue sequence of FIG. 1 or FIG. 2, or a functional equivalent of those sequences. In accordance with such an enbodiment, a coding region comprises the entire DNA sequence of SEQ ID NO:1 (FIG. 1) or the DNA sequence of SEQ ID NO:1 (FIG. 1) from about nucleotide position 1300 to about nucleotide position 2650 or the DNA sequence of SEQ ID NO:5 (FIG. 2).

In another embodiment, an expression vector comprises a coding region of from about 480 to about 40,000 base pairs that encodes a biotin carboxyl carrier protein of a cyanobacterium. That biotin carboxyl carrier protein preferably includes the amino acid residue sequence of FIG. 8 (SEQ ID NO:111) or a functional equivalent thereof. A preferred such coding region includes the DNA sequence of SEQ ID NO:110 (FIG. 8).

In still yet another embodiment, an expression vector comprises a coding region that encodes a plant polypeptide having the ability to catalyze the carboxylation of acetyl-CoA. Such a plant polypeptide is preferably a monocotyledonous or a dicotyledonous plant acetyl-CoA carboxylase enzyme.

A preferred monocotyledonous plant polypeptide encoded by such a coding region is preferably wheat ACC, which ACC includes the amino acid residue sequence of SEQ ID NO:109 (FIG. 6) or a functional equivalent thereof. A preferred coding region includes the DNA sequence of SEQ ID NO:108 (FIG. 6).

III. Polypeptide

The present invention contemplates a polypeptide that defines a whole or a portion of an ACC of a cyanobacterium or a plant. In one embodiment, thus, the present invention provides an isolated polypeptide having the ability to catalyze the carboxylation of a biotin carboxyl carrier protein of a cyanobacterium such as Anabaena or Synechococcus. Preferably, a biotin carboxyl carrier protein includes the amino acid sequence of SEQ ID NO:111 and the polypeptide has FIG. 1 or FIG. 2 (SEQ ID NO:5 and SEQ ID NO:6).

The present invention also contemplates an isolated and purified biotin carboxyl carrier protein of a cyanobacterium such as Anabaena, which protein includes the amino acid residue sequence of SEQ ID NO:111.

In another embodiment, the present invention contemplates an isolated and purified plant polypeptide having a molecular weight of about 220 KD, dimers of which have the ability to catalyze the carboxylation of acetyl-CoA. Such a polypeptide preferably includes the amino acid residue sequence of SEQ ID NO:109.

Modification and changes may be made in the structure of polypeptides of the present invention and still obtain a molecule having like or otherwise desirable characteristics. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a polypeptide that defines that polypeptide's biological functional activity, certain amino acid sequence substitutions can be made in a polypeptide sequence (or, of course, its underlying DNA coding sequence) and nevertheless obtain a polypeptide with like or even counterveiling properties (e.g., antagonistic v. agonistic).

In making such changes, the hydropathic index of amino acids may be considered. The importance of the hydropathic amino acid index in conferring interactive biologic function on a protein is generally understood in the art (Kyte & Doolittle, J. Mol. Biol., 157:105–132, 1982). It is known that certain amino acids may be substituted for other amino acids having a similar hydropathic index or score and still result in a protein with similar biological activity. Each amino acid has been assigned a hydropathic index on the basis of their hydrophobicity and charge characteristsics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, for example, enzymes, substrates, receptors, antibodies, antigens, and the like. It is known in the art that an amino acid may be substituted by another amino acid having a similar hydropathic index and still obtain a biological functionally equivalent protein. In such changes, the substitution of amino acids whose hydropathic indices are within ±2 is preferred, those which are within ±1 are particularly preferred, and those within ±0.5 are even more particularly preferred.

Substitution of like amino acids can also be made on the basis of hydrophilicity, particularly where the biological functional equivalent protein or peptide thereby created is intended for use in immunological embodiments. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been asssigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

The present invention thus contemplates functional equivalents of the polypeptides set forth above. A polypeptide of the present invention is prepared by standard techniques well known to those skilled in the art. Such techniques include, but are not limited to, isolation and purification from tissues known to contain that polypeptide and expression from cloned DNA using transformed cells.

IV. Transformed or transgenic cells or plants

A cyanobacterium, a plant cell or a plant transformed with an expression vector of the present invention is also contemplated. A transgenic cyanobacterium, plant cell or plant derived from such a transformed or transgenic cell is also contemplated.

Means for transforming cyanobacteria are well known in the art. Typically, means of transformation are similar to those well known means used to transform other bacteria such as E. coli. Synethococcus can be transformed simply by incubation of log-phase cells with DNA. (Golden, et al., 1987)

The application of brief, high-voltage electric pulses to a variety of mammalian and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of clones genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

Methods for DNA transformation of plant cells include Agrobacterium-mediated plant transformation, protoplast transformation, gene transfer into pollen, injection into reproductive organs, injection into immature embryos and particle bombardment. Each of these methods has distinct advantages and disadvantages. Thus, one particular method of introducing genes into a particular plant strain may not necessarily be the most effective for another plant strain, but it is well known which methods are useful for a particular plant strain.

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example, the methods described by Fraley et al., *Biotechnology,* 3:629 (1985) and Rogers et al., *Methods in Enzymology,* 153:253–277 (1987). Further, the integration of the Ti-DNA is a relatively precise process resulting in few rearrangements. The region of DNA to be transferred is defined by the border sequences, and intervening DNA is usually inserted into the plant genome as described by Spielmann et al., *Mol. Gen. Genet.,* 205:34 (1986) and Jorgensen et al., *Mol. Gen. Genet.,* 207:471 (1987).

Modern Agrobacterium transformation vectors are capable of replication in *E. coli* as well as Agrobacterium, allowing for convenient manipulations as described by Klee et al., in *Plant DNA Infectious Agents,* T. Hohn and J. Schell, eds., Springer-Verlag, New York (1985) pp. 179–203.

Moreover, recent technological advances in vectors for Agrobacteriun-mediated gene transfer have improved the arrangement of genes and restriction sites in the vectors to facilitate construction of vectors capable of expressing various polypeptide coding genes. The vectors described by Rogers et al., *Methods in Enzymology,* 153:253 (1987), have convenient multi-linker regions flanked by a promoter and a polyadenylation site for direct expression of inserted polypeptide coding genes and are suitable for present purposes. In addition, Agrobacteria containing both armed and disarmed Ti genes can be used for the transformations. In those plant strains where Agrobacterium-mediated transformation is efficient, it is the method of choice because of the facile and defined nature of the gene transfer.

Agrobacterium-mediated transformation of leaf disks and other tissues such as cotyledons and hypocotyls appears to be limited to plants that Agrobacteriun naturally infects. Agrobacterium-mediated transformation is most efficient in dicotyledonous plants. Few monocots appear to be natural hosts for Agrobacterium, although transgenic plants have been produced in asparagus using Agrobacterium vectors as described by Bytebier et al., *Proc. Natl. Acad. Sci. USA,* 84:5345 (1987). Therefore, commercially important cereal grains such as rice, corn, and wheat must usually be transformed using alternative methods. However, as mentioned above, the transformation of asparagus using Agrobacteriun can also be achieved. See, for example, Bytebier, et al., *Proc. Natl. Acad. Sci. USA,* 84:5345 (1987).

A transgenic plant formed using Agrobacterium transformation methods typically contains a single gene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one added gene as here, it is believed that a more accurate name for such a plant is an independent segregant, because the added, exogenous gene segregates independently during mitosis and meiosis.

More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for enhanced carboxylase activity relative to a control (native, non-transgenic) or an independent segregant transgenic plant.

It is to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated.

Transformation of plant protoplasts can be achieved using methods based on calcium phosphate precipitation, polyethylene glycol treatment, electroporation, and combinations of these treatments. See, for example, Potrykus et al., *Mol. Gen. Genet.,* 199:183 (1985); Lorz et al., *Mol. Gen. Genet.,* 199:178 (1985); Fromm et al., *Nature,* 319:791 (1986); Uchimiya et al., *Mol. Gen. Genet.,* 204:204 (1986); Callis et al., *Genes and Development,* 1:1183 (1987); and Marcotte et al., *Nature,* 335:454 (1988).

Application of these systems to different plant strains depends upon the ability to regenerate that particular plant strain from protoplasts. Illustrative methods for the regeneration of cereals from protoplasts are described in Fujimura et al., *Plant Tissue Culture Letters,* 2:74 (1985); Toriyama et al., *Theor Appl. Genet.,* 73:16 (1986); Yamada et al., *Plant Cell Rep.,* 4:85 (1986); Abdullah et al., *Biotechnology,* 4:1087 (1986).

To transform plant strains that cannot be successfully regenerated from protoplasts, other ways to introduce DNA into intact cells or tissues can be utilized. For example, regeneration of cereals from immature embryos or explants can be effected as described by Vasil, *Biotechnology,* 6:397 (1988). In addition, "particle gun" or high-velocity micro-projectile technology can be utilized. (Vasil, 1992)

Using that latter technology, DNA is carried through the cell wall and into the cytoplasm on the surface of small metal particles as described in Klein et al., *Nature,* 327:70 (1987); Klein et al., *Proc. Natl. Acad. Sci. U.S.A.,* 85:8502 (1988); and McCabe et al., *Biotechnology,* 6:923 (1988). The metal particles penetrate through several layers of cells and thus allow the transformation of cells within tissue explants.

Metal particles have been used to successfully transform corn cells and to produce fertile, stable transgenic tobacco plants as described by Gordon-Kamm, W. J. et al., *The Plant Cell,* 2:603–618 (1990); Klein, T. M. et al., *Plant Physiol.,* 91:440–444 (1989); Klein, T. M. et al., *Proc. Natl. Acad. Sci. USA,* 85:8502–8505 (1988); and Tomes, D. T. et al., *Plant Mol. Biol.,* 14:261–268 (1990). Transformation of tissue explants eliminates the need for passage through a protoplast stage and thus speeds the production of transgenic plants.

Thus, the amount of a gene coding for a polypeptide of interest (i.e., a polypeptide having carboxylation activity) can be increased in monocotyledonous plants such as corn by transforming those plants using particle bombardment methods. Maddock et al., *Third International Congress of Plant Molecular Biology,* Abstract 372 (1991). By way of example, an expression vector containing an coding region for a dicotyledonous ACC and an appropriate selectable marker is transformed into a suspension of embryonic maize (corn) cells using a particle gun to deliver the DNA coated on microprojectiles. Transgenic plants are regenerated from transformed embryonic calli that express ACC. Particle bombardment has been used to successfully transform wheat (Vasil et al., 1992).

DNA can also be introduced into plants by direct DNA transfer into pollen as described by Zhou et al., *Methods in Enzymology*, 101:433 (1983); D. Hess, *Intern Rev. Cytol.*, 107:367 (1987); Luo et al., *Plant Mol. Biol. Reporter*, 6:165 (1988). Expression of polypeptide coding genes can be obtained by injection of the DNA into reproductive organs of a plant as described by Pena et al., *Nature*, 325:274 (1987). DNA can also be injected directly into the cells of immature embryos and the rehydration of desiccated embryos as described by Neuhaus et al., *Theor. Appl. Genet.*, 75:30 (1987); and Benbrook et al., in *Proceedings Bio Expo 1986*, Butterworth, Stoneham, Mass., pp. 27–54 (1986).

The development or regeneration of plants from either single plant protoplasts or various explants is well known in the art. See, for example, *Methods for Plant Molecular Biology*, A. Weissbach and H. Weissbach, eds., Academic Press, Inc., San Diego, Calif. (1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by Agrobacterium from leaf explants can be achieved by methods well known in the art such as described by Horsch et al., *Science*, 227:1229–1231 (1985). In this procedure, transformants are cultured in the presence of a selection agent and in a medium that induces the regeneration of Shoots in the plant strain being transformed as described by Fraley et al., *Proc. Natl. Acad. Sci. U.S.A.*, 80:4803 (1983).

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, as discussed before. Otherwise, pollen obtained from the regenerated plants is crossed to seed-grown plants of agronomically important, preferably inbred lines. Conversely, pollen from plants of those important lines is used to pollinate regenerated plants.

A transgenic plant of the present invention containing a desired polypeptide is cultivated using methods well known to one skilled in the art. Any of the transgenic plants of the present invention can be cultivated to isolate the desired ACC or fatty acids which are the products of the series of reactions of which that catalyzed by ACC is the first.

A transgenic plant of this invention thus has an increased amount of an coding region (e.g. gene) that encodes a polypeptide of interest. A preferred transgenic plant is an independent segregant and can transmit that gene and its activity to its progeny. A more preferred transgenic plant is homozygous for that gene, and transmits that gene to all of its offspring on sexual mating.

Seed from a transgenic plant is grown in the field or greenhouse, and resulting sexually mature transgenic plants are self-pollinated to generate true breeding plants. The progeny from these plants become true breeding lines that are evaluated for, by way of example, herbicide resistance, preferably in the field, under a range of environmental conditions.

The commercial value of a transgenic plant with increased herbicide resistance or with altered fatty acid production is enhanced if many different hybrid combinations are available for sale. The user typically grows more than one kind of hybrid based on such differences as time to maturity, standability or other agronomic traits. Additionally, hybrids adapted to one part of a country are not necessarily adapted to another part because of differences in such traits as maturity, disease and herbicide resistance. Because of this, herbicide resistance is preferably bred into a large number of parental lines so that many hybrid combinations can be produced.

V. Process of increasing herbicide resistance

Herbicides such as aryloxyphenoxypropionates and cyclohexanediones inhibit the growth of monocotyledonous weeds by interfering with fatty acid biosynthesis of herbicide sensitive plants. ACC is the target enzyme for those herbicides. Dicotyledonous plants, other eukaryotic organisms and prokaryotic organisms are resistant to those compounds.

Thus, the resistance of sensitive monocotyledonous plants to herbicides can be increased by providing those plants with ACC that is not sensitive to herbicide inhibition. The present invention therefore provides a process of increasing the herbicide resistance of a monocotyledonous plant comprising transforming the plant with a DNA molecule comprising a promoter operatively linked to a coding region that encodes a herbicide resistant polypeptide having the ability to catalyze the carboxylation of acetyl-CoA, which coding region is operatively linked to a transcription-terminating region, whereby the promoter is capable of driving the transcription of the coding region in a monocotyledonous plant.

Preferably, a herbicide resistant polypeptide, a dicotyledonous plant polypeptide such as an acetyl-CoA carboxylase enzyme from soybean, rape, sunflower, tobacco, Arabidopsis, petunia, Canola, pea, bean, tomato, potato, lettuce, spinach, alfalfa, cotton or carrot, or functional equivalent thereof. A promoter and a transcription-terminating region are preferably the same as set forth above.

Transformed monocotyledonous plants can be identified using herbicide resistance. A process for identifying a transformed monocotyledonous plant cell comprises the steps of:

(a) transforming the monocotyledonous plant cell with a DNA molecule that encodes a dicotyledonous acetyl-CoA carboxylase enzyme; and (b) determining the resistance of the plant cell to a herbicide and thereby the identification of the transformed monocotyledonous plant cell.

Means for transforming a monocotyledonous plant cell are the same as set forth above.

The resistance of a transformed plant cell to a herbicide is preferably determined by exposing such a cell to an effective herbicidal dose of a preselected herbicide and maintaining that cell for a period of time and under culture conditions sufficient for the herbicide to inhibit ACC, alter fatty acid biosynthesis or retard growth. The effects of the herbicide can be studied by measuring plant cell ACC activity, fatty acid synthesis or growth.

An effective herbicidal dose of a given herbicide is that amount of the herbicide that retards growth or kills plant cells not containing herbicide-resistant ACC or that amount of a herbicide known to inhibit plant growth. Means for determining an effective herbicidal dose of a given herbicide are well known in the art. Preferably, a herbicide used in such a process is an aryloxyphenoxypropionate or cyclohexanedione herbicide.

VI. Process of altering ACC activity

Acetyl-CoA carboxyase catalyzes the carboxylation of acetyl-CoA. Thus, the carboxylation of acetyl-CoA in a cyanobacterium or a plant can be altered by, for example, increasing an ACC gene copy number or changing the composition (e.g., nucleotide sequence) of an ACC gene. Changes in ACC gene composition can alter gene expression at either the transcriptional or translational level. Alternatively, changes in gene composition can alter ACC function (e.g., activity, binding) by changing primary, secondary or tertiary structure of the enzyme. By way of example, certain changes in ACC structure are associated with changes in the resistance of that altered ACC to herbicides. The copy number of such a gene can be increased by transforming a cyanobacterium or a plant cell with an appropriate expression vector comprising a DNA molecule that encodes ACC.

In one embodiment, therefore, the present invention contemplates a process of altering the carboxylation of acetyl-CoA in a cell comprising transforming the cell with a DNA molecule comprising a promoter operatively linked to a coding region that encodes a polypeptide having the ability to catalyze the carboxylation of acetyl-CoA, which coding region is operatively linked to a transcription-terminating region, whereby the promoter is capable of driving the transcription of the coding region in the cyanobacterium.

In a preferred embodiment, a cell is a cyanobacterium or a plant cell, a polypeptide is a cyanobacterial ACC or a plant ACC. Exemplary and preferred expression vectors for use in such a process are the same as set forth above.

Where a cyanobacterium is transformed with a plant ACC DNA molecule, that cyanobacterium can be used to identify herbicide resistant mutations in the gene encoding ACC. In accordance with such a use, the present invention provides a process for identifying herbicide resistant variants of a plant acetyl-CoA carboxylase comprising the steps of:

(a) transforming cyanobacteria with a DNA molecule that encodes a monocotyledonous plant acetyl-CoA carboxylase enzyme to form transformed or transfected cyanobacteria;

(b) inactivating cyanobacterial acetyl-CoA carboxylase;

(c) exposing the transformed cyanobacteria to an effective herbicidal amount of a herbicide that inhibits acetyl-CoA carboxylase activity;

(d) identifying transformed cyanobacteria that are resistant to the herbicide; and (e) characterizing DNA that encodes acetyl-CoA carboxylase from the cyanobacteria of step (d).

Means for transforming cyanobacteria as well as expression vectors used for such transformation are preferably the same as set forth above. In a preferred embodiment, cyanobacteria are transformed or transfected with an expression vector comprising an coding region that encodes wheat ACC.

Cyanobacteria resistant to the herbicide are identified. Identifying comprises growing or culturing transformed cells in the presence of the herbicide and recovering those cells that survive herbicide exposure.

Transformed, herbicide-resistant cells are then grown in culture, collected and total DNA extracted using standard techniques. ACC DNA is isolated, amplified if needed and then characterized by comparing that DNA with DNA from ACC known to be inhibited by that herbicide.

VII. Process for Determining Herbicide Resistance Inheritibility

In yet another aspect, the present invention provides a process for determining the inheritance of plant resistance to herbicides of the aryloxyphenocypropionate or cyclohexanedione class. That process comprises the steps of:

(a) measuring resistance to herbicides of the aryloxyphenocypropionate or cyclohexanedione class in a parental plant line and in progeny of the parental plant line to;

(b) purifying DNA from the parental plant line and the progeny;

(c) digesting the DNA with restriction enzymes to form DNA fragments;

(d) fractionating the fragments on a gel;

(e) transferring the fragments to a filter support;

(f) annealing the fragments with a labelled RFLP probe consisting of a DNA molecule that encodes acetyl-CoA carboxylase or a portion thereof;

(g) detecting the presence of complexes between the fragments and the RFLP probe; and (h) correlating the herbicide resistance of step (a) with the complexes of step (g) and thereby the inheritance of herbicide resistance.

In a preferred embodiment, the herbicide resistant variant of acetyl-CoA carboxylase is a dicotyledonous plant acetyl-CoA carboxylase enzyme or a portion thereof. In another preferred embodiment, the herbicide resistant variant of acetyl-CoA carboxylase is a mutated monocotyledonous plant acetyl-CoA carboxylase that confers herbicide resistance or a hybrid acetyl-CoA carboxylase comprising a portion of a dicotyledonous plant acetyl-CoA carboxylase, a portion of a dicotyledonous plant acetyl-CoA carboxylase or one or more domains of a cyanobacterial acetyl-CoA carboxylase.

The inheritability of phenotypic traits such as herbicide resistance can be determined using RFLP analysis. Restriction fragment length polymorphisms (RFLPs) are due to sequence differences detectable by lengths of DNA fragments generated by digestion with restriction enzymes and typically revealed by agarose gel electrophoresis. There are large numbers of restriction endonucleases available, characterized by their recognition sequences and source.

Restriction fragment length polymorphism analyses are conducted, for example, by Native Plants Incorporated (NPI). This service is available to the public on a contractual basis. For this analysis, the genetic marker profile of the parental inbred lines is determined. If parental lines are essentially homozygous at all relevant loci (i.e., they should have only one allele at each locus), the diploid genetic marker profile of the hybrid offspring of the inbred parents should be the sum of those parents, e.g., if one parent had the allele A at a particular locus, and the other parent had B, the hybrid AB is by inference.

Probes capable of hybridizing to specific DNA segments under appropriate conditions are prepared using standard techniques well known to those skilled in the art. The probes are labelled with radioactive isotopes or fluorescent dyes for ease of detection. After restriction fragments are separated by size, they are identified by hybridization to the probe. Hybridization with a unique cloned sequence permits the identification of a specific chromosomal region (locus). Because all alleles at a locus are detectable, RFLP's are co-dominant alleles, thereby satisfying a criteria for a genetic marker. They differ from some other types of markers, e.g., from isozymes, in that they reflect the primary DNA sequence, they are not products of transcription or translation. Furthermore, different RFLP profiles result from different arrays of restriction endonucleases.

The foregoing examples illustrate particular embodiments of the present invention. It will be readily apparent to a skilled artisan that changes, modification and alterations can be made to those embodiments without departing from the true scope or spirit of the invention.

EXAMPLE 1

Isolation of Cyanobacterial ACC Polynucleotides

The polynucleotide of SEQ ID NO:1 contains a gene that encodes the enzyme biotin carboxylase (BC) enzyme from the cyanobacterium Anabaena 7120. This gene was cloned from a total DNA extract of Anabaena that was digested with various restriction enzymes, fractionated by gel electrophoresis, and blotted onto GeneScreen Plus (DuPont).

The blot was hybridized at low stringency (1 M NaCl, 57° C.) with a probe consisting of a SstII-PstI fragment containing about 90% of the coding region of the fabG gene from $E.$ $coli$. This probe identified a 3.1-kb HindIII fragment in the Anabaena digest that contained similar sequences. A mixture of about 3-kb HindIII fragments of Anabaena DNA was purified, then digested with NheI, yielding a HindIII-NheI fragment of 1.6 kb that hybridized with the fabG probe. The 1.6-kb region was purified by gel electrophoresis and cloned into pUC18. Plasmid minipreps were made from about 160 colonies, of which four were found to contain the 1.6-kb HindIII-NheI fragment that hybridized with the fabG probe. The 1.6-kb Anabaena fragment was then used as probe to screen, at high stringency (1 M NaCl, 65° C.), a cosmid library of Anabaena DNA inserts averaging 40 kb in size. Five were found among 1920 tested, all of which contained the same size HindIII and NheI fragments as those identified by the $E.$ $coli$ probe previously. From one of the cosmids, the 3.1-kb HindIII fragment containing the Anabaena fabG gene was subcloned into pUC18 and sequenced using the dideoxy chain termination method. The complete nucleotide sequence of this fragment is shown in FIG. 1 (SEQ ID NO:5 and SEQ ID NO:2).

A similar procedure was used to clone the fabG gene from Synechococcus. In this case, the initial Southern hybridization showed that the desired sequences were contained in part on an 0.8-kb BamHI-PstI fragment. This size fragment was purified in two steps and cloned into the plasmid Bluescript KS. Minipreps of plasmids from 200 colonies revealed two that contained the appropriate fragment of Synechococcus DNA. This fragment was used to probe, at high stringency, a library of Synechococcus inserts in the cosmid vector pWB79. One positive clone was found among 1728 tested. This cosmid contained a 2-kb BamHI and a 3-kb PstI fragment that had previously been identified by the $E.$ $coli$ fabG probe in digests of total Synechococcus DNA. Both fragments were subcloned from the cosmid into Bluescript KS and 2.4 kb, including the coding part of the fabG gene, were sequenced. The complete sequence of the coding region of the Anacystis fabG gene is shown in FIG. 2 (SEQ ID NO:5 and SEQ ID NO:6).

EXAMPLE 2

Plant ACC

Figure 5:
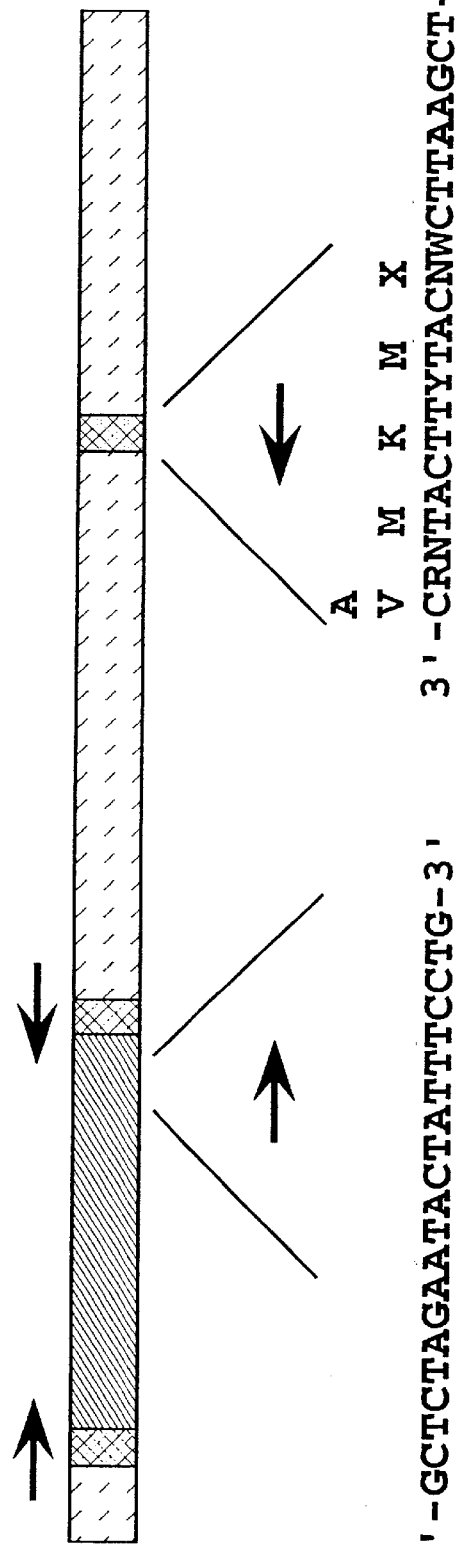
FIG. 5 shows the sequences of the oligonucleotides (SEQ ID NO:114 used and 115) as primers for the PCR used to amplify the region of wheat ACC cDNA between the BC and BCCP domains.

The amino acid sequences of the fabG genes encoding BC from Anabaena and Synechococcus are aligned with sequences of ACC and other biotin-containing enzymes from several sources in FIG. 3. This comparison allows the designation of several areas of significant conservation among all the proteins, indicated by stars in the Figure. Based on this alignment, the sequences shown in FIG. 4 were chosen for the construction of primers for the polymerase chain reaction, in order to amplify the corresponding region of the gene for ACC from wheat. The primers used for this amplification are shown in FIG. 4. Each consists of a 14-nucleotide specific sequence based on the amino acid sequence and an 8-nucleotide extension at the 5'-end of the primer to provide anchors for rounds of amplification after the first round and to provide convenient restriction sites for future analysis and cloning.

cDNA amplification began with a preparation of total polyA-containing mRNA from eight day-old green plants (Triticum aestivum var. Era as described in [Lamppa, et al., 1992]). The first strand of cDNA was synthesized using random hexamers as primers for AMV reverse transcriptase following procedures described in [Haymerle, et al., 1986], with some modifications. Reverse transcriptase was inactivated by incubation at 90° C. and low molecular weight material was removed by filtration through centricon 100. All components of the PCR (from the Cetus/Perkin-Elmer kit) together with the two primers shown in FIG. 4, except the Taq DNA polymerase, were incubated for 3–5 min at 95° C. The PCR was initiated by the addition of polymerase. Conditions were established and optimized using Anabaena DNA as template, in order to provide the best yield and lowest level of non-specific products for amplification of the target BC gene from Anabaena DNA. Amplification was for 45 cycles, each 1 min at 95°, 1 min at 42–46° and 2 min at 72° C. Both the reactions using Anabaena DNA and the single-stranded wheat cDNA as template yielded about 440-bp products. The wheat product was eluted from a gel and reamplified using the same primers. That product, also 440 bp, was cloned into the Invitrogen vector pCR1000 using their A/T tail method, and sequenced. The nucleotide sequence is shown in FIG. 5.

In eukaryotic ACCs, the BCCP domain is located about 300 amino acids away from the end of the BC domain, on the C-terminal side. Therefore, it is possible to amplify the cDNA covering that interval using primers from the C-terminal end of the BC domain and the conserved MKM region of the BCCP. The BC primer was based on the wheat cDNA sequence obtained as described above. These primers, each with 6- or 8-base 5'-extensions, are shown in FIG. 6B.

Figure 7:
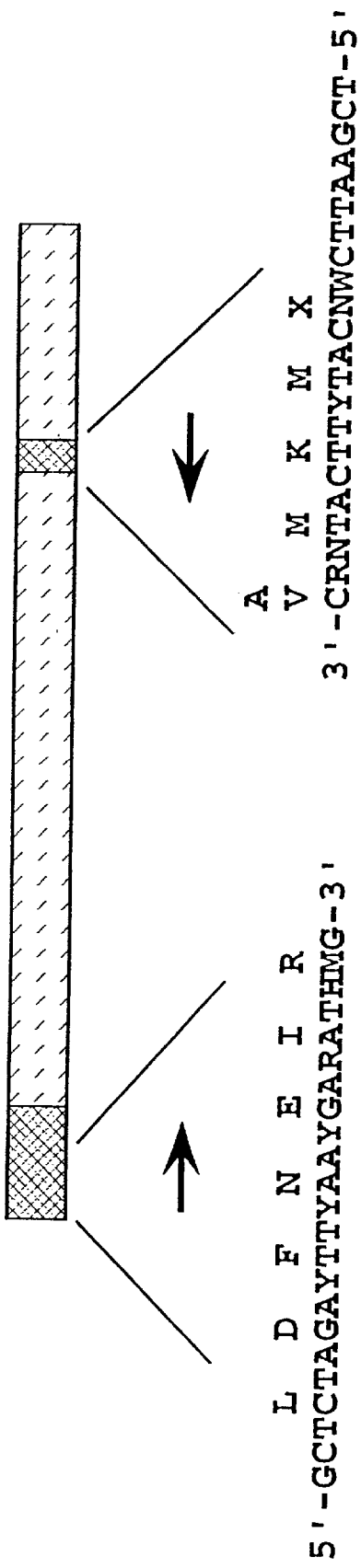
FIG. 7 shows the sequences (SEQ ID NOS:115 and 116) of the oligonucleotides used as primers to amplify most of the fabE gene encoding the biotin carboxyl carrier protein from DNA of Anabaena.

The MKM primer was first checked by determining whether it would amplify the fabE gene encoding BCCP from Anabaena DNA. This PCR was primed at the other end by using a primer based on the N-terminal amino acid sequence, determined on protein purified from Anabaena extracts by affinity chromatography, shown in FIG. 6A. This amplification (using the conditions described above)worked, yielding the correct fragment of the Anabaena fabE gene, whose complete sequence is shown in FIG. 7.

The PCR-amplified fragment of the Anabaena fabE gene was used to identify cosmids (three detected in a library of 1920) that contain the entire fabE gene and flanking DNA. A 4-kb XbaI fragment containing the gene was cloned into the vector Bluescript KS for sequencing. The two primers shown in FIG. 6 were then used to amplify the intervening sequence in wheat cDNA. Again, the product of the first PCR was eluted and reamplified by another round of PCR, then cloned into the Invitrogen vector pCRII. The complete 1.1 kb of the amplified DNA was sequenced, also shown in FIG. 5.

The foregoing examples illustrate particular embodiments of the present invention. One of ordinary skill in the art will readily appreciate that changes, modifications and alterations to those embodiments can be made without departing from the true scope or spirit of the invention.

REFERENCES

The references listed below and all references cited herein are incorporated herein by reference to the extent that they supplement, explain, provide a background for, or teach methodology, techniques, and/or compositions employed herein.

1. J. R. Knowles. 1989. The mechanism of biotin-dependent enzymes. Annu. Rev. Biochem. 58: 195–221.
2. Alix, J.-H. 1989. A rapid procedure for cloning genes from I libraries by complementation of E. coli defective mutants: application to the fabE region of the E. coli chromosome. DNA 8: 779–789.
3. Muramatsu, S., and T. Mizuno. 1989. Nucleotide sequence of the fabE gene and flanking regions containing a bent DNA sequence of Escherichia coli. Nucleic Acids Res. 17: 3982.
4. Li, S., and J. E. Cronan. 1992. The gene encoding the biotin carboxylase subunit of Escherichia coli acetyl-CoA carboxylase. J. Biol. Chem. 267: 855.
5. Lopez-Casillas, F., D. H. Bai, X. Luo, I. S. Kong, M. A. Hermodson, and K. H. Kim. 1988. Structure of the coding sequence and primary amino acid sequence of rat Acetyl-coenzyme A carboxylase. Proc. Natl. Acad. Sci. USA 85: 5784–5788.
6. Takai, T., C. Yokoyama, K. Wada, and T. Tanabe. 1988. Primary structure of chicken liver acetyl-coenzyme A carboxylase deduced from cDNA sequence. J. Biol. Chem. :2651–2657.
   6a. W. A. Feel, S. S. Chirala and S. J. Wakil 1992. Cloning of the yeast FAS3 gene and primary structure of yeast acetyl-CoA carboxylase. Proc Natl Acad, Sci USA 89: 4534–4538.
7. J. L. Harwood. 1988. Fatty acid metabolism. Ann. Rev. Physiol. Plant Mol. Biol. 39: 101–138.
8. Egin-Buhler, B., and J. Ebel. 1983. Improved purification and further characterization of ACC from culture cells of parsley. Eur. J. Biochem. 133: 335–339.
9. Wurtele, E. S. and Nikolau, B. J. 1990. Arch.Biochem..Biophys. 278: 179–186.
10. Slabas, A. R. and Hellyer, A. 1985. Plant Sci. 39: 177–182.
11. Samols, D., C. G. Thornton, V. L. Murtif, G. K. Kumar, F. C. Haase, and H. G. Wood. 1988. Evolutionary conservation among biotin enzymes. J. Biol. Chem. 263: 6461–6464.
12. H. K. Lichtenthaler. 1990. Mode of action of herbicides affecting acetyl-CoA carboxylase and fatty acid biosynthesis. Z. Naturforsch. 45c: 521–528.
13. I. Pecker, D. Chamovitz, H. Linden, G. Sandmann and J. Hirschberg. 1992. A single polypeptide catalyzing the conversion of phytoene to z-carotene is transcriptionally regulated during tomato fruit ripening. Proc Natl Acad Sci USA 89: 4962–4666.
14. G. K. Lamppa, G. Morelli and N-H Chua (1985). Structure and developmental regulation of a wheat gene encoding the major chlorophyll a/b-binding polypeptide. Mol. Cell Biol. 5: 1370–1378.
15. H. Haymerle, J. Herz, G. M. Bressan, R. Frank and K. K. Stanley (1986). Efficient construction of cDNA libraries in plasmid expression vectors using an adaptor strategy. Nucl. Acids Res. 14: 8615–8629.
16. V. Vasil, A. M. Castillo, M. E. Fromm and I. K. Vasil (1992). Herbicide-resistant fertile transgenic wheat plants obtained by microprojectile bombardment of regenerable embryogenic callus. Biotechnology 10: 667–674.
17. S. S. Golden, T. Brusslen and R. Haselkorn (1987), Genetic Enginerring of the Cyanobacterial Chromosome. Methods Enzymology 153: 215–231.

---

What is claimed is:

1. An isolated Anabaena or Synechococcus polypeptide having the ability to catalyze the carboxylation of a biotin carboxyl carrier protein of a cyanobacterium, said polypeptide comprising the amino acid sequence of SEQ ID NO:111 or having an amino acid sequence encoded by the nucleic acid sequence of SEQ ID NO:1 or SEQ ID NO:5'.

2. The polypeptide according to claim 1 wherein said cyanobacterium is Anabaena or Synechococcus.

3. An isolated Anabaena or Synechococcus polypeptide having the ability to catalyze the carboxylation of a biotin carboxyl carrier protein of a cyanobacterium wherein said biotin carboxyl carrier protein comprises the amino acid sequence of SEQ ID NO:111.

4. An isolated Anabaena or Synechococcus polypeptide having the ability to catalyze the carboxylation of a biotin carboxyl carrier protein of a cyanobacterium wherein said polypeptide is encoded by the nucleic acid sequence of SEQ ID NO:1 or SEQ ID NO:5'.

5. The polypeptide according to claim 1 further defined as an Anabaena polypeptide having the ability to catalyze the carboxylation of a biotin carboxyl carrier protein of a cyanobacterium.

6. An isolated Anabaena or Synechococcus polypeptide having the ability to catalyze the carboxylation of a biotin carboxyl carrier protein of a cyanobacterium wherein said polypeptide is further defined as an Anabaena polypeptide encoded by the nucleic acid sequence of SEQ ID NO:1.

7. The polypeptide according to claim 1 further defined as a Synechococcus polypeptide having the ability to catalyze the carboxylation of a biotin carboxyl carrier protein of a cyanobacterium.

8. An isolated Anabaena or Synechococcus polypeptide having the ability to catalyze the carboxylation of a biotin carboxyl carrier protein of a cyanobacterium wherein said polypeptide is further defined as a Synechococcus polypeptide encoded by the nucleic acid sequence of SEQ ID NO:5.

9. A recombinant polypeptide produced by a process comprising expressing the polypeptide encoded by the nucleic acid sequence of SEQ ID NO:1 or SEQ ID NO:5.

10. The recombinant polypeptide of claim 9 further defined as having an amino acid sequence encoded by the nucleic acid sequence of SEQ ID NO:1 or SEQ ID NO:5'.

11. The recombinant polypeptide of claim 9 wherein the nucleic acid sequence is SEQ ID NO:1.

12. The recombinant polypeptide of claim 9 further defined as having the amino acid sequence of SEQ ID NO:6'.

13. The recombinant polypeptide of claim 9 wherein the nucleic acid sequence is SEQ ID NO:5.

* * * * *

SEQUENCE LISTING

<160> NUMBER OF SEQ ID NOS: 128

<210> SEQ ID NO 1
<211> LENGTH: 3065
<212> TYPE: DNA
<213> ORGANISM: Artificial Sequence
<220> FEATURE:
<223> OTHER INFORMATION: Description of Artificial Sequence: Synthetic Primer

<400> SEQUENCE: 1

```
aagcttttat attttgccat ttctagaact tagctgcatc ggccccaagt attttgtcaa      60
atatggcgaa aagacttcat aaatcaaggt taaaggttga ccgtgatgcc aaaacaggta     120
atggcgaccc cagaaaggcc catccacgcc aaaacctaat tgcaaggcct ctgaatttcc     180
gtaataaata ccccgcacat cccgatacaa ctccgtgcga agacgagcta gacttgccca     240
aattggtaat gaacggtttt gcaaatactc gtctacatgg ctggcttccc accatgaggt     300
tgcataggcg agtcgttggc cagagcgtgt acgtagccat acctgtcgcc gcagtcttgg     360
cgctggaaca gattggatta aatccggcgc actatctaaa tccaaaccaa tcaatgacat     420
atcaatgaca tcgacttctg ttggctcacc agtaagtaat tctaaatgcc ttgtgggtga     480
gccatcacct aagagtagta gttgccacgc tggagccagc tgagtgtgag gcaaactatg     540
```

-continued

| | | | | |
|---|---|---|---|---|
| tttaattact | tcttccccac | cttgccaaat | aggagtgagg | cgatgccatc | cggctggcag | 600 |
| tgttgagttg | ttgcttggag | taaaagtggc | agtcaatgtt | ctttacaaaa | gttcacctat | 660 |
| ttatatcaaa | gcataaaaaa | ttaattagtt | gtcagttgtc | attggttatt | cttctttgct | 720 |
| cccctgccc | cctacttccc | tcctctgccc | aataattaga | aaggtcagga | gtcaaaaact | 780 |
| tatcactttt | gaccactgac | ctttcacaat | tgactatagt | cactaaaaaa | tgcggatggc | 840 |
| gagactcgaa | ctcgcaaggc | aaagccacac | gcacctcaag | cgtgcgcgta | taccaattcc | 900 |
| gccacatccg | cacgggttgt | acaagaagat | atactagcac | aaaaaaattg | cataaaacaa | 960 |
| ggtaaaacta | tatttgccaa | actttatgga | aaatttatct | tgctaaatat | acaaatttcc | 1020 |
| cgaagaggat | acgagactaa | cagaaatgta | gtatcgccac | aagtgatatt | aaaggggta | 1080 |
| tgggggtttt | cttcccttac | acccttaaac | cctcacaccc | cacctccatg | aaaaatcttg | 1140 |
| ttggtaagtc | cgtttcctgc | aatttattta | aagatgagcc | tggggtatct | cctgtcataa | 1200 |
| tttgagatga | agcgatgcct | aaggcggcta | cgctacgcgc | taaaagcaac | ttggatggga | 1260 |
| gacaatttct | atctgctggt | actgatactg | atatcgaaaa | ctagaaaatg | aagtttgaca | 1320 |
| aaatattaat | tgccaatcgg | ggagaaatag | cgctgcgcat | tctccgcgcc | tgtgaggaaa | 1380 |
| tggggattgc | gacgatcgca | gttcattcga | ctgttgaccg | gaatgctctt | catgtccaac | 1440 |
| ttgctgacga | agcggtttgt | attggcgaac | ctgctagcgc | taaaagttat | ttgaatattc | 1500 |
| ccaatattat | tgctgcggct | ttaacgcgca | atgccagtgc | tattcatcct | gggtatggct | 1560 |
| ttttatctga | aaatgccaaa | tttgcggaaa | tctgtgctga | ccatcacatt | gcattcattg | 1620 |
| gccccacccc | agaagctatc | cgcctcatgg | gggacaaatc | cactgccaag | gaaaccatgc | 1680 |
| aaaaagctgg | tgtaccgaca | gtaccgggta | gtgaaggttt | ggtagagaca | gagcaagaag | 1740 |
| gattagaact | ggcgaaagat | attggctacc | cagtgatgat | caaagccacg | gctggtggtg | 1800 |
| gcggccgggg | tatgcgactg | gtgcgatcgc | cagatgaatt | tgtcaaactg | ttcttagccg | 1860 |
| cccaaggtga | agctggtgca | gcctttggta | atgctggcgt | ttatatagaa | aaatttattg | 1920 |
| aacgtccgcg | ccacattgaa | tttcaaattt | tgctgataa | ttacggcaat | gtgattcact | 1980 |
| tgggtgagag | ggattgctca | attcagcgtc | gtaaccaaaa | gttactagaa | gaagcccca | 2040 |
| gcccagcctt | ggactcagac | ctaagggaaa | aaatgggaca | agcggcggtg | aaagcggctc | 2100 |
| agtttatcaa | ttacgccggg | gcaggtacta | tcgagttttt | gctagataga | tccggtcagt | 2160 |
| tttactttat | ggagatgaac | acccggattc | aagtagaaca | tcccgtaact | gagatggtta | 2220 |
| ctggagtgga | tttattggtt | gagcaaatca | gaattgccca | aggggaaaga | cttagactaa | 2280 |
| ctcaagacca | agtagtttta | cgcggtcatg | cgatcgaatg | tcgcatcaat | gccgaagacc | 2340 |
| cagaccacga | tttccgccca | gcacccggac | gcattagcgg | ttatcttccc | cctggcggcc | 2400 |
| ctggcgtgcg | gattgactcc | cacgtttaca | cggattacca | aattccgccc | tactacgatt | 2460 |
| ccttaattgg | taaattgatc | gtttggggcc | ctgatcgcgc | tactgctatt | aaccgcatga | 2520 |
| aacgcgccct | cagggaatgc | gccatcactg | gattacctac | aaccattggg | tttcatcaaa | 2580 |
| gaattatgga | aaatccccaa | tttttacaag | gtaatgtgtc | tactagtttt | gtgcaggaga | 2640 |
| tgaataaata | gggtaatggg | taatgggtaa | tgggtaatag | agtttcaatc | accaattacc | 2700 |
| aattccctaa | ctcatccgtg | ccaacatcgt | cagtaatcct | tgctggccta | aagaacttc | 2760 |
| tcgcaacagg | ctaaaaatac | caacacacac | aatgggggtg | atatcaacac | cacctattgg | 2820 |
| tgggatgatt | tttcgcaagg | gaatgagaaa | tggttcagtc | ggccaagcaa | ttaagttgaa | 2880 |
| gggcaaacgg | ttcagatcga | cttgcggata | ccaggtcaga | atgatacgga | aaataaacag | 2940 |

-continued

```
aaatgtcatc actcccaata cagggccaag aatccaaacg ctcaggttaa caccagtcat    3000
cgatctaagc tactattttg tgaatttaca aaaaactgca agcaaaagct gaaaatttta    3060
agctt                                                                3065
```

<210> SEQ ID NO 2
<211> LENGTH: 32
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 2

Asp Glu Ala Met Pro Lys Ala Ala Thr Leu Arg Ala Lys Ser Asn Leu
 1               5                  10                  15

Asp Gly Arg Gln Phe Leu Ser Ala Gly Thr Asp Thr Asp Ile Glu Asn
            20                  25                  30

<210> SEQ ID NO 3
<211> LENGTH: 427
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 3

Lys Met Lys Phe Asp Lys Ile Leu Ile Ala Asn Arg Gly Glu Ile Ala
 1               5                  10                  15

Leu Arg Ile Leu Arg Ala Cys Glu Glu Met Gly Ile Ala Thr Ile Ala
            20                  25                  30

Val His Ser Thr Val Asp Arg Asn Ala Leu His Val Gln Leu Ala Asp
        35                  40                  45

Glu Ala Val Cys Ile Gly Glu Pro Ala Ser Ala Lys Ser Tyr Leu Asn
    50                  55                  60

Ile Pro Asn Ile Ile Ala Ala Leu Thr Arg Asn Ala Ser Ala Ile
 65                  70                  75                  80

His Pro Gly Tyr Gly Phe Leu Ser Glu Asn Ala Lys Phe Ala Glu Ile
                85                  90                  95

Cys Ala Asp His His Ile Ala Phe Ile Gly Pro Thr Pro Glu Ala Ile
            100                 105                 110

Arg Leu Met Gly Asp Lys Ser Thr Ala Lys Glu Thr Met Gln Lys Ala
        115                 120                 125

Gly Val Pro Thr Val Pro Gly Ser Glu Gly Leu Val Glu Thr Glu Gln
    130                 135                 140

Glu Gly Leu Glu Leu Ala Lys Asp Ile Gly Tyr Pro Val Met Ile Lys
145                 150                 155                 160

Ala Thr Ala Gly Gly Gly Gly Arg Gly Met Arg Leu Val Arg Ser Pro
                165                 170                 175

Asp Glu Phe Val Lys Leu Phe Leu Ala Ala Gln Gly Glu Ala Gly Ala
            180                 185                 190

Ala Phe Gly Asn Ala Gly Val Tyr Ile Glu Lys Phe Ile Glu Arg Pro
        195                 200                 205

Arg His Ile Glu Phe Gln Ile Leu Ala Asp Asn Tyr Gly Asn Val Ile
    210                 215                 220

His Leu Glu Arg Asp Cys Ser Ile Gln Arg Arg Asn Gln Lys Leu Leu
225                 230                 235                 240

-continued

```
Glu Glu Ala Pro Ser Pro Ala Leu Asp Ser Asp Leu Arg Glu Lys Met
                245                 250                 255

Gly Gln Ala Ala Val Lys Ala Ala Gln Phe Ile Asn Tyr Ala Gly Ala
            260                 265                 270

Gly Thr Ile Glu Phe Leu Leu Asp Arg Ser Gly Gln Phe Gly Val Asp
        275                 280                 285

Leu Leu Val Glu Gln Ile Arg Ile Ala Gln Gly Glu Arg Leu Arg Leu
    290                 295                 300

Thr Gln Asp Gln Val Val Leu Arg Gly His Ala Ile Glu Cys Arg Ile
305                 310                 315                 320

Asn Ala Glu Asp Pro Asp His Asp Phe Arg Pro Ala Pro Gly Arg Ile
                325                 330                 335

Ser Gly Tyr Leu Pro Pro Gly Gly Pro Gly Val Arg Ile Asp Ser His
            340                 345                 350

Val Tyr Thr Asp Tyr Gln Ile Pro Pro Tyr Tyr Asp Ser Leu Ile Gly
        355                 360                 365

Lys Leu Ile Val Trp Gly Pro Asp Arg Ala Thr Ala Ile Asn Arg Met
    370                 375                 380

Lys Arg Ala Leu Arg Glu Cys Ala Ile Thr Gly Leu Pro Thr Thr Ile
385                 390                 395                 400

Gly Phe His Gln Arg Ile Met Glu Asn Pro Gln Phe Leu Gln Gly Asn
                405                 410                 415

Val Ser Thr Ser Phe Val Gln Glu Met Asn Lys
            420                 425
```

<210> SEQ ID NO 4
<211> LENGTH: 36
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

```
Trp Val Met Gly Asn Arg Val Ser Ile Thr Asn Tyr Gln Phe Pro Asn
  1               5                  10                  15

Ser Ser Val Pro Thr Ser Ser Val Ile Leu Ala Gly Leu Glu Glu Leu
            20                  25                  30

Leu Ala Thr Gly
        35
```

<210> SEQ ID NO 5
<211> LENGTH: 1362
<212> TYPE: DNA
<213> ORGANISM: Artificial Sequence
<220> FEATURE:
<223> OTHER INFORMATION: Description of Artificial Sequence: Synthetic

<400> SEQUENCE: 5

```
atgcgtttca acaagatcct gatcgccaat cgcggcgaaa tcgccctgcg cattctccgc    60
acttgtcaag aactcgggat cggcacgatc gccgttcact ccactgtgga tcgcaacgcg   120
ctccatgtgc agttagcgga cgaagcggtc tgtattggcg aagcggccag cagcaaaagc   180
tatctcaata tccccaacat cattgcggcg ccctgaccc taatgccag cgccattcac   240 cccggctatg gcttcttggc ggagaatgcc cgctttgcag aaatctgcgc cgatcaccat   300
ctcaccttta ttggccccag ccccgattcg attcgagcca tgggcgataa atccaccgct   360
aaggaaacaa tgcagcgggt cggcgttccg acgattccgg gcagtgacgg tctgctgacg   420
```

-continued

```
gatgttgatt cggctgccaa agttgctgcc gagatcggct atcccgtcat gatcaaagcg      480
acggcggggg gcggtggtcg cggtatgcgg ctggtgcgtg accctgcaga tctggaaaaa      540
ctgttccttg ctgcccaagg agaagccgag gcagcttttg ggaatccagg actgtatctc      600
gaaaaattta tcgatcgccc acgccacgtt gaatttcaga tcttggccga tgcctacggc      660
aatgtagtgc atctaggcga gcgcgattgc tccattcaac gtcgtcacca aaagctgctc      720
gaagaagccc ccagtccggc gctatcggca gacctgcggc agaaaatggg cgatgccgcc      780
gtcaaagtcg ctcaagcgat cggctacatc ggtgccggca ccgtggagtt tctggtcgat      840
gcgaccggca acttctactt catggagatg aatacccgca tccaagtcga gcatccagtc      900
acagaaatga ttacgggact ggacttgatt gcggagcaga ttcggattgc caaggcgaa      960 gcgctgcgct tccggcaagc cgatattcaa ctgcgcggcc atgcgatcga atgccgtatc     1020
aatgcggaag atccggaata caatttccgg ccgaatcctg ccgcattac aggctattta     1080 ccgcccggcg gccccggcgt tcgtgtcgat tcccatgttt ataccgacta cgaaattccg     1140
ccctattacg attcgctgat tggcaaattg attgtctggg gtgcaacacg ggaagaggcg     1200
atcgcgcgga tgcagcgtgc tctgcgggaa tgcgccatca ccggcttgcc gacgaccctt     1260
agtttccatc agctgatgtt gcagatgcct gagttcctgc gcggggaact ctataccaac     1320
tttgttgagc aggtgatgct acctcggatc ctcaagtcct ag                        1362
```

<210> SEQ ID NO 6
<211> LENGTH: 453
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 6

```
Met Arg Phe Asn Lys Ile Leu Ile Ala Asn Arg Gly Glu Ile Ala Leu
  1               5                  10                  15

Arg Ile Leu Arg Thr Cys Glu Glu Leu Gly Ile Gly Thr Ile Ala Val
                 20                  25                  30

His Ser Thr Val Asp Arg Asn Ala Leu His Val Gln Leu Ala Asp Glu
             35                  40                  45

Ala Val Cys Ile Gly Glu Ala Ala Ser Ser Lys Ser Tyr Leu Asn Ile
         50                  55                  60

Pro Asn Ile Ile Ala Ala Leu Thr Arg Asn Ala Ser Ala Ile His
 65                  70                  75                  80

Pro Gly Tyr Gly Phe Leu Ala Glu Asn Ala Arg Phe Ala Glu Ile Cys
                 85                  90                  95

Ala Asp His His Leu Thr Phe Ile Gly Pro Ser Pro Asp Ser Ile Arg
            100                 105                 110

Ala Met Gly Asp Lys Ser Thr Ala Lys Glu Thr Met Gln Arg Val Gly
        115                 120                 125

Val Pro Thr Ile Pro Gly Ser Asp Gly Leu Leu Thr Asp Val Asp Ser
    130                 135                 140

Ala Ala Lys Val Ala Ala Glu Ile Gly Tyr Pro Val Met Ile Lys Ala
145                 150                 155                 160

Thr Ala Gly Gly Gly Gly Arg Gly Met Arg Leu Val Arg Glu Pro Ala
                165                 170                 175

Asp Leu Glu Lys Leu Phe Leu Ala Ala Gln Gly Glu Ala Glu Ala Ala
            180                 185                 190
```

```
Phe Gly Asn Pro Gly Leu Tyr Leu Glu Lys Phe Ile Asp Arg Pro Arg
        195                 200                 205

His Val Glu Phe Gln Ile Leu Ala Asp Ala Tyr Gly Asn Val Val Glu
    210                 215                 220

Leu Gly Glu Arg Asp Cys Ser Ile Gln Arg Arg His Gln Lys Leu Leu
225                 230                 235                 240

Glu Glu Ala Pro Ser Pro Ala Leu Ser Ala Asp Leu Arg Gln Lys Met
                245                 250                 255

Gly Asp Ala Ala Val Lys Val Ala Gln Ala Ile Gly Tyr Ile Gly Ala
            260                 265                 270

Gly Thr Val Glu Phe Leu Val Asp Ala Thr Gly Asn Phe Tyr Phe Met
        275                 280                 285

Glu Met Asn Thr Arg Ile Gln Val Glu His Pro Val Thr Glu Met Ile
    290                 295                 300

Thr Gly Leu Asp Leu Ile Ala Glu Gln Ile Arg Ile Ala Gln Gly Glu
305                 310                 315                 320

Ala Leu Arg Phe Arg Gln Ala Asp Ile Gln Leu Arg Gly His Ala Ile
                325                 330                 335

Glu Cys Arg Ile Asn Ala Glu Asp Pro Glu Tyr Asn Phe Arg Pro Asn
            340                 345                 350

Pro Gly Arg Ile Thr Gly Tyr Leu Pro Pro Gly Gly Pro Gly Val Arg
        355                 360                 365

Val Asp Ser His Val Tyr Thr Asp Tyr Glu Ile Pro Pro Tyr Tyr Asp
370                 375                 380

Ser Leu Ile Gly Lys Leu Ile Val Trp Gly Ala Thr Arg Glu Glu Ala
385                 390                 395                 400

Ile Ala Arg Met Gln Arg Ala Leu Arg Glu Gly Ala Ile Thr Gly Leu
                405                 410                 415

Pro Thr Thr Leu Ser Phe His Gln Leu Met Leu Gln Met Pro Glu Phe
            420                 425                 430

Leu Arg Gly Glu Leu Tyr Thr Asn Phe Val Glu Gln Val Met Leu Pro
        435                 440                 445

Arg Ile Leu Lys Ser
    450

<210> SEQ ID NO 7
<211> LENGTH: 34
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 7

Met Asp Glu Pro Ser Pro Leu Ala Lys Thr Leu Glu Leu Asn Gln His
  1               5                  10                  15

Ser Arg Phe Ile Ile Gly Ser Val Ser Glu Asp Asn Ser Glu Asp Glu
                20                  25                  30

Ile Ser

<210> SEQ ID NO 8
<211> LENGTH: 187
<212> TYPE: PRT
<213> ORGANISM: Artificial Sequence
<220> FEATURE:
<223> OTHER INFORMATION: Description of Artificial Sequence:  Synthetic
      Peptide
```

```
<400> SEQUENCE: 8

Asn Leu Val Lys Leu Asp Leu Glu Glu Lys Glu Gly Ser Leu Ser Pro
  1               5                  10                  15

Ala Ser Val Ser Ser Asp Thr Leu Ser Asp Leu Gly Ile Ser Ala Leu
             20                  25                  30

Gln Asp Gly Leu Ala Phe His Met Arg Ser Ser Met Ser Gly Leu His
         35                  40                  45

Leu Val Lys Gln Gly Arg Asp Arg Lys Lys Ile Asp Ser Gln Arg Asp
     50                  55                  60

Phe Thr Val Ala Ser Pro Ala Glu Phe Val Thr Arg Phe Gly Gly Asn
 65                  70                  75                  80

Lys Val Ile Glu Lys Val Leu Ile Ala Asn Asn Gly Ile Ala Ala Val
                 85                  90                  95

Lys Cys Met Arg Ser Ile Arg Arg Trp Ser Tyr Glu Met Phe Arg Asn
            100                 105                 110

Glu Arg Ala Ile Arg Phe Val Val Met Val Thr Pro Glu Asp Leu Lys
        115                 120                 125

Ala Asn Ala Glu Tyr Ile Lys Met Ala Asp His Tyr Val Pro Val Pro
    130                 135                 140

Gly Gly Ala Asn Asn Asn Tyr Ala Asn Val Glu Leu Ile Leu Asp
145                 150                 155                 160

Ile Ala Lys Arg Ile Pro Val Gln Ala Val Trp Ala Gly Trp Gly His
                165                 170                 175

Ala Ser Glu Asn Pro Lys Leu Pro Glu Leu Leu
            180                 185

<210> SEQ ID NO 9
<211> LENGTH: 122
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 9

Leu Lys Asn Gly Ile Ala Phe Met Gly Pro Pro Ser Gln Ala Met Trp
  1               5                  10                  15

Ala Leu Gly Asp Lys Ile Ala Ser Ser Ile Val Ala Gln Thr Ala Gly
             20                  25                  30

Ile Pro Thr Leu Pro Trp Ser Gly Ser Gly Leu Arg Val Asp Trp Gln
         35                  40                  45

Glu Asn Asp Phe Ser Lys Arg Ile Leu Asn Val Pro Gln Asp Leu Tyr
     50                  55                  60

Glu Lys Gly Tyr Val Lys Asp Val Asp Gly Leu Lys Ala Ala Glu
 65                  70                  75                  80

Glu Val Gly Tyr Pro Val Met Ile Lys Ala Ser Glu Gly Gly Gly Gly
                 85                  90                  95

Lys Gly Ile Arg Lys Val Asn Asn Ala Asp Asp Phe Pro Asn Leu Phe
            100                 105                 110

Arg Gln Val Gln Ala Glu Val Pro Gly Ser
        115                 120

<210> SEQ ID NO 10
<211> LENGTH: 86
<212> TYPE: PRT
<213> ORGANISM: Artificial Sequence
<220> FEATURE:
```

```
<223> OTHER INFORMATION: Description of Artificial Sequence:  Synthetic
      Peptide

<400> SEQUENCE: 10

Pro Ile Phe Val Met Arg Leu Ala Lys Gln Ser Arg His Leu Glu Val
 1               5                  10                  15

Gln Ile Leu Ala Asp Gln Tyr Gly Asn Ala Ile Ser Leu Phe Gly Arg
             20                  25                  30

Asp Cys Ser Val Gln Arg Arg His Gln Lys Ile Ile Glu Glu Ala Pro
         35                  40                  45

Ala Ala Ile Ala Thr Pro Ala Val Phe Glu His Met Glu Gln Cys Ala
     50                  55                  60

Val Lys Leu Ala Lys Met Val Gly Tyr Val Ser Ala Gly Thr Val Glu
 65                  70                  75                  80

Tyr Leu Tyr Ser Gln Asp
                 85

<210> SEQ ID NO 11
<211> LENGTH: 70
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 11

Gly Ser Phe Tyr Phe Leu Glu Leu Asn Pro Arg Leu Gln Val Glu His
 1               5                  10                  15

Pro Cys Thr Glu Met Val Ala Asp Val Asn Leu Pro Ala Ala Gln Leu
             20                  25                  30

Gln Ile Ala Met Gly Ile Pro Leu Phe Arg Ile Lys Asp Ile Arg Met
         35                  40                  45

Met Tyr Gly Val Ser Pro Trp Gly Asp Ala Pro Ile Asp Phe Glu Asn
     50                  55                  60

Ser Ala His Val Pro Cys
 65                  70

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 12

Pro Arg Gly His Val Ile Ala Ala Arg Ile Thr Ser Glu Asn Pro Asp
 1               5                  10                  15

Glu Gly Phe Lys
             20

<210> SEQ ID NO 13
<211> LENGTH: 21
<212> TYPE: PRT
<213> ORGANISM: Artificial Sequence
<220> FEATURE:
<223> OTHER INFORMATION: Description of Artificial Sequence:  Synthetic
      Peptide
```

```
<400> SEQUENCE: 13

Pro Ser Ser Gly Thr Val Gln Glu Leu Asn Phe Arg Ser Asn Lys Asn
 1               5                  10                  15

Val Trp Gly Tyr Phe
            20

<210> SEQ ID NO 14
<211> LENGTH: 122
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 14

Ser Val Ala Ala Ala Gly Gly Leu His Glu Phe Ala Asp Ser Gln Phe
 1               5                  10                  15

Gly His Cys Phe Ser Trp Gly Glu Asn Arg Glu Glu Ala Ile Ser Asn
            20                  25                  30

Met Val Val Ala Leu Lys Glu Leu Ser Ile Arg Gly Asp Phe Arg Thr
        35                  40                  45

Thr Val Glu Tyr Leu Ile Lys Leu Leu Glu Thr Glu Ser Phe Gln Leu
    50                  55                  60

Asn Arg Ile Asp Thr Gly Trp Leu Asp Arg Leu Ile Ala Glu Lys Val
65                  70                  75                  80

Gln Ala Glu Arg Pro Asp Thr Met Leu Gly Val Val Cys Gly Ala Leu
                85                  90                  95

His Val Ala Asp Val Asn Leu Arg Asn Ser Ile Ser Asn Phe Leu His
            100                 105                 110

Ser Leu Glu Arg Gly Gln Val Leu Pro Ala
        115                 120

<210> SEQ ID NO 15
<211> LENGTH: 190
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 15

His Thr Leu Leu Asn Thr Val Asp Val Glu Leu Ile Tyr Glu Gly Ile
 1               5                  10                  15

Lys Tyr Val Leu Lys Val Thr Arg Gln Ser Pro Asn Ser Tyr Val Val
            20                  25                  30

Ile Met Asn Gly Ser Cys Val Glu Val Asp Val His Arg Leu Ser Asp
        35                  40                  45

Gly Gly Leu Leu Leu Ser Tyr Asp Gly Ser Ser Tyr Thr Thr Tyr Met
    50                  55                  60

Lys Glu Glu Val Asp Arg Tyr Arg Ile Thr Ile Gly Asn Lys Thr Cys
65                  70                  75                  80

Val Phe Glu Lys Glu Asn Asp Pro Ser Val Met Arg Ser Pro Ser Ala
                85                  90                  95

Gly Lys Leu Ile Gln Tyr Ile Val Glu Asp Gly Gly His Val Phe Ala
            100                 105                 110

Gly Gln Cys Tyr Ala Glu Ile Glu Val Met Lys Met Val Met Thr Leu
        115                 120                 125
```

```
Thr Ala Val Glu Ser Gly Cys Ile His Tyr Val Lys Arg Pro Gly Ala
            130                 135                 140

Ala Leu Asp Pro Gly Cys Val Ile Ala Lys Met Gln Leu Asp Asn Pro
145                 150                 155                 160

Ser Lys Val Gln Gln Ala Glu Leu His Thr Gly Ser Leu Pro Gln Ile
                165                 170                 175

Gln Ser Thr Ala Leu Arg Gly Glu Lys Leu His Arg Ile Phe
            180                 185                 190

<210> SEQ ID NO 16
<211> LENGTH: 37
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 16

Val Met Ile Lys Ala Ser Trp Gly Gly Gly Lys Gly Ile Arg Lys
  1               5                  10                  15

Val His Asn Asp Asp Glu Val Arg Ala Leu Phe Lys Gln Val Gln Gly
                 20                  25                  30

Glu Val Pro Gly Ser
            35

<210> SEQ ID NO 17
<211> LENGTH: 187
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 17

Pro Ile Phe Ile Met Lys Val Ala Ser Gln Ser Arg His Leu Glu Val
  1               5                  10                  15

Gln Leu Leu Cys Asp Lys His Gly Asn Val Ala Ala Leu His Ser Arg
                 20                  25                  30

Asp Cys Ser Val Gln Arg Arg His Gln Lys Ile Ile Glu Glu Gly Pro
             35                  40                  45

Ile Thr Val Ala Pro Pro Glu Thr Ile Lys Glu Leu Glu Gln Ala Ala
     50                  55                  60

Arg Arg Leu Ala Lys Cys Val Gln Tyr Gln Gly Ala Ala Thr Val Glu
 65                  70                  75                  80

Tyr Leu Tyr Ser Met Glu Thr Gly Glu Tyr Tyr Phe Leu Glu Leu Asn
                 85                  90                  95

Pro Arg Leu Gln Val Glu His Pro Val Thr Glu Trp Ile Ala Glu Ile
            100                 105                 110

Asn Leu Pro Ala Ser Gln Val Val Val Gly Met Gly Ile Pro Leu Tyr
        115                 120                 125

Asn Ile Pro Glu Ile Arg Arg Phe Tyr Gly Ile Glu His Gly Gly Gly
    130                 135                 140

Tyr His Ala Trp Lys Glu Ile Ser Ala Val Ala Thr Lys Phe Asp Leu
145                 150                 155                 160

Asp Lys Ala Gln Ser Val Lys Pro Lys Gly His Cys Val Ala Val Arg
                165                 170                 175

Val Thr Ser Glu Asp Pro Asp Asp Gly Phe Lys
            180                 185
```

```
<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 18

Pro Thr Ser Gly Arg Val Glu Glu Leu Asn Phe Lys Ser Lys Pro Asn
  1               5                  10                  15

Val Trp Ala Tyr Phe
            20

<210> SEQ ID NO 19
<211> LENGTH: 122
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 19

Ser Val Lys Ser Gly Gly Ala Ile His Glu Phe Ser Asp Ser Gln Phe
  1               5                  10                  15

Gly His Val Phe Ala Phe Gly Glu Ser Arg Ser Leu Ala Ile Ala Asn
             20                  25                  30

Met Val Leu Gly Leu Lys Glu Ile Gln Ile Arg Gly Glu Ile Arg Thr
         35                  40                  45

Asn Val Asp Tyr Thr Val Asp Leu Leu Asn Ala Ala Glu Tyr Arg Glu
     50                  55                  60

Asn Met Ile His Thr Gly Trp Leu Asp Ser Arg Ile Ala Met Arg Val
 65                  70                  75                  80

Arg Ala Glu Arg Pro Pro Trp Tyr Leu Ser Val Val Gly Gly Ala Leu
                 85                  90                  95

Tyr Glu Ala Ser Ser Arg Ser Ser Val Val Thr Asp Tyr Val Gly
            100                 105                 110

Tyr Leu Ser Lys Gly Gln Ile Pro Pro Lys
            115                 120

<210> SEQ ID NO 20
<211> LENGTH: 124
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 20

His Ile Ser Leu Val Asn Leu Thr Val Thr Leu Asn Ile Asp Gly Ser
  1               5                  10                  15

Lys Tyr Thr Ile Glu Thr Val Arg Gly Gly Pro Arg Ser Tyr Lys Leu
             20                  25                  30

Arg Ile Asn Glu Ser Glu Val Glu Ala Glu Ile His Phe Leu Arg Asp
         35                  40                  45

Gly Gly Leu Leu Met Gln Leu Asp Gly Asn Ser His Val Ile Tyr Ala
     50                  55                  60

Glu Thr Glu Ala Ala Gly Thr Arg Leu Leu Ile Asn Gly Arg Thr Cys
 65                  70                  75                  80

Leu Leu Gln Lys Glu His Asp Pro Ser Arg Leu Leu Ala Asp Thr Pro
                 85                  90                  95
```

```
Cys Lys Leu Leu Arg Phe Leu Val Ala Asp Gly Ser His Val Val Ala
            100                 105                 110
Asp Thr Pro Tyr Ala Glu Val Glu Ala Met Lys Met
        115                 120
```

<210> SEQ ID NO 21
<211> LENGTH: 222
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 21

```
Met Glu Glu Ser Ser Gln Pro Ala Lys Pro Leu Glu Met Asn Pro His
 1               5                  10                  15

Ser Arg Phe Ile Ile Gly Ser Val Ser Glu Asp Asn Ser Glu Asp Glu
            20                  25                  30

Thr Ser Ser Leu Val Lys Leu Asp Leu Leu Glu Glu Lys Glu Arg Ser
        35                  40                  45

Leu Ser Pro Val Ser Val Cys Ser Asp Ser Leu Ser Asp Leu Gly Leu
    50                  55                  60

Pro Ser Ala Gln Asp Gly Leu Ala Asn His Met Arg Pro Ser Met Ser
65                  70                  75                  80

Gly Leu His Leu Val Lys Gln Gly Arg Asp Arg Lys Lys Val Asp Val
                85                  90                  95

Gln Arg Asp Phe Thr Val Ala Ser Pro Ala Glu Phe Val Thr Arg Phe
            100                 105                 110

Gly Gly Asn Arg Val Ile Glu Lys Val Leu Ile Ala Asn Asn Gly Ile
        115                 120                 125

Ala Ala Val Lys Cys Met Arg Ser Ile Arg Arg Trp Ser Tyr Glu Met
130                 135                 140

Phe Arg Asn Glu Arg Ala Ile Arg Phe Val Val Met Val Thr Pro Glu
145                 150                 155                 160

Asp Leu Lys Ala Asn Ala Glu Tyr Ile Lys Met Ala Asp His Tyr Val
                165                 170                 175

Pro Val Pro Gly Gly Pro Asn Asn Asn Tyr Ala Asn Val Glu Leu
            180                 185                 190

Ile Leu Asp Ile Ala Lys Arg Ile Pro Val Gln Ala Val Trp Ala Gly
        195                 200                 205

Trp Gly His Ala Ser Glu Asn Pro Lys Leu Pro Glu Leu Leu
    210                 215                 220
```

<210> SEQ ID NO 22
<211> LENGTH: 122
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 22

```
His Lys Asn Gly Ile Ala Phe Met Gly Pro Pro Ser Gln Ala Met Trp
 1               5                  10                  15

Ala Leu Gly Asp Lys Ile Ala Ser Ser Ile Val Ala Gln Thr Ala Gly
            20                  25                  30

Ile Pro Thr Leu Pro Trp Asn Gly Ser Gly Leu Arg Val Asp Trp Gln
        35                  40                  45
```

```
Glu Asn Asp Leu Gln Lys Arg Ile Leu Asn Val Pro Gln Glu Leu Tyr
 50                  55                  60

Glu Lys Gly Tyr Val Lys Asp Ala Asp Gly Leu Arg Ala Ala Glu
 65                  70                  75                  80

Glu Val Gly Tyr Pro Val Met Ile Lys Ala Ser Glu Gly Gly Gly
                 85                  90                  95

Lys Gly Ile Arg Lys Val Asn Asn Ala Asp Asp Phe Pro Asn Leu Phe
            100                 105                 110

Arg Gln Val Gln Ala Glu Val Pro Gly Ser
        115                 120
```

<210> SEQ ID NO 23
<211> LENGTH: 95
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 23

```
Pro Ile Phe Val Met Arg Leu Ala Lys Gln Ser Arg His Leu Glu Val
 1               5                  10                  15

Gln Ile Leu Ala Asp Gln Tyr Gly Asn Ala Ile Ser Leu Phe Gly Arg
            20                  25                  30

Asp Cys Ser Val Gln Arg Arg His Gln Lys Ile Ile Glu Glu Ala Gly
        35                  40                  45

Leu Arg Ala Ala Glu Glu Val Gly Tyr Pro Val Met Ile Lys Ala Ser
 50                  55                  60

Glu Gly Gly Gly Gly Lys Gly Ile Arg Lys Val Asn Asn Ala Asp Asp
 65                  70                  75                  80

Phe Pro Asn Leu Phe Arg Gln Val Gln Ala Glu Val Pro Gly Ser
                 85                  90                  95
```

<210> SEQ ID NO 24
<211> LENGTH: 86
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 24

```
Pro Ile Phe Val Met Arg Leu Ala Lys Gln Ser Arg His Leu Glu Val
 1               5                  10                  15

Gln Ile Leu Ala Asp Gln Tyr Gly Asn Ala Ile Ser Leu Phe Gly Arg
            20                  25                  30

Asp Cys Ser Val Gln Arg Arg His Gln Lys Ile Ile Glu Glu Ala Pro
        35                  40                  45

Ala Ser Ile Ala Thr Ser Val Val Phe Glu His Met Glu Gln Cys Ala
 50                  55                  60

Val Lys Leu Ala Lys Met Val Gly Tyr Val Ser Ala Gly Thr Val Glu
 65                  70                  75                  80

Tyr Leu Tyr Ser Gln Asp
                 85
```

<210> SEQ ID NO 25
<211> LENGTH: 70
<212> TYPE: PRT
<213> ORGANISM: Artificial Sequence
<220> FEATURE:

<223> OTHER INFORMATION: Description of Artificial Sequence: Synthetic
      Peptide

<400> SEQUENCE: 25

Gly Ser Phe Tyr Phe Leu Glu Leu Asn Pro Arg Leu Gln Val Glu His
 1               5                  10                  15

Pro Cys Thr Glu Met Val Ala Asp Val Asn Leu Pro Ala Ala Gln Leu
                20                  25                  30

Gln Ile Ala Met Gly Ile Pro Leu His Arg Ile Lys Asp Ile Arg Val
            35                  40                  45

Met Tyr Gly Val Ser Pro Trp Gly Asp Gly Ser Ile Asp Phe Glu Asn
        50                  55                  60

Ser Ala His Val Pro Cys
 65                  70

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 26

Pro Arg Gly His Val Ile Ala Ala Arg Ile Thr Ser Glu Asn Pro Asp
 1               5                  10                  15

Glu Gly Phe Lys
            20

<210> SEQ ID NO 27
<211> LENGTH: 21
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 27

Pro Ser Ser Gly Thr Val Gln Glu Leu Asn Phe Arg Ser Asn Lys Asn
 1               5                  10                  15

Val Trp Gly Tyr Phe
            20

<210> SEQ ID NO 28
<211> LENGTH: 122
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 28

Ser Val Ala Ala Ala Gly Gly Leu His Glu Phe Ala Asp Ser Gln Phe
 1               5                  10                  15

Gly His Cys Phe Ser Trp Gly Glu Asn Arg Glu Ala Ile Ser Asn
                20                  25                  30

Met Val Ala Leu Lys Glu Leu Ser Ile Arg Gly Asp Phe Arg Thr
            35                  40                  45

Thr Val Glu Tyr Leu Ile Lys Leu Leu Glu Thr Glu Ser Phe Gln Gln
        50                  55                  60

Asn Arg Ile Asp Thr Gly Trp Leu Asp Arg Leu Ile Ala Glu Lys Val
 65                  70                  75                  80

```
Gln Ala Glu Arg Pro Asp Thr Met Leu Gly Val Val Cys Gly Ala Leu
                 85                  90                  95

His Val Ala Asp Val Ser Phe Arg Asn Ser Val Ser Asn Phe Leu His
            100                 105                 110

Ser Leu Glu Arg Gly Gln Val Leu Pro Ala
        115                 120

<210> SEQ ID NO 29
<211> LENGTH: 90
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 29

Met Val Val Ala Leu Lys Glu Leu Ser Ile Arg Gly Asp Phe Arg Thr
  1               5                  10                  15

Thr Val Glu Tyr Leu Ile Lys Leu Leu Glu Thr Glu Ser Phe Gln Gln
             20                  25                  30

Asn Arg Ile Asp Thr Gly Trp Leu Asp Arg Leu Ile Ala Glu Lys Val
         35                  40                  45

Gln Ala Glu Arg Pro Asp Thr Met Leu Gly Val Val Cys Gly Ala Leu
     50                  55                  60

His Val Ala Asp Val Ser Phe Arg Asn Ser Val Ser Asn Phe Leu His
 65                  70                  75                  80

Ser Leu Glu Arg Gly Gln Val Leu Pro Ala
             85                  90

<210> SEQ ID NO 30
<211> LENGTH: 190
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 30

His Thr Leu Leu Asn Thr Val Asp Val Glu Leu Ile Tyr Glu Gly Arg
  1               5                  10                  15

Lys Tyr Val Leu Lys Val Thr Arg Gln Ser Pro Asn Ser Tyr Val Val
             20                  25                  30

Ile Met Asn Ser Ser Cys Val Glu Val Asp Val His Arg Leu Ser Asp
             35                  40                  45

Gly Gly Leu Leu Leu Ser Tyr Asp Gly Ser Ser Tyr Thr Thr Tyr Met
     50                  55                  60

Lys Glu Glu Val Asp Arg Tyr Arg Ile Thr Ile Gly Asn Lys Thr Cys
 65                  70                  75                  80

Val Phe Glu Lys Glu Asn Asp Pro Ser Ile Leu Arg Ser Pro Ser Ala
             85                  90                  95

Gly Lys Leu Ile Gln Tyr Val Val Glu Asp Gly Gly His Val Phe Ala
            100                 105                 110

Gly Gln Cys Phe Ala Glu Ile Glu Val Met Lys Met Val Met Thr Leu
            115                 120                 125

Thr Ala Gly Glu Ser Gly Cys Ile His Tyr Val Lys Arg Pro Gly Ala
        130                 135                 140

Val Leu Asp Pro Gly Cys Val Ile Ala Lys Leu Gln Leu Asp Asp Pro
145                 150                 155                 160
```

Ser Arg Val Gln Gln Ala Glu Leu His Thr Gly Thr Leu Pro Gln Ile
            165                 170                 175

Gln Ser Thr Ala Leu Arg Gly Glu Lys Leu His Arg Ile Phe
        180                 185                 190

<210> SEQ ID NO 31
<211> LENGTH: 41
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 31

Met Ser Glu Glu Ser Leu Phe Glu Ser Ser Pro Gln Lys Met Glu Tyr
 1               5                  10                  15

Glu Ile Thr Asn Tyr Ser Glu Arg His Thr Glu Leu Pro Gly His Phe
            20                  25                  30

Ile Gly Leu Asn Thr Val Asp Lys Leu
        35                  40

<210> SEQ ID NO 32
<211> LENGTH: 74
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 32

Ala Asp Val Asp Ala Val Trp Ala Gly Trp Gly His Ala Ser Glu Asn
 1               5                  10                  15

Pro Leu Leu Pro Glu Lys Leu Ser Gln Ser Lys Arg Lys Val Ile Phe
            20                  25                  30

Ile Gly Pro Pro Gly Asn Ala Met Arg Ser Leu Gly Asp Lys Ile Ser
        35                  40                  45

Ser Thr Thr Ile Val Ala Gln Ser Ala Lys Val Pro Cys Ile Pro Trp
    50                  55                  60

Ser Gly Thr Thr Gly Val Asp Thr Val His
 65                 70

<210> SEQ ID NO 33
<211> LENGTH: 73
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 33

Val Asp Glu Lys Thr Gly Leu Val Ser Val Asp Asp Ile Tyr Gln
 1               5                  10                  15

Lys Gly Cys Cys Thr Ser Pro Glu Asp Gly Leu Gln Lys Ala Lys Arg
            20                  25                  30

Ile Gly Phe Pro Val Met Ile Lys Ala Ser Glu Gly Gly Gly Gly Lys
        35                  40                  45

Gly Ile Arg Gln Val Glu Arg Glu Glu Asp Phe Ile Ala Leu Tyr His
    50                  55                  60

Gln Ala Ala Asn Glu Ile Pro Gly Ser
 65                 70

```
<210> SEQ ID NO 34
<211> LENGTH: 157
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 34

Pro Ile Phe Ile Met Lys Leu Ala Gly Arg Ala Arg His Leu Glu Val
 1               5                  10                  15

Gln Leu Leu Ala Asp Gln Tyr Gly Thr Asn Ile Ser Leu Phe Gly Arg
                20                  25                  30

Asp Cys Ser Val Gln Arg Arg His Gln Lys Ile Ile Glu Glu Ala Pro
            35                  40                  45

Val Thr Ile Ala Lys Ala Glu Thr Phe His Glu Met Glu Lys Ala Ala
        50                  55                  60

Val Arg Leu Gly Lys Leu Val Gly Tyr Val Ser Ala Gly Thr Val Glu
 65                  70                  75                  80

Tyr Leu Tyr Ser His Asp Asp Gly Lys Phe Tyr Phe Leu Glu Leu Asn
                85                  90                  95

Pro Arg Leu Gln Val Glu His Pro Thr Thr Glu Met Val Ser Gly Val
                100                 105                 110

Asn Leu Pro Ala Ala Gln Leu Gln Ile Ala Met Gly Ile Pro Met His
            115                 120                 125

Arg Ile Ser Asp Ile Arg Thr Leu Tyr Gly Met Asn Pro His Ser Ala
        130                 135                 140

Ser Glu Ile Asp Phe Glu Phe Lys Thr Gln Asp Ala Thr
145                 150                 155

<210> SEQ ID NO 35
<211> LENGTH: 27
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 35

Lys Lys Gln Arg Arg Pro Ile Pro Lys Gly His Cys Thr Ala Cys Arg
 1               5                  10                  15

Ile Thr Ser Glu Asp Pro Asn Asp Gly Phe Lys
                20                  25

<210> SEQ ID NO 36
<211> LENGTH: 21
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 36

Pro Ser Gly Gly Thr Leu His Glu Leu Asn Phe Arg Ser Ser Ser Asn
 1               5                  10                  15

Val Trp Gly Tyr Phe
                20

<210> SEQ ID NO 37
<211> LENGTH: 122
<212> TYPE: PRT
<213> ORGANISM: Artificial Sequence
```

```
<220> FEATURE:
<223> OTHER INFORMATION: Description of Artificial Sequence: Synthetic
      Peptide

<400> SEQUENCE: 37

Ser Val Gly Asn Asn Gly Asn Ile His Ser Phe Ser Asp Ser Gln Phe
  1               5                  10                  15

Gly His Ile Phe Ala Phe Gly Glu Asn Arg Gln Ala Ser Arg Lys His
             20                  25                  30

Met Val Val Ala Leu Lys Glu Leu Ser Ile Arg Gly Asp Phe Arg Thr
         35                  40                  45

Thr Val Glu Tyr Leu Ile Lys Leu Leu Glu Thr Glu Asp Phe Glu Asp
     50                  55                  60

Asn Thr Ile Thr Thr Gly Trp Leu Asp Asp Leu Ile Thr His Lys Met
 65                  70                  75                  80

Thr Ala Glu Lys Pro Asp Pro Thr Leu Ala Val Ile Cys Gly Ala Ala
                 85                  90                  95

Thr Lys Ala Phe Leu Ala Ser Glu Glu Ala Arg His Lys Tyr Ile Glu
            100                 105                 110

Ser Leu Gln Lys Gly Gln Val Leu Ser Lys
            115                 120

<210> SEQ ID NO 38
<211> LENGTH: 190
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 38

Asp Leu Leu Gln Thr Met Phe Pro Val Asp Phe Ile His Glu Gly Lys
  1               5                  10                  15

Arg Tyr Lys Phe Thr Val Ala Lys Ser Gly Asn Asp Arg Tyr Thr Leu
             20                  25                  30

Phe Ile Asn Gly Ser Lys Cys Asp Ile Ile Leu Arg Gln Leu Ser Asp
         35                  40                  45

Gly Gly Leu Leu Ile Ala Ile Gly Gly Lys Ser His Thr Ile Tyr Trp
     50                  55                  60

Lys Glu Glu Val Ala Ala Thr Arg Leu Ser Val Asp Ser Met Thr Thr
 65                  70                  75                  80

Leu Leu Glu Val Glu Asn Asp Pro Thr Gln Leu Arg Thr Pro Ser Pro
                 85                  90                  95

Gly Lys Leu Val Lys Phe Leu Val Glu Asn Gly Glu His Ile Ile Lys
            100                 105                 110

Gly Gln Pro Tyr Ala Glu Ile Glu Val Met Lys Met Gln Met Pro Leu
            115                 120                 125

Val Ser Gln Glu Asn Gly Ile Val Gln Leu Leu Lys Gln Pro Gly Ser
        130                 135                 140

Thr Ile Val Ala Gly Asp Ile Met Ala Ile Met Thr Leu Asp Asp Pro
145                 150                 155                 160

Ser Lys Val Lys His Ala Leu Pro Phe Glu Gly Met Leu Pro Asp Phe
                165                 170                 175

Gly Ser Pro Val Ile Glu Gly Thr Lys Pro Ala Tyr Lys Phe
            180                 185                 190
```

```
<210> SEQ ID NO 39
<211> LENGTH: 37
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 39

Met Arg Phe Asn Lys Ile Leu Ile Ala Asn Arg Gly Glu Ile Ala Leu
 1               5                  10                  15

Arg Ile Leu Arg Thr Cys Glu Glu Leu Gly Ile Gly Thr Ile Ala Val
             20                  25                  30

His Ser Thr Val Asp
         35

<210> SEQ ID NO 40
<211> LENGTH: 21
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 40

Arg Asn Ala Leu His Val Gln Leu Ala Asp Glu Ala Val Cys Ile Gly
 1               5                  10                  15

Glu Ala Ala Ser Ser
             20

<210> SEQ ID NO 41
<211> LENGTH: 38
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 41

Lys Ser Tyr Leu Asn Ile Pro Asn Ile Ile Ala Ala Ala Leu Thr Arg
 1               5                  10                  15

Asn Ala Ser Ala Ile His Pro Gly Tyr Gly Phe Leu Ala Glu Asn Ala
             20                  25                  30

Arg Phe Ala Glu Ile Cys
         35

<210> SEQ ID NO 42
<211> LENGTH: 41
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 42

Ala Asp His His Leu Thr Phe Ile Gly Pro Ser Pro Asp Ser Ile Arg
 1               5                  10                  15

Ala Met Gly Asp Lys Ser Thr Ala Lys Glu Thr Met Gln Arg Val Gly
             20                  25                  30

Val Pro Thr Ile Pro Gly Ser Asp Gly
         35                  40

<210> SEQ ID NO 43
<211> LENGTH: 143
```

```
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 43

Leu Leu Thr Asp Val Asp Ser Ala Ala Lys Val Ala Ala Glu Ile Gly
  1               5                  10                  15

Tyr Pro Val Met Ile Lys Ala Thr Ala Gly Gly Gly Arg Gly Met
             20                  25                  30

Arg Leu Val Arg Glu Pro Ala Asp Leu Glu Lys Leu Phe Leu Ala Ala
             35                  40                  45

Gln Gly Glu Ala Glu Ala Ala Phe Gly Asn Pro Gly Leu Tyr Leu Glu
     50                  55                  60

Lys Phe Ile Asp Arg Pro Arg His Val Glu Phe Gln Ile Leu Ala Asp
 65                  70                  75                  80

Ala Tyr Gly Asn Val Val His Leu Gly Glu Arg Asp Cys Ser Ile Gln
                 85                  90                  95

Arg Arg His Gln Lys Leu Leu Glu Glu Ala Pro Ser Pro Ala Leu Ser
            100                 105                 110

Ala Asp Leu Arg Gln Lys Met Gly Asp Ala Ala Val Lys Val Ala Gln
            115                 120                 125

Ala Ile Gly Tyr Ile Gly Ala Gly Thr Val Glu Phe Leu Val Asp
            130                 135                 140

<210> SEQ ID NO 44
<211> LENGTH: 50
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 44

Ala Thr Gly Asn Phe Tyr Phe Met Glu Met Asn Thr Arg Ile Gln Val
  1               5                  10                  15

Glu His Pro Val Thr Glu Met Ile Thr Gly Leu Asp Leu Ile Ala Glu
             20                  25                  30

Gln Ile Arg Ile Ala Gln Gly Glu Ala Leu Arg Phe Arg Gln Ala Asp
             35                  40                  45

Ile Gln
     50

<210> SEQ ID NO 45
<211> LENGTH: 19
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 45

Leu Arg Gly His Ala Ile Glu Cys Arg Ile Asn Ala Glu Asp Pro Glu
  1               5                  10                  15

Tyr Asn Phe

<210> SEQ ID NO 46
<211> LENGTH: 9
<212> TYPE: PRT
<213> ORGANISM: Artificial Sequence
```

```
<220> FEATURE:
<223> OTHER INFORMATION: Description of Artificial Sequence:  Synthetic
      Peptide

<400> SEQUENCE: 46

Arg Pro Asn Pro Gly Arg Ile Thr Gly
  1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 47

Pro Gly Val Arg Val Asp Ser
  1               5

<210> SEQ ID NO 48
<211> LENGTH: 44
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 48

His Val Tyr Thr Asp Tyr Glu Ile Pro Pro Tyr Tyr Asp Ser Leu Ile
  1               5                  10                  15

Gly Lys Leu Ile Val Trp Gly Ala Thr Arg Glu Glu Ala Ile Ala Arg
                 20                  25                  30

Met Gln Arg Ala Leu Arg Glu Cys Ala Ile Thr Gly
             35                  40

<210> SEQ ID NO 49
<211> LENGTH: 38
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 49

Leu Pro Thr Thr Leu Ser Phe His Gln Leu Met Leu Gln Met Pro Glu
  1               5                  10                  15

Phe Leu Arg Gly Glu Leu Tyr Thr Asn Phe Val Glu Gln Val Met Leu
                 20                  25                  30

Pro Arg Ile Leu Lys Ser
             35

<210> SEQ ID NO 50
<211> LENGTH: 37
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 50

Met Lys Phe Asp Lys Ile Leu Ile Ala Asn Arg Gly Glu Ile Ala Leu
  1               5                  10                  15

Arg Ile Leu Arg Ala Cys Glu Glu Met Gly Ile Ala Thr Ile Ala Val
                 20                  25                  30
```

```
His Ser Thr Val Asp
        35

<210> SEQ ID NO 51
<211> LENGTH: 21
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 51

Arg Asn Ala Leu His Val Gln Leu Ala Asp Glu Ala Val Cys Ile Gly
  1               5                  10                  15

Glu Pro Ala Ser Ala
            20

<210> SEQ ID NO 52
<211> LENGTH: 38
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 52

Lys Ser Tyr Leu Asn Ile Pro Asn Ile Ile Ala Ala Ala Leu Thr Arg
  1               5                  10                  15

Asn Ala Ser Ala Ile His Pro Gly Tyr Gly Phe Leu Ser Glu Asn Ala
             20                  25                  30

Lys Phe Ala Glu Ile Cys
         35

<210> SEQ ID NO 53
<211> LENGTH: 42
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 53

Ala Asp His His Ile Ala Phe Ile Gly Pro Thr Pro Glu Ala Ile Arg
  1               5                  10                  15

Leu Met Gly Asp Lys Ser Thr Ala Lys Glu Thr Met Gln Lys Ala Gly
             20                  25                  30

Val Pro Thr Val Pro Gly Ser Glu Gly Leu
             35                  40

<210> SEQ ID NO 54
<211> LENGTH: 142
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 54

Val Glu Thr Glu Gln Glu Gly Leu Glu Leu Ala Lys Asp Ile Gly Tyr
  1               5                  10                  15

Pro Val Met Ile Lys Ala Thr Ala Gly Gly Gly Gly Arg Gly Met Arg
             20                  25                  30

Leu Val Arg Ser Pro Asp Glu Phe Val Lys Leu Phe Leu Ala Ala Gln
             35                  40                  45
```

```
Gly Glu Ala Gly Ala Ala Phe Gly Asn Ala Val Tyr Ile Glu Lys
            50                  55                  60

Phe Ile Glu Arg Pro Arg His Ile Glu Phe Gln Ile Leu Ala Asp Asn
 65                  70                  75                  80

Tyr Gly Asn Val Ile His Leu Gly Arg Asp Cys Ser Ile Gln Arg
                 85                  90                  95

Arg Asn Gln Lys Leu Leu Glu Gly Ala Pro Ser Pro Ala Leu Asp Ser
                100                 105                 110

Asp Leu Arg Glu Lys Met Gly Gln Ala Ala Val Lys Ala Ala Gln Phe
                115                 120                 125

Ile Asn Tyr Ala Gly Ala Gly Thr Ile Glu Phe Leu Leu Asp
                130                 135                 140

<210> SEQ ID NO 55
<211> LENGTH: 50
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 55

Arg Ser Gly Gln Phe Tyr Phe Met Glu Met Asn Thr Arg Ile Gln Val
  1               5                  10                  15

Glu His Pro Val Thr Glu Met Val Thr Gly Val Asp Leu Leu Val Glu
                 20                  25                  30

Gln Ile Arg Ile Ala Gln Gly Glu Arg Leu Arg Leu Thr Gln Asp Gln
             35                  40                  45

Val Val
     50

<210> SEQ ID NO 56
<211> LENGTH: 19
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 56

Leu Arg Gly His Ala Ile Glu Cys Arg Ile Asn Ala Glu Asp Pro Asp
  1               5                  10                  15

His Asp Phe

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 57

Arg Pro Ala Pro Gly Arg Ile Ser Gly
  1               5

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence:  Synthetic
      Peptide
```

```
<400> SEQUENCE: 58

Tyr Leu Pro Pro Gly Gly
 1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 59

Pro Gly Val Arg Ile Asp Ser
 1               5

<210> SEQ ID NO 60
<211> LENGTH: 44
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 60

His Val Tyr Thr Asp Tyr Gln Ile Pro Pro Tyr Tyr Asp Ser Leu Ile
 1               5                  10                  15

Gly Lys Leu Ile Val Trp Gly Pro Asp Arg Ala Thr Ala Ile Asn Arg
             20                  25                  30

Met Lys Arg Ala Leu Arg Glu Cys Ala Ile Thr Gly
         35                  40

<210> SEQ ID NO 61
<211> LENGTH: 154
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 61

Leu Pro Thr Thr Ile Gly Phe His Gln Arg Ile Met Glu Asn Pro Gln
 1               5                  10                  15

Phe Leu Gln Gly Asn Val Ser Thr Ser Phe Val Gln Glu Met Asn Lys
             20                  25                  30

Pro Leu Asp Phe Asn Glu Ile Arg Gln Leu Leu Thr Thr Ile Ala Gln
         35                  40                  45

Thr Asp Ile Ala Glu Val Thr Leu Lys Ser Asp Phe Glu Leu Thr
     50                  55                  60

Val Arg Lys Ala Val Gly Val Asn Asn Ser Val Val Pro Val Val Thr
 65                  70                  75                  80

Ala Pro Leu Ser Gly Val Val Gly Ser Gly Leu Pro Ser Ala Ile Pro
                 85                  90                  95

Ile Val Ala His Ala Ala Pro Ser Pro Ser Pro Glu Pro Gly Thr Ser
                100                 105                 110

Arg Ala Ala Asp His Ala Val Thr Ser Ser Gly Ser Gln Pro Gly Ala
            115                 120                 125

Lys Ile Ile Asp Gln Lys Leu Ala Glu Val Ala Ser Pro Met Val Gly
        130                 135                 140

Thr Phe Tyr Arg Ala Pro Ala Pro Gly Glu
145                 150
```

<210> SEQ ID NO 62
<211> LENGTH: 24
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 62

Ala Val Phe Val Glu Val Gly Asp Arg Ile Arg Gln Gly Gln Thr Val
 1               5                  10                  15

Cys Ile Ile Glu Ala Met Lys Met
             20

<210> SEQ ID NO 63
<211> LENGTH: 36
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 63

Met Leu Asp Lys Ile Val Ile Ala Asn Arg Gly Glu Ile Ala Leu Arg
 1               5                  10                  15

Ile Leu Arg Ala Cys Lys Glu Leu Gly Ile Lys Thr Val Ala Val His
             20                  25                  30

Ser Ser Ala Asp
         35

<210> SEQ ID NO 64
<211> LENGTH: 21
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 64

Arg Asp Leu Lys His Val Leu Leu Ala Asp Glu Thr Val Cys Ile Gly
 1               5                  10                  15

Pro Ala Pro Ser Val
             20

<210> SEQ ID NO 65
<211> LENGTH: 38
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 65

Lys Ser Tyr Leu Asn Ile Pro Ala Ile Ile Ser Ala Ala Glu Ile Thr
 1               5                  10                  15

Gly Ala Val Ala Ile His Pro Gly Tyr Gly Phe Leu Ser Glu Asn Ala
             20                  25                  30

Asn Phe Ala Glu Gln Val
         35

<210> SEQ ID NO 66
<211> LENGTH: 43
<212> TYPE: PRT
<213> ORGANISM: Artificial Sequence
<220> FEATURE:

```
<223> OTHER INFORMATION: Description of Artificial Sequence: Synthetic
      Peptide

<400> SEQUENCE: 66

Glu Arg Ser Gly Phe Ile Phe Ile Gly Pro Lys Ala Glu Thr Ile Arg
  1               5                  10                  15

Leu Met Gly Asp Lys Val Ser Ala Ile Ala Ala Met Lys Lys Ala Gly
             20                  25                  30

Val Pro Cys Val Pro Gly Ser Asp Gly Pro Leu
         35                  40

<210> SEQ ID NO 67
<211> LENGTH: 141
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 67

Gly Asp Asp Met Asp Lys Asn Arg Ala Ile Ala Lys Arg Ile Gly Tyr
  1               5                  10                  15

Pro Val Ile Ile Lys Ala Ser Gly Gly Gly Gly Arg Gly Met Arg
             20                  25                  30

Val Val Arg Gly Asp Ala Glu Leu Ala Gln Ser Ile Ser Met Thr Arg
             35                  40                  45

Ala Glu Ala Lys Ala Ala Phe Ser Asn Asp Met Val Tyr Met Glu Lys
         50                  55                  60

Tyr Leu Glu Asn Pro Arg His Val Glu Ile Gln Val Leu Ala Asp Gly
 65                  70                  75                  80

Gln Gly Asn Ala Ile Tyr Leu Ala Glu Arg Asp Cys Ser Met Gln Arg
                 85                  90                  95

Arg His Gln Lys Val Val Glu Ala Pro Ala Pro Gly Ile Thr Pro
            100                 105                 110

Glu Leu Arg Arg Tyr Ile Gly Glu Arg Cys Ala Lys Ala Cys Val Asp
            115                 120                 125

Ile Gly Tyr Arg Gly Ala Gly Thr Phe Glu Phe Leu Phe
            130                 135                 140

<210> SEQ ID NO 68
<211> LENGTH: 50
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 68

Glu Asn Gly Glu Phe Tyr Phe Ile Glu Met Asn Thr Arg Ile Gln Val
  1               5                  10                  15

Glu His Pro Val Thr Glu Met Ile Thr Gly Val Asp Leu Ile Lys Glu
             20                  25                  30

Gln Met Arg Ile Ala Ala Gly Gln Pro Leu Ser Ile Lys Gln Glu Glu
         35                  40                  45

Val His
     50

<210> SEQ ID NO 69
<211> LENGTH: 25
<212> TYPE: PRT
```

<213> ORGANISM: Artificial Sequence
<220> FEATURE:
<223> OTHER INFORMATION: Description of Artificial Sequence: Synthetic
      Peptide

<400> SEQUENCE: 69

Val Arg Gly His Ala Val Glu Cys Arg Ile Asn Ala Glu Asp Pro Asn
 1               5                  10                  15

Leu Pro Ser Pro Gly Lys Ile Thr Arg
            20                  25

<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 70

Phe His Ala Pro Gly Gly
 1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 71

Phe Gly Val Arg Trp Glu Ser
 1               5

<210> SEQ ID NO 72
<211> LENGTH: 44
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 72

His Ile Tyr Ala Gly Tyr Thr Val Pro Pro Tyr Tyr Asp Ser Met Ile
 1               5                  10                  15

Gly Lys Leu Ile Cys Tyr Gly Glu Asn Arg Asp Val Ala Ile Ala Arg
            20                  25                  30

Met Lys Asn Ala Leu Gln Glu Leu Ile Ile Asp Gly
        35                  40

<210> SEQ ID NO 73
<211> LENGTH: 135
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 73

Ile Lys Thr Asn Val Asp Leu Gln Ile Arg Ile Met Asn Asp Glu Asn
 1               5                  10                  15

Phe Gln His Gly Gly Thr Asn Ile His Tyr Leu Glu Lys Lys Leu Gly
            20                  25                  30

```
Leu Gln Glu Lys Met Asp Ile Arg Lys Ile Lys Lys Leu Ile Glu Leu
         35                  40                  45

Val Glu Glu Ser Gly Ile Ser Glu Leu Glu Ile Ser Glu Gly Glu Glu
     50                  55                  60

Ser Val Arg Ile Ser Arg Ala Ala Pro Ala Ala Ser Phe Pro Val Met
 65                  70                  75                  80

Gln Gln Ala Tyr Ala Ala Pro Met Met Gln Gln Pro Ala Gln Ser Asn
                 85                  90                  95

Ala Ala Ala Pro Ala Thr Val Pro Ser Met Glu Ala Pro Ala Ala Ala
                100                 105                 110

Glu Ile Ser Gly His Ile Val Arg Ser Pro Met Val Gly Thr Phe Tyr
                115                 120                 125

Arg Thr Pro Ser Pro Asp Ala
                130                 135

<210> SEQ ID NO 74
<211> LENGTH: 57
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 74

Lys Ala Phe Ile Glu Val Gly Gln Lys Val Asn Val Gly Asp Thr Leu
 1               5                  10                  15

Cys Ile Val Glu Ala Met Lys Met Met Asn Gln Ile Glu Ala Asp Lys
                 20                  25                  30

Ser Gly Thr Val Lys Ala Ile Leu Val Glu Ser Gly Gln Pro Val Glu
             35                  40                  45

Phe Asp Glu Pro Leu Val Val Ile Glu
         50                  55

<210> SEQ ID NO 75
<211> LENGTH: 72
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 75

Met Leu Ser Ala Ala Leu Arg Thr Leu Lys His Val Leu Tyr Tyr Ser
 1               5                  10                  15

Arg Gln Cys Leu Met Val Ser Arg Asn Leu Gly Ser Val Gly Tyr Asp
                 20                  25                  30

Pro Asn Glu Lys Thr Phe Asp Lys Ile Leu Val Ala Asn Arg Gly Glu
             35                  40                  45

Ile Ala Cys Arg Val Ile Arg Thr Cys Lys Lys Met Gly Ile Lys Thr
         50                  55                  60

Val Ala Ile His Ser Asp Val Asp
 65                  70

<210> SEQ ID NO 76
<211> LENGTH: 21
<212> TYPE: PRT
<213> ORGANISM: Artificial Sequence
<220> FEATURE:
<223> OTHER INFORMATION: Description of Artificial Sequence: Synthetic
      Peptide
```

```
<400> SEQUENCE: 76

Ala Ser Ser Val His Val Lys Met Ala Asp Glu Ala Val Cys Val Gly
 1               5                  10                  15

Pro Ala Pro Thr Ser
            20

<210> SEQ ID NO 77
<211> LENGTH: 38
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 77

Lys Ser Tyr Leu Asn Met Asp Ala Ile Met Glu Ala Ile Lys Lys Thr
 1               5                  10                  15

Arg Ala Gln Ala Val His Pro Gly Tyr Gly Phe Leu Ser Glu Asn Lys
            20                  25                  30

Glu Phe Ala Arg Cys Leu
            35

<210> SEQ ID NO 78
<211> LENGTH: 41
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 78

Ala Ala Glu Asp Val Val Phe Ile Gly Pro Asp Thr His Ala Ile Gln
 1               5                  10                  15

Ala Met Gly Asp Lys Ile Glu Ser Lys Leu Leu Ala Lys Ala Glu
            20                  25                  30

Val Asn Thr Ile Pro Gly Phe Asp Gly
            35                  40

<210> SEQ ID NO 79
<211> LENGTH: 144
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 79

Val Lys Asp Ala Glu Glu Ala Val Arg Ile Ala Arg Glu Ile Gly Tyr
 1               5                  10                  15

Pro Val Met Ile Lys Ala Ser Ala Gly Gly Gly Gly Lys Gly Met Arg
            20                  25                  30

Ile Ala Trp Asp Asp Glu Glu Thr Arg Asp Gly Phe Arg Leu Ser Ser
            35                  40                  45

Gln Glu Ala Ala Ser Ser Phe Gly Asp Asp Arg Leu Leu Ile Glu Lys
     50                  55                  60

Phe Ile Asp Asn Pro Arg His Ile Glu Ile Gln Val Leu Gly Asp Lys
65                   70                  75                  80

His Gly Asn Ala Leu Trp Leu Asn Glu Arg Glu Cys Ser Ile Gln Arg
                85                  90                  95

Arg Asn Gln Lys Val Val Glu Glu Ala Pro Ser Ile Phe Leu Asp Ala
            100                 105                 110
```

Glu Thr Arg Arg Ala Met Gly Glu Gln Ala Val Ala Leu Ala Arg Ala
            115                 120                 125

Val Lys Tyr Ser Ser Ala Gly Thr Val Glu Phe Leu Val Asp Ser Lys
    130                 135                 140

<210> SEQ ID NO 80
<211> LENGTH: 47
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 80

Lys Asn Phe Tyr Phe Leu Glu Met Asn Thr Arg Leu Gln Val Glu His
  1               5                  10                  15

Pro Val Thr Glu Cys Ile His Trp Pro Gly Pro Ser Pro Gly Lys Thr
                 20                  25                  30

Val Leu Gln Glu His Leu Ser Gly Thr Asn Lys Leu Ile Phe Ala
             35                  40                  45

<210> SEQ ID NO 81
<211> LENGTH: 28
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 81

Asn Gly Trp Ala Val Glu Cys Arg Val Tyr Ala Glu Asp Pro Tyr Lys
  1               5                  10                  15

Ser Phe Gly Leu Pro Ser Ile Gly Arg Leu Ser Gln
                 20                  25

<210> SEQ ID NO 82
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 82

Tyr Gln Glu Pro Leu His Leu Pro Gly Val Arg Val Asp Ser
  1               5                  10

<210> SEQ ID NO 83
<211> LENGTH: 44
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 83

Gly Ile Gln Pro Gly Ser Asp Ile Ser Ile Tyr Tyr Asp Pro Met Ile
  1               5                  10                  15

Ser Lys Leu Ile Thr Tyr Gly Ser Asp Arg Thr Glu Ala Leu Lys Arg
                 20                  25                  30

Met Ala Asp Ala Leu Asp Asn Tyr Val Ile Arg Gly
             35                  40

```
<210> SEQ ID NO 84
<211> LENGTH: 251
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 84

Val Thr His Asn Ile Ala Leu Leu Arg Glu Val Ile Ile Asn Ser Arg
  1               5                  10                  15

Phe Val Lys Gly Asp Ile Ser Thr Lys Phe Leu Ser Asp Val Tyr Pro
                 20                  25                  30

Asp Gly Phe Lys Gly His Met Leu Thr Lys Ser Glu Lys Asn Gln Leu
             35                  40                  45

Leu Ala Ile Ala Ser Ser Leu Phe Val Ala Phe Gln Leu Arg Ala Gln
         50                  55                  60

His Phe Gln Glu Asn Ser Arg Met Pro Val Ile Lys Pro Asp Ile Ala
 65                  70                  75                  80

Asn Trp Glu Leu Ser Val Lys Leu His Asp Lys Val His Thr Val Val
                 85                  90                  95

Ala Ser Asn Asn Gly Ser Val Phe Ser Val Glu Val Asp Gly Ser Lys
                100                 105                 110

Leu Asn Val Thr Ser Thr Trp Asn Leu Ala Ser Pro Leu Leu Ser Val
            115                 120                 125

Ser Val Asp Gly Thr Gln Arg Thr Val Gln Cys Leu Ser Arg Glu Ala
        130                 135                 140

Gly Gly Asn Met Ser Ile Gln Phe Leu Gly Thr Val Tyr Lys Val Asn
145                 150                 155                 160

Ile Leu Thr Arg Leu Ala Ala Glu Leu Asn Lys Phe Met Leu Glu Lys
                165                 170                 175

Val Thr Glu Asp Thr Ser Ser Val Leu Arg Ser Pro Met Pro Gly Val
                180                 185                 190

Val Val Ala Val Ser Val Lys Pro Gly Asp Ala Val Ala Glu Gly Gln
            195                 200                 205

Glu Ile Cys Val Ile Glu Ala Met Lys Met Gln Asn Ser Met Thr Ala
        210                 215                 220

Gly Lys Thr Gly Thr Val Lys Ser Val His Cys Gln Ala Gly Asp Thr
225                 230                 235                 240

Val Gly Glu Gly Asp Leu Leu Val Glu Leu Glu
                245                 250

<210> SEQ ID NO 85
<211> LENGTH: 90
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 85

Met Pro Tyr Arg Glu Arg Phe Cys Ala Ile Arg Trp Cys Arg Asn Ser
  1               5                  10                  15

Gly Arg Ser Ser Gln Gln Leu Leu Trp Thr Leu Lys Arg Ala Pro Val
                 20                  25                  30

Tyr Ser Gln Gln Cys Leu Val Val Ser Arg Ser Leu Ser Ser Val Glu
             35                  40                  45
```

```
Tyr Glu Pro Lys Glu Lys Thr Phe Asp Lys Ile Leu Ile Ala Asn Arg
        50                  55                  60

Gly Glu Ile Ala Cys Arg Val Ile Lys Thr Cys Arg Lys Met Gly Ile
 65                  70                  75                  80

Arg Thr Val Ala Ile His Ser Asp Val Asp
                 85                  90

<210> SEQ ID NO 86
<211> LENGTH: 21
<212> TYPE: PRT
<213> ORGANISM: Artificial Sequence
<220> FEATURE:
<223> OTHER INFORMATION: Description of Artificial Sequence:   Synthetic
      Peptide

<400> SEQUENCE: 86

Ala Ser Ser Val His Val Lys Met Ala Asp Glu Ala Val Cys Val Gly
 1               5                  10                  15

Pro Ala Pro Thr Ser
             20

<210> SEQ ID NO 87
<211> LENGTH: 38
<212> TYPE: PRT
<213> ORGANISM: Artificial Sequence
<220> FEATURE:
<223> OTHER INFORMATION: Description of Artificial Sequence:   Synthetic
      Peptide

<400> SEQUENCE: 87

Lys Ser Tyr Leu Asn Met Asp Ala Ile Met Glu Ala Ile Lys Lys Thr
 1               5                  10                  15

Gly Ala Gln Ala Val His Pro Gly Tyr Gly Phe Leu Ser Glu Asn Lys
             20                  25                  30

Glu Phe Ala Lys Cys Leu
         35

<210> SEQ ID NO 88
<211> LENGTH: 41
<212> TYPE: PRT
<213> ORGANISM: Artificial Sequence
<220> FEATURE:
<223> OTHER INFORMATION: Description of Artificial Sequence:   Synthetic
      Peptide

<400> SEQUENCE: 88

Ala Ala Glu Asp Val Thr Phe Ile Gly Pro Asp Thr His Ala Ile Gln
 1               5                  10                  15

Ala Met Gly Asp Lys Ile Glu Ser Lys Leu Leu Ala Lys Arg Ala Lys
             20                  25                  30

Val Asn Thr Ile Pro Gly Phe Asp Gly
             35                  40

<210> SEQ ID NO 89
<211> LENGTH: 144
<212> TYPE: PRT
<213> ORGANISM: Artificial Sequence
<220> FEATURE:
<223> OTHER INFORMATION: Description of Artificial Sequence:   Synthetic
      Peptide

<400> SEQUENCE: 89

Leu Lys Asp Ala Asp Glu Ala Val Arg Ile Ala Arg Glu Ile Gly Tyr
 1               5                  10                  15
```

```
Pro Val Met Ile Lys Ala Ser Ala Gly Gly Gly Lys Gly Met Arg
            20                  25                  30

Ile Pro Trp Asp Asp Glu Glu Thr Arg Asp Gly Phe Arg Phe Ser Ser
        35                  40                  45

Gln Glu Ala Ala Ser Ser Phe Gly Asp Asp Arg Leu Leu Ile Glu Lys
    50                  55                  60

Phe Ile Asp Asn Pro Arg His Ile Glu Ile Gln Val Leu Gly Asp Lys
 65                  70                  75                  80

His Gly Asn Ala Leu Trp Leu Asn Glu Arg Glu Cys Ser Ile Gln Arg
                85                  90                  95

Arg Asn Gln Lys Val Val Glu Ala Pro Ser Ile Phe Leu Asp Pro
            100                 105                 110

Glu Thr Arg Arg Ala Met Gly Glu Gln Ala Val Ala Trp Pro Lys Ala
        115                 120                 125

Val Lys Tyr Ser Ser Ala Gly Thr Val Glu Phe Leu Val Asp Ser Gln
    130                 135                 140
```

<210> SEQ ID NO 90
<211> LENGTH: 48
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 90

```
Lys Asn Phe Tyr Phe Leu Glu Met Asn Thr Arg Leu Gln Val Glu His
 1               5                  10                  15

Pro Val Thr Glu Cys Ile Thr Gly Leu Asp Leu Val Gln Glu Met Ile
            20                  25                  30

Leu Val Ala Lys Gly Tyr Pro Leu Arg His Lys Gln Glu Asp Ile Pro
        35                  40                  45
```

<210> SEQ ID NO 91
<211> LENGTH: 29
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 91

```
Ile Ser Gly Trp Ala Val Glu Cys Arg Val Tyr Ala Glu Asp Pro Tyr
 1               5                  10                  15

Lys Ser Phe Gly Leu Pro Ser Ile Gly Arg Leu Ser Gln
            20                  25
```

<210> SEQ ID NO 92
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 92

```
Tyr Gln Glu Pro Ile His Leu Pro Gly Val Arg Val Asp Ser
 1               5                  10
```

<210> SEQ ID NO 93
<211> LENGTH: 44
<212> TYPE: PRT

```
<213> ORGANISM: Artificial Sequence
<220> FEATURE:
<223> OTHER INFORMATION: Description of Artificial Sequence:  Synthetic
      Peptide

<400> SEQUENCE: 93

Gly Ile Gln Pro Gly Ser Asp Ile Ser Ile Tyr His Asp Pro Met Ile
 1               5                  10                  15

Ser Lys Leu Val Thr Tyr Gly Ser Asp Arg Ala Glu Ala Leu Lys Arg
                20                  25                  30

Met Glu Asp Ala Leu Asp Ser Tyr Val Ile Arg Gly
            35                  40

<210> SEQ ID NO 94
<211> LENGTH: 251
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 94

Val Thr His Asn Ile Pro Leu Leu Arg Glu Val Ile Ile Asn Thr Arg
 1               5                  10                  15

Phe Val Lys Gly Asp Ile Ser Thr Lys Phe Leu Ser Asp Val Tyr Pro
                20                  25                  30

Asp Gly Phe Lys Gly His Met Leu Thr Pro Ser Glu Arg Asp Gln Leu
            35                  40                  45

Leu Ala Ile Ala Ser Ser Leu Phe Val Ala Ser Gln Leu Arg Ala Gln
 50                  55                  60

Arg Phe Gln Glu His Ser Arg Val Pro Val Ile Arg Pro Asp Val Ala
 65                  70                  75                  80

Lys Trp Glu Leu Ser Val Lys Leu His Asp Glu Asp His Thr Val Val
                85                  90                  95

Ala Ser Asn Asn Gly Pro Thr Phe Asn Val Glu Val Asp Gly Ser Lys
            100                 105                 110

Leu Asn Val Thr Ser Thr Trp Asn Leu Ala Ser Pro Leu Leu Ser Val
            115                 120                 125

Asn Val Asp Gly Thr Gln Arg Thr Val Gln Cys Leu Ser Pro Asp Ala
130                 135                 140

Gly Gly Asn Met Ser Ile Gln Phe Leu Gly Thr Val Tyr Lys Val His
145                 150                 155                 160

Ile Leu Thr Lys Leu Ala Ala Glu Leu Asn Lys Phe Met Leu Glu Lys
                165                 170                 175

Val Pro Lys Asp Thr Ser Ser Val Leu Arg Ser Pro Lys Pro Gly Val
            180                 185                 190

Val Val Ala Val Ser Val Lys Pro Gly Asp Met Val Ala Glu Gly Gln
        195                 200                 205

Glu Ile Cys Val Ile Glu Ala Met Lys Met Gln Asn Ser Met Thr Ala
    210                 215                 220

Gly Lys Met Gly Lys Val Lys Leu Val His Cys Lys Ala Gly Asp Thr
225                 230                 235                 240

Val Gly Glu Gly Asp Leu Leu Val Glu Leu Glu
                245                 250

<210> SEQ ID NO 95
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      Peptide

<400> SEQUENCE: 95

Gln Arg Lys Phe Ala Gly Leu Arg Asp Asn Phe Asn Leu Leu Gly Glu
  1               5                  10                  15

Lys

<210> SEQ ID NO 96
<211> LENGTH: 34
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 96

Asn Lys Ile Leu Val Ala Asn Arg Gly Glu Ile Pro Ile Arg Ile Phe
  1               5                  10                  15

Arg Thr Ala His Glu Leu Ser Met Gln Thr Val Ala Ile Tyr Ser His
             20                  25                  30

Glu Asp

<210> SEQ ID NO 97
<211> LENGTH: 24
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 97

Arg Leu Ser Thr His Lys Gln Lys Ala Asp Glu Ala Tyr Val Ile Gly
  1               5                  10                  15

Glu Val Gly Gln Tyr Thr Pro Val
             20

<210> SEQ ID NO 98
<211> LENGTH: 38
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 98

Gly Ala Tyr Leu Ala Ile Asp Glu Ile Ile Ser Ile Ala Gln Lys His
  1               5                  10                  15

Gln Val Asp Phe Ile His Pro Gly Tyr Gly Phe Leu Ser Glu Asn Ser
             20                  25                  30

Glu Phe Ala Asp Lys Val
         35

<210> SEQ ID NO 99
<211> LENGTH: 41
<212> TYPE: PRT
<213> ORGANISM: Artificial Sequence
<220> FEATURE:
<223> OTHER INFORMATION: Description of Artificial Sequence: Synthetic
      Peptide
```

<400> SEQUENCE: 99

Val Lys Ala Gly Ile Thr Trp Ile Gly Pro Pro Ala Glu Val Ile Asp
1               5                   10                  15

Ser Val Gly Asp Lys Val Ser Ala Arg Asn Leu Ala Ala Lys Ala Asn
            20                  25                  30

Val Pro Thr Val Pro Gly Thr Pro Gly
        35                  40

<210> SEQ ID NO 100
<211> LENGTH: 144
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 100

Ile Glu Thr Val Glu Glu Ala Leu Asp Phe Val Asn Glu Tyr Gly Tyr
1               5                   10                  15

Pro Val Ile Ile Lys Ala Ala Phe Gly Gly Gly Gly Arg Gly Met Arg
            20                  25                  30

Val Val Arg Glu Gly Asp Asp Val Ala Asp Ala Phe Gln Arg Ala Thr
        35                  40                  45

Ser Glu Ala Arg Thr Ala Phe Gly Asn Gly Thr Cys Phe Val Glu Arg
    50                  55                  60

Phe Leu Asp Lys Pro Lys His Ile Glu Val Gln Leu Leu Ala Asp Asn
65                  70                  75                  80

His Gly Asn Val Val His Leu Phe Glu Arg Asp Cys Ser Val Gln Arg
                85                  90                  95

Arg His Gln Lys Val Val Glu Val Ala Pro Ala Lys Thr Leu Pro Arg
            100                 105                 110

Glu Val Arg Asp Ala Ile Leu Thr Asp Ala Val Lys Leu Ala Lys Glu
        115                 120                 125

Cys Gly Tyr Arg Asn Ala Gly Thr Ala Glu Phe Leu Val Asp Asn Gln
    130                 135                 140

<210> SEQ ID NO 101
<211> LENGTH: 51
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 101

Asn Arg His Tyr Phe Ile Glu Ile Asn Pro Arg Ile Gln Val Glu His
1               5                   10                  15

Thr Ile Thr Glu Glu Ile Thr Gly Ile Asp Ile Val Ala Ala Gln Ile
            20                  25                  30

Gln Ile Ala Ala Gly Ala Ser Leu Pro Gln Leu Gly Leu Phe Gln Asp
        35                  40                  45

Lys Ile Thr
    50

<210> SEQ ID NO 102
<211> LENGTH: 20
<212> TYPE: PRT
<213> ORGANISM: Artificial Sequence

```
<220> FEATURE:
<223> OTHER INFORMATION: Description of Artificial Sequence:  Synthetic
      Peptide

<400> SEQUENCE: 102

Thr Arg Gly Phe Ala Ile Gln Cys Arg Ile Thr Thr Glu Asp Pro Ala
 1               5                  10                  15

Lys Asn Phe Gln
            20

<210> SEQ ID NO 103
<211> LENGTH: 14
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 103

Pro Asp Thr Gly Arg Ile Glu Val Tyr Arg Ser Ala Gly Gly
 1               5                  10

<210> SEQ ID NO 104
<211> LENGTH: 52
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 104

Asn Gly Val Arg Leu Asp Gly Gly Asn Ala Tyr Ala Gly Thr Ile Ile
 1               5                  10                  15

Ser Pro His Tyr Asp Ser Met Leu Val Lys Cys Ser Cys Ser Gly Ser
                20                  25                  30

Thr Tyr Glu Ile Val Arg Arg Lys Met Ile Arg Ala Leu Ile Glu Phe
            35                  40                  45

Arg Ile Arg Gly
        50

<210> SEQ ID NO 105
<211> LENGTH: 257
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 105

Val Lys Thr Asn Ile Pro Phe Leu Leu Thr Leu Leu Thr Asn Pro Val
 1               5                  10                  15

Phe Ile Glu Gly Thr Tyr Trp Gly Thr Phe Ile Asp Asp Thr Pro Gln
                20                  25                  30

Leu Phe Gln Met Val Ser Ser Gln Asn Arg Ala Gln Lys Leu Leu His
            35                  40                  45

Tyr Leu Ala Asp Val Ala Asp Asn Gly Ser Ser Ile Lys Gly Gln Ile
        50                  55                  60

Gly Leu Pro Lys Leu Lys Ser Asn Pro Ser Val Pro His Ser Tyr Asn
65                  70                  75                  80

Met Tyr Pro Arg Val Tyr Glu Asp Phe Gln Lys Met Arg Glu Thr Tyr
                85                  90                  95
```

-continued

```
Gly Asp Leu Ser Val Leu Pro Thr Arg Ser Phe Leu Ser Pro Leu Glu
                100                 105                 110

Thr Asp Glu Glu Ile Glu Val Ile Glu Gln Gly Lys Thr Leu Ile
            115                 120                 125

Ile Lys Leu Gln Ala Val Gly Asp Leu Asn Lys Lys Thr Gly Glu Arg
130                 135                 140

Glu Val Tyr Phe Asp Leu Asn Gly Glu Met Arg Lys Ile Arg Val Ala
145                 150                 155                 160

Asp Arg Ser Gln Lys Val Glu Thr Val Thr Lys Ser Lys Ala Asp Met
                165                 170                 175

His Asp Pro Leu His Ile Gly Ala Pro Met Ala Gly Val Ile Val Glu
                180                 185                 190

Val Lys Val His Lys Gly Ser Leu Ile Lys Lys Gly Gln Pro Val Ala
                195                 200                 205

Val Leu Ser Ala Met Lys Met Glu Met Ile Ile Ser Ser Pro Ser Asp
210                 215                 220

Gly Gln Val Lys Glu Val Phe Val Ser Asp Gly Glu Asn Val Asp Ser
225                 230                 235                 240

Ser Asp Leu Leu Val Leu Leu Glu Asp Gln Val Pro Val Glu Thr Lys
                245                 250                 255

Ala
```

<210> SEQ ID NO 106
<211> LENGTH: 165
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 106

```
Val Leu Thr Val Ala Leu Phe Pro Gln Pro Gly Leu Lys Phe Leu Glu
  1               5                  10                  15

Asn Arg His Asn Pro Ala Ala Phe Glu Pro Val Pro Gln Ala Glu Ala
                20                  25                  30

Ala Gln Pro Val Ala Lys Ala Glu Lys Pro Ala Ala Ser Gly Val Tyr
            35                  40                  45

Thr Val Glu Val Glu Gly Lys Ala Phe Val Lys Val Ser Asp Gly
     50                  55                  60

Gly Asp Val Ser Gln Leu Thr Ala Ala Pro Ala Pro Ala Pro Ala
 65                  70                  75                  80

Pro Ala Pro Ala Ser Ala Pro Ala Ala Ala Pro Ala Gly Ala Gly
                85                  90                  95

Thr Pro Val Thr Ala Pro Leu Ala Gly Thr Ile Trp Lys Val Leu Ala
                100                 105                 110

Ser Glu Gly Gln Thr Val Ala Ala Gly Glu Val Leu Leu Ile Leu Glu
            115                 120                 125

Ala Met Lys Met Glu Thr Glu Ile Arg Ala Ala Gln Ala Gly Thr Val
130                 135                 140

Arg Gly Ile Ala Val Lys Ala Gly Asp Ala Val Ala Val Gly Asp Thr
145                 150                 155                 160

Leu Met Thr Leu Ala
                165
```

<210> SEQ ID NO 107
<211> LENGTH: 123

<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 107

Met Lys Leu Lys Val Thr Val Asn Gly Thr Ala Tyr Asp Val Asp Val
 1               5                  10                  15

Asp Val Asp Lys Ser His Glu Asn Pro Met Gly Thr Ile Leu Phe Gly
            20                  25                  30

Gly Thr Gly Gly Ala Pro Ala Pro Arg Ala Ala Gly Gly Ala Gly
        35                  40                  45

Ala Gly Lys Ala Gly Glu Gly Glu Ile Pro Ala Pro Leu Ala Gly Thr
    50                  55                  60

Val Ser Lys Ile Leu Val Lys Glu Gly Asp Thr Val Lys Ala Gly Gln
65                  70                  75                  80

Thr Val Leu Val Leu Glu Ala Met Lys Met Glu Thr Glu Ile Asn Ala
                85                  90                  95

Pro Thr Asp Gly Lys Val Glu Lys Val Leu Val Lys Glu Arg Asp Ala
            100                 105                 110

Val Gln Gly Gly Gln Gly Leu Ile Lys Ile Gly
        115                 120

<210> SEQ ID NO 108
<211> LENGTH: 1473
<212> TYPE: DNA
<213> ORGANISM: Artificial Sequence
<220> FEATURE:
<223> OTHER INFORMATION: Description of Artificial Sequence: Synthetic
      Peptide

<400> SEQUENCE: 108
gtgatgatca aggcatcatg gggtgggggt ggtaaaggaa taaggaaggt acataatgat      60
gatgaggtca gagcattgtt taagcaagtg caaggagaag tccccggatc gcctatattt     120
attatgaagg tggcatctca gagtcgacat ctagaggttc aattgctctg tgacaagcat     180
ggcaacgtgg cagcactgca cagtcgagac tgtagtgttc aaagaaggca tcaaagatc      240 attgaggagg gaccaattac agttgctcct ccagaaacaa ttaaagagct tgagcaggcg     300
gcaaggcgac tagctaaatg tgtgcaatat cagggtgctg ctacagtgga atatctgtac     360
agcatggaaa caggcgaata ctatttcctg gagcttaatc caaggttgca ggtagaacac     420
cctgtgaccg aatggattgc tgaaataaac ttaccygcat ctcaagttgt agtaggaatg     480
ggcataccac tctacaacat tccagagatc agacgctttt atggaataga acatggaggt     540
ggctatcayg cttggaagga aatatcagct gttgcaacta aatttgatyt ggacaaagca     600
cagtctgtaa agccaaargg tcattgtgta gcagttagag ttactagcga ggatccagat     660
gatgggttta agcctacmag tggaagagtr gaagagctga actttaaaag taaacccaat     720
gtttgggcct atttctcygt targtccgga ggtgcaattc aygagttctc tgattcccag     780
tttggtcatg tttttgctty tggggaatct aggtcwttgg caatagccaa tatggtactt     840
gggttaaaag agatccaaat tcgtggagag atacgcacta atgttgacta cactgtggat     900
ctcttgaatg ctgcagagta ccgagaaaat awgattcaca ctggttggct agacagcaga     960
atagcwatgc gygttagagc agagaggccc ccatggtacc tttcagttgt tggtggagct    1020
ctatatgaag catcaagcag gagctcgagt gttgtaaccg attatgttgg ttatctcagt    1080

```
aaaggtcaaa taccaccaaa gcacatctct cttgtcaayt tgactgtaac actgaatata   1140
gatgggagca aatatacgat tgagacagta cgaggtggac cccgtagcta caaattaaga   1200
attaatgaat cagaggttga rgcagagata catttcctgc gagatggcgg acycttaatg   1260
cagtyggatg gaaacagtca tgtaatttac gccgagacag aagctkctgg cacgcgcctt   1320
ctaatcaatg ggagaacatg cttattacag aaagagcayg atccttccag gttgttggct   1380
gatacaccrt gcaarcttct tcggttttg gtcgcggatr gttctcatgt ggttgctgat   1440
acgccatatg cygaggtgga ggccatgaaa atg                                1473
```

<210> SEQ ID NO 109
<211> LENGTH: 491
<212> TYPE: PRT
<213> ORGANISM: Artificial Sequence
<220> FEATURE:
<223> OTHER INFORMATION: Description of Artificial Sequence: Synthetic Peptide
<221> NAME/KEY: MOD_RES
<222> LOCATION: (248)..(474)
<223> OTHER INFORMATION: XAA = Any set containing N

<400> SEQUENCE: 109

```
Val Met Ile Lys Ala Ser Trp Gly Gly Gly Lys Gly Ile Arg Lys
  1               5                  10                  15

Val His Asn Asp Asp Glu Val Arg Ala Leu Phe Lys Gln Val Gln Gly
                 20                  25                  30

Glu Val Pro Gly Ser Pro Ile Phe Ile Met Lys Val Ala Ser Gln Ser
             35                  40                  45

Arg His Leu Glu Val Gln Leu Leu Cys Asp Lys His Gly Asn Val Ala
         50                  55                  60

Ala Leu His Ser Arg Asp Cys Ser Val Gln Arg Arg His Gln Lys Ile
     65                  70                  75                  80

Ile Glu Glu Gly Pro Ile Thr Val Ala Pro Pro Glu Thr Ile Lys Glu
                 85                  90                  95

Leu Glu Gln Ala Ala Arg Arg Leu Ala Lys Cys Val Gln Tyr Gln Gly
            100                 105                 110

Ala Ala Thr Val Glu Tyr Leu Tyr Ser Met Glu Thr Gly Glu Tyr Tyr
        115                 120                 125

Phe Leu Glu Leu Asn Pro Arg Leu Gln Val Glu His Pro Val Thr Glu
    130                 135                 140

Trp Ile Ala Glu Ile Asn Leu Pro Ala Ser Gln Val Val Val Gly Met
145                 150                 155                 160

Gly Ile Pro Leu Tyr Asn Ile Pro Glu Ile Arg Arg Phe Tyr Gly Ile
                165                 170                 175

Glu His Gly Gly Gly Tyr His Ala Trp Lys Glu Ile Ser Ala Val Ala
            180                 185                 190

Thr Lys Phe Asp Leu Asp Lys Ala Gln Ser Val Lys Pro Lys Gly His
        195                 200                 205

Cys Val Ala Val Arg Val Thr Ser Glu Asp Pro Asp Asp Gly Phe Lys
    210                 215                 220

Pro Thr Ser Gly Arg Val Glu Glu Leu Asn Phe Lys Ser Lys Pro Asn
225                 230                 235                 240

Val Trp Ala Tyr Phe Ser Val Xaa Ser Gly Gly Ala Ile His Glu Phe
                245                 250                 255

Ser Asp Ser Gln Phe Gly His Val Phe Ala Xaa Gly Glu Ser Arg Ser
            260                 265                 270
```

```
Leu Ala Ile Ala Asn Met Val Leu Gly Leu Lys Glu Ile Gln Ile Arg
        275                 280                 285
Gly Glu Ile Arg Thr Asn Val Asp Tyr Thr Val Asp Leu Leu Asn Ala
    290                 295                 300
Ala Glu Tyr Arg Glu Asn Xaa Ile His Thr Gly Trp Leu Asp Ser Arg
305                 310                 315                 320
Ile Ala Met Arg Val Arg Ala Glu Arg Pro Pro Trp Tyr Leu Ser Val
                325                 330                 335
Val Gly Gly Ala Leu Tyr Glu Ala Ser Ser Arg Ser Ser Ser Val Val
            340                 345                 350
Thr Asp Tyr Val Gly Tyr Leu Ser Lys Gly Gln Ile Pro Pro Lys His
        355                 360                 365
Ile Ser Leu Val Asn Leu Thr Val Thr Leu Asn Ile Asp Gly Ser Lys
    370                 375                 380
Tyr Thr Ile Glu Thr Val Arg Gly Gly Pro Arg Ser Tyr Lys Leu Arg
385                 390                 395                 400
Ile Asn Glu Ser Glu Val Glu Ala Glu Ile His Xaa Leu Arg Asp Gly
                405                 410                 415
Gly Xaa Leu Met Gln Xaa Asp Gly Asn Ser His Val Ile Tyr Ala Glu
            420                 425                 430
Thr Glu Ala Xaa Gly Thr Arg Leu Leu Ile Asn Gly Arg Thr Cys Leu
        435                 440                 445
Leu Gln Lys Glu His Asp Pro Ser Arg Leu Leu Ala Asp Thr Pro Cys
    450                 455                 460
Lys Leu Leu Arg Phe Leu Val Ala Asp Xaa Ser His Val Val Ala Asp
465                 470                 475                 480
Thr Pro Tyr Ala Glu Val Glu Ala Met Lys Met
                485                 490

<210> SEQ ID NO 110
<211> LENGTH: 435
<212> TYPE: DNA
<213> ORGANISM: Artificial Sequence
<220> FEATURE:
<223> OTHER INFORMATION: Description of Artificial Sequence: Synthetic
      Peptide

<400> SEQUENCE: 110
tctagacttt aacgagattc gtcaactgct gacaactatt gcacaaacag atatcgcgga      60
agtaacgctc aaaagtgatg attttgaact aacggtgcgt aaagctgttg gtgtgaataa     120
tagtgttgtg ccggttgtga cagcacccct gagtggtgtg gtaggttcgg gattgccatc     180
ggctataccg attgtagccc atgctgccca atctccatct ccagagccgg aacaagccg      240 tgctgctgat catgctgtca cgagttctgg ctcacagcca ggagcaaaaa tcattgacca     300
aaaattagca gaagtggctt ccccaatggt gggaacattt taccgcgctc ctgcaccagg     360
tgaagcggta tttgtggaag tcggcgatcg catccgtcaa ggtcaaaccg tctgcatcat     420
cgaagcgatg aaaag                                                     435

<210> SEQ ID NO 111
<211> LENGTH: 145
<212> TYPE: PRT
<213> ORGANISM: Artificial Sequence
<220> FEATURE:
<223> OTHER INFORMATION: Description of Artificial Sequence: Synthetic
      Peptide
```

<400> SEQUENCE: 111

Leu Asp Phe Asn Glu Ile Arg Gln Leu Leu Thr Thr Ile Ala Gln Thr
1               5                  10                  15

Asp Ile Ala Glu Val Thr Leu Lys Ser Asp Asp Phe Glu Leu Thr Val
            20                  25                  30

Arg Lys Ala Val Gly Val Asn Asn Ser Val Pro Val Thr Ala
        35                  40                  45

Pro Leu Ser Gly Val Val Gly Ser Gly Leu Pro Ser Ala Ile Pro Ile
    50                  55                  60

Val Ala His Ala Ala Pro Ser Pro Ser Pro Glu Pro Gly Thr Ser Arg
65              70                  75                  80

Ala Ala Asp His Ala Val Thr Ser Ser Gly Ser Gln Pro Gly Ala Lys
                85                  90                  95

Ile Ile Asp Gln Lys Leu Ala Glu Val Ala Ser Pro Met Val Gly Thr
            100                 105                 110

Phe Tyr Arg Ala Pro Ala Pro Gly Glu Ala Val Phe Val Glu Val Gly
        115                 120                 125

Asp Arg Ile Arg Gln Gly Gln Thr Val Cys Ile Ile Glu Ala Met Lys
    130                 135                 140

Met
145

<210> SEQ ID NO 112
<211> LENGTH: 22
<212> TYPE: DNA
<213> ORGANISM: Artificial Sequence
<220> FEATURE:
<223> OTHER INFORMATION: Description of Artificial Sequence: Synthetic
      Peptide
<221> NAME/KEY: modified_base
<222> LOCATION: (11)..(14)
<223> OTHER INFORMATION: N = A, C, G, or T/U

<400> SEQUENCE: 112
tcgaattcgt natnathaar gc                                            22

<210> SEQ ID NO 113
<211> LENGTH: 22
<212> TYPE: DNA
<213> ORGANISM: Artificial Sequence
<220> FEATURE:
<223> OTHER INFORMATION: Description of Artificial Sequence: Synthetic
      Peptide
<221> NAME/KEY: modified_base
<222> LOCATION: (17)
<223> OTHER INFORMATION: N = A, C, G, or T/U

<400> SEQUENCE: 113
gctctagagk rtgytcnacy tc                                            22

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      Peptide

<400> SEQUENCE: 114
gctctagaat actatttcct g                                             21

<210> SEQ ID NO 115
<211> LENGTH: 22
<212> TYPE: DNA
<213> ORGANISM: Artificial Sequence
<220> FEATURE:
<223> OTHER INFORMATION: Description of Artificial Sequence: Synthetic
      Peptide
<221> NAME/KEY: modified_base
<222> LOCATION: (10)..(20)
<223> OTHER INFORMATION: N = A, C, G or T/U

<400> SEQUENCE: 115
tcgaattcwn catyttcatn rc                                            22

<210> SEQ ID NO 116
<211> LENGTH: 23
<212> TYPE: DNA
<213> ORGANISM: Artificial Sequence
<220> FEATURE:
<223> OTHER INFORMATION: Description of Artificial Sequence: Synthetic
      Peptide

<400> SEQUENCE: 116
gctctagayt tyaaygarat hmg                                           23

<210> SEQ ID NO 117
<211> LENGTH: 491
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 117

Val Met Ile Lys Ala Ser Trp Gly Gly Gly Lys Gly Ile Arg Lys
 1               5                  10                  15

Val His Asn Asp Asp Glu Val Arg Ala Leu Phe Lys Gln Val Gln Gly
                20                  25                  30

Glu Val Pro Gly Ser Pro Ile Phe Ile Met Lys Val Ala Ser Gln Ser
            35                  40                  45

Arg His Leu Glu Val Gln Leu Leu Cys Asp Lys His Gly Asn Val Ala
        50                  55                  60

Ala Leu His Ser Arg Asp Cys Ser Val Gln Arg Arg His Gln Lys Ile
    65                  70                  75                  80

Ile Glu Glu Gly Pro Ile Thr Val Ala Pro Glu Thr Ile Lys Glu
                85                  90                  95

Leu Glu Gln Ala Ala Arg Arg Leu Ala Lys Cys Val Gln Tyr Gln Gly
            100                 105                 110

Ala Ala Thr Val Glu Tyr Leu Tyr Ser Met Glu Thr Gly Glu Tyr Tyr
        115                 120                 125

Phe Leu Glu Leu Asn Pro Arg Leu Gln Val Glu His Pro Val Thr Glu
    130                 135                 140

Trp Ile Ala Glu Ile Asn Leu Pro Ala Ser Gln Val Val Gly Met
145                 150                 155                 160

Gly Ile Pro Leu Tyr Asn Ile Pro Glu Ile Arg Arg Phe Tyr Gly Ile
                165                 170                 175

Glu His Gly Gly Gly Tyr His Ala Trp Lys Glu Ile Ser Ala Val Ala
            180                 185                 190

Thr Lys Phe Asp Leu Asp Lys Ala Trp Ser Val Lys Pro Lys Gly His
        195                 200                 205

Cys Val Ala Val Arg Val Thr Ser Glu Asp Pro Asp Gly Phe Lys
    210                 215                 220

Pro Thr Ser Gly Arg Val Glu Glu Leu Asn Phe Lys Ser Lys Pro Asn
225                 230                 235                 240

Val Trp Ala Tyr Phe Ser Val Lys Ser Gly Ala Ile His Glu Phe
                245                 250                 255

Ser Asp Ser Gln Phe Gly His Val Phe Ala Phe Gly Glu Ser Arg Ser
            260                 265                 270

Leu Ala Ile Ala Asn Met Val Leu Gly Leu Lys Glu Ile Gln Ile Arg
            275                 280                 285

Gly Glu Ile Arg Thr Asn Val Asp Tyr Thr Val Asp Leu Leu Asn Ala
290                 295                 300

Ala Glu Tyr Arg Glu Asn Met Ile His Thr Gly Trp Leu Asp Ser Arg
305                 310                 315                 320

Ile Ala Met Arg Val Arg Ala Glu Arg Pro Pro Trp Tyr Leu Ser Val
                325                 330                 335

Val Gly Gly Ala Leu Tyr Glu Ala Ser Ser Arg Ser Ser Ser Val Val
            340                 345                 350

Thr Asp Tyr Val Gly Tyr Leu Ser Lys Gly Gln Ile Pro Pro Lys His
            355                 360                 365

Ile Ser Leu Val Asn Leu Thr Val Thr Leu Asn Ile Asp Gly Ser Lys
370                 375                 380

Tyr Thr Ile Glu Thr Val Arg Gly Gly Pro Arg Ser Tyr Lys Leu Arg
385                 390                 395                 400

Ile Asn Glu Ser Glu Val Glu Ala Glu Ile His Phe Leu Arg Asp Gly
                405                 410                 415

Gly Leu Leu Met Gln Leu Asp Gly Asn Ser His Val Ile Tyr Ala Glu
            420                 425                 430

Thr Glu Ala Ala Gly Thr Arg Leu Leu Ile Asn Gly Arg Thr Cys Leu
            435                 440                 445

Leu Gln Lys Glu His Asp Pro Ser Arg Leu Leu Ala Asp Thr Pro Cys
450                 455                 460

Lys Leu Leu Arg Phe Leu Val Ala Asp Gly Ser His Val Val Ala Asp
465                 470                 475                 480

Thr Pro Tyr Ala Glu Val Glu Ala Met Lys Met
                485                 490

<210> SEQ ID NO 118
<211> LENGTH: 852
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 118

Met Asp Glu Pro Ser Pro Leu Ala Lys Thr Leu Glu Leu Asn Gln His
1               5                   10                  15

Ser Arg Phe Ile Ile Gly Ser Val Ser Glu Asp Asn Ser Glu Asp Glu
            20                  25                  30

Ile Ser Asn Leu Val Lys Leu Asp Leu Glu Glu Lys Glu Gly Ser Leu
        35                  40                  45

Ser Pro Ala Ser Val Ser Ser Asp Thr Leu Ser Asp Leu Gly Ile Ser
    50                  55                  60

Ala Leu Gln Asp Gly Leu Ala Phe His Met Arg Ser Ser Met Ser Gly
65                  70                  75                  80

-continued

```
Leu His Leu Val Lys Gln Gly Arg Asp Arg Lys Lys Ile Asp Ser Gln
                85                  90                  95

Arg Asp Phe Thr Val Ala Ser Pro Ala Glu Phe Val Thr Arg Phe Gly
            100                 105                 110

Gly Asn Lys Val Ile Glu Lys Val Leu Ile Ala Asn Asn Gly Ile Ala
            115                 120                 125

Ala Val Lys Cys Met Arg Ser Ile Arg Arg Trp Ser Tyr Glu Met Phe
            130                 135                 140

Arg Asn Glu Arg Ala Ile Arg Phe Val Val Met Val Thr Pro Glu Asp
145                 150                 155                 160

Leu Lys Ala Asn Ala Glu Tyr Ile Lys His Met Ala Asp His Tyr Val
                165                 170                 175

Pro Val Pro Gly Gly Ala Asn Asn Asn Tyr Ala Asn Val Glu Leu
            180                 185                 190

Ile Leu Asp Ile Ala Lys Arg Ile Pro Val Gln Ala Val Trp Ala Gly
            195                 200                 205

Trp Gly His Ala Ser Glu Asn Pro Lys Leu Pro Glu Leu Leu Leu Lys
            210                 215                 220

Asn Gly Ile Ala Phe Met Gly Pro Pro Ser Gln Ala Met Trp Ala Leu
225                 230                 235                 240

Gly Asp Lys Ile Ala Ser Ser Ile Val Ala Gln Thr Ala Gly Ile Pro
            245                 250                 255

Thr Leu Pro Trp Ser Gly Ser Gly Leu Arg Val Asp Trp Gln Glu Asn
            260                 265                 270

Asp Phe Ser Lys Arg Ile Leu Asn Val Pro Gln Asp Leu Tyr Glu Lys
            275                 280                 285

Gly Tyr Val Lys Asp Val Asp Asp Gly Leu Lys Ala Ala Glu Glu Val
            290                 295                 300

Gly Tyr Pro Val Met Ile Lys Ala Ser Glu Gly Gly Gly Lys Gly
305                 310                 315                 320

Ile Arg Lys Val Asn Asn Ala Asp Asp Phe Pro Asn Leu Phe Arg Gln
            325                 330                 335

Val Gln Ala Glu Val Pro Gly Ser Pro Ile Phe Val Met Arg Leu Ala
            340                 345                 350

Lys Gln Ser Arg His Leu Glu Val Gln Ile Leu Ala Asp Gln Tyr Gly
            355                 360                 365

Asn Ala Ile Ser Leu Phe Gly Arg Asp Cys Ser Val Gln Arg Arg His
            370                 375                 380

Gln Lys Ile Ile Glu Glu Ala Pro Ala Ile Ala Thr Pro Ala Val
385                 390                 395                 400

Phe Glu His Met Glu Gln Cys Ala Val Lys Leu Ala Lys Met Val Gly
            405                 410                 415

Tyr Val Ser Ala Gly Thr Val Glu Tyr Leu Tyr Ser Gln Asp Gly Ser
            420                 425                 430

Phe Tyr Phe Leu Glu Leu Asn Pro Arg Leu Gln Val Glu His Pro Cys
            435                 440                 445

Thr Glu Met Val Ala Asp Val Asn Leu Pro Ala Ala Gln Leu Gln Ile
            450                 455                 460

Ala Met Gly Ile Pro Leu Phe Arg Ile Lys Asp Ile Arg Met Met Tyr
465                 470                 475                 480

Gly Val Ser Pro Trp Gly Asp Ala Pro Ile Asp Phe Glu Asn Ser Ala
            485                 490                 495
```

His Val Pro Cys Pro Arg Gly His Val Ile Ala Ala Arg Ile Thr Ser
            500                 505                 510

Glu Asn Pro Asp Glu Gly Lys Pro Ser Ser Gly Thr Val Gln Glu
        515                 520                 525

Leu Asn Phe Arg Ser Asn Lys Asn Val Trp Gly Tyr Phe Ser Val Ala
    530                 535                 540

Ala Ala Gly Gly Leu His Glu Phe Ala Asp Ser Gln Phe Gly His Cys
545                 550                 555                 560

Phe Ser Trp Gly Glu Asn Arg Glu Ala Ile Ser Asn Met Val Val
                565                 570                 575

Ala Leu Lys Glu Leu Ser Ile Arg Gly Asp Phe Arg Thr Thr Val Glu
        580                 585                 590

Tyr Leu Ile Lys Leu Leu Glu Thr Glu Ser Phe Gln Leu Asn Arg Ile
    595                 600                 605

Asp Thr Gly Trp Leu Asp Arg Leu Ile Ala Glu Lys Val Gln Ala Glu
610                 615                 620

Arg Pro Asp Thr Met Leu Gly Val Val Cys Gly Ala Leu His Val Ala
625                 630                 635                 640

Asp Val Asn Leu Arg Asn Ser Ile Ser Asn Phe Leu His Ser Leu Glu
                645                 650                 655

Arg Gly Gln Val Leu Pro Ala His Thr Leu Leu Asn Thr Val Asp Glu
            660                 665                 670

Leu Ile Tyr Glu Gly Ile Lys Tyr Val Leu Lys Val Thr Arg Gln Ser
    675                 680                 685

Pro Asn Ser Tyr Val Val Ile Met Asn Gly Ser Cys Val Glu Val Asp
    690                 695                 700

Val His Arg Leu Ser Asp Gly Gly Leu Leu Leu Ser Tyr Asp Gly Ser
705                 710                 715                 720

Ser Tyr Thr Thr Tyr Met Lys Glu Glu Val Asp Arg Tyr Arg Ile Thr
                725                 730                 735

Ile Gly Asn Lys Thr Cys Val Phe Glu Lys Glu Asn Asp Pro Ser Val
            740                 745                 750

Met Arg Ser Pro Ser Ala Gly Lys Leu Ile Gln Tyr Ile Val Glu Asp
        755                 760                 765

Gly Gly His Val Phe Ala Gly Gln Cys Tyr Ala Glu Ile Glu Val Met
770                 775                 780

Lys Met Val Met Thr Leu Thr Ala Val Glu Ser Gly Cys Ile His Tyr
785                 790                 795                 800

Val Lys Arg Pro Gly Ala Ala Leu Asp Pro Gly Cys Val Ile Ala Lys
                805                 810                 815

Met Gln Leu Asp Asn Pro Ser Lys Val Gln Gln Ala Glu Leu His Thr
            820                 825                 830

Gly Ser Leu Pro Gln Ile Gln Ser Thr Ala Leu Arg Gly Glu Lys Leu
        835                 840                 845

His Arg Ile Phe
    850

<210> SEQ ID NO 119
<211> LENGTH: 853
<212> TYPE: PRT
<213> ORGANISM: Artificial Sequence
<220> FEATURE:
<223> OTHER INFORMATION: Description of Artificial Sequence: Synthetic
      Peptide -continued

```
<400> SEQUENCE: 119

Met Glu Glu Ser Ser Gln Pro Ala Lys Pro Leu Glu Met Asn Pro His
  1               5                  10                  15

Ser Arg Phe Ile Ile Gly Ser Val Ser Glu Asp Asn Ser Glu Asp Glu
             20                  25                  30

Thr Ser Ser Leu Val Lys Leu Asp Leu Leu Glu Glu Lys Glu Arg Ser
         35                  40                  45

Leu Ser Pro Val Ser Val Cys Ser Asp Ser Leu Ser Asp Leu Gly Leu
     50                  55                  60

Pro Ser Ala Gln Asp Gly Leu Ala Asn His Met Arg Pro Ser Met Ser
 65                  70                  75                  80

Gly Leu His Leu Val Lys Gln Gly Arg Asp Arg Lys Lys Val Asp Val
                 85                  90                  95

Gln Arg Asp Phe Thr Val Ala Ser Pro Ala Glu Phe Val Thr Arg Phe
            100                 105                 110

Gly Gly Asn Arg Val Ile Glu Lys Val Leu Ile Ala Asn Asn Gly Ile
        115                 120                 125

Ala Ala Val Lys Cys Met Arg Ser Ile Arg Arg Trp Ser Tyr Glu Met
    130                 135                 140

Phe Arg Asn Glu Arg Ala Ile Arg Phe Val Val Met Val Thr Pro Glu
145                 150                 155                 160

Asp Leu Lys Ala Asn Ala Glu Tyr Ile Lys Met Ala Asp His Tyr Val
                165                 170                 175

Pro Val Pro Gly Gly Pro Asn Asn Asn Tyr Ala Asn Val Glu Leu
            180                 185                 190

Ile Leu Asp Ile Ala Lys Arg Ile Pro Val Gln Ala Val Trp Ala Gly
        195                 200                 205

Trp Gly His Ala Ser Glu Asn Pro Lys Leu Pro Glu Leu Leu His Lys
    210                 215                 220

Asn Gly Ile Ala Phe Met Gly Pro Pro Ser Gln Ala Met Trp Ala Leu
225                 230                 235                 240

Gly Asp Lys Ile Ala Ser Ser Ile Val Ala Gln Thr Ala Gly Ile Pro
                245                 250                 255

Thr Leu Pro Trp Asn Gly Ser Gly Leu Arg Val Asp Trp Gln Glu Asn
            260                 265                 270

Asp Leu Gln Lys Arg Ile Leu Asn Val Pro Gln Glu Leu Tyr Glu Lys
        275                 280                 285

Gly Tyr Val Lys Asp Ala Asp Asp Gly Leu Arg Ala Ala Glu Glu Val
    290                 295                 300

Gly Tyr Pro Val Met Ile Lys Ala Ser Glu Gly Gly Gly Gly Lys Gly
305                 310                 315                 320

Ile Arg Lys Val Asn Asn Ala Asp Asp Phe Pro Asn Leu Phe Arg Gln
                325                 330                 335

Val Gln Ala Glu Val Pro Gly Ser Pro Ile Phe Val Met Arg Leu Ala
            340                 345                 350

Lys Gln Ser Arg His Leu Glu Val Gln Ile Leu Ala Asp Gln Tyr Gly
        355                 360                 365

Asn Ala Ile Ser Leu Phe Gly Arg Asp Cys Ser Val Gln Arg Arg His
    370                 375                 380

Gln Lys Ile Ile Glu Glu Ala Pro Ala Ser Ile Ala Thr Ser Val Val
385                 390                 395                 400

Phe Glu His Met Glu Gln Cys Ala Val Lys Leu Ala Lys Met Val Gly
                405                 410                 415
```

-continued

```
Tyr Val Ser Ala Gly Thr Val Glu Tyr Leu Tyr Ser Gln Asp Gly Ser
            420                 425                 430

Phe Tyr Phe Leu Glu Leu Asn Pro Arg Leu Gln Val Glu His Pro Cys
        435                 440                 445

Thr Glu Met Val Ala Asp Val Asn Leu Pro Ala Ala Gln Leu Gln Ile
    450                 455                 460

Ala Met Gly Ile Pro Leu His Arg Ile Lys Asp Ile Arg Val Met Tyr
465                 470                 475                 480

Gly Val Ser Pro Trp Gly Asp Gly Ser Ile Asp Phe Glu Asn Ser Ala
                485                 490                 495

His Val Pro Cys Pro Arg Gly His Val Ile Ala Ala Arg Ile Thr Ser
            500                 505                 510

Glu Asn Pro Asp Glu Gly Phe Lys Pro Ser Ser Gly Thr Val Gln Glu
        515                 520                 525

Leu Asn Phe Arg Ser Asn Lys Asn Val Trp Gly Tyr Phe Ser Val Ala
    530                 535                 540

Ala Ala Gly Gly Leu His Glu Phe Ala Asp Ser Gln Phe Gly His Cys
545                 550                 555                 560

Phe Ser Trp Gly Glu Asn Arg Glu Glu Ala Ile Ser Asn Met Val Val
                565                 570                 575

Ala Leu Lys Glu Leu Ser Ile Arg Gly Asp Phe Arg Thr Thr Val Glu
            580                 585                 590

Tyr Leu Ile Lys Leu Leu Glu Thr Glu Ser Phe Gln Gln Asn Arg Ile
        595                 600                 605

Asp Thr Gly Trp Leu Asp Arg Leu Ile Ala Glu Lys Val Gln Ala Glu
    610                 615                 620

Arg Pro Asp Thr Met Leu Gly Val Val Cys Gly Ala Leu His Val Ala
625                 630                 635                 640

Asp Val Ser Phe Arg Asn Ser Val Ser Asn Phe Leu His Ser Leu Glu
                645                 650                 655

Arg Gly Gln Val Leu Pro Ala His Thr Leu Leu Asn Thr Val Asp Val
            660                 665                 670

Glu Leu Ile Tyr Glu Gly Arg Lys Tyr Val Leu Lys Val Thr Arg Gln
        675                 680                 685

Ser Pro Asn Ser Tyr Val Val Ile Met Asn Ser Ser Cys Val Glu Val
    690                 695                 700

Asp Val His Arg Leu Ser Asp Gly Gly Leu Leu Leu Ser Tyr Asp Gly
705                 710                 715                 720

Ser Ser Tyr Thr Thr Tyr Met Lys Glu Glu Val Asp Arg Tyr Arg Ile
                725                 730                 735

Thr Ile Gly Asn Lys Thr Cys Val Phe Glu Lys Glu Asn Asp Pro Ser
            740                 745                 750

Ile Leu Arg Ser Pro Ser Ala Gly Lys Leu Ile Gln Tyr Val Val Glu
        755                 760                 765

Asp Gly Gly His Val Phe Ala Gly Gln Cys Phe Ala Glu Ile Glu Val
    770                 775                 780

Met Lys Met Val Met Thr Leu Thr Ala Gly Glu Ser Gly Cys Ile His
785                 790                 795                 800

Tyr Val Lys Arg Pro Gly Ala Val Leu Asp Pro Gly Cys Val Ile Ala
                805                 810                 815

Lys Leu Gln Leu Asp Asp Pro Ser Arg Val Gln Gln Ala Glu Leu His
            820                 825                 830
```

Thr Gly Thr Leu Pro Gln Ile Gln Ser Thr Ala Leu Arg Gly Glu Lys
        835                 840                 845

Leu His Arg Ile Phe
    850

<210> SEQ ID NO 120
<211> LENGTH: 802
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 120

Met Ser Glu Glu Ser Leu Phe Glu Ser Pro Gln Lys Met Glu Tyr
 1               5                  10                  15

Glu Ile Thr Asn Tyr Ser Glu Arg His Thr Glu Leu Pro Gly His Phe
                 20                  25                  30

Ile Gly Leu Asn Thr Val Asp Lys Leu Glu Ser Pro Leu Arg Asp
         35                  40                  45

Phe Val Lys Ser His Gly Gly His Thr Val Ile Ser Lys Ile Leu Ile
     50                  55                  60

Ala Asn Asn Gly Ile Ala Ala Val Lys Glu Ile Arg Ser Val Arg Lys
 65                  70                  75                  80

Trp Ala Tyr Glu Thr Phe Gly Asp Asp Arg Thr Val Gln Phe Val Ala
                 85                  90                  95

Met Ala Thr Pro Glu Asp Leu Glu Ala Asn Ala Glu Tyr Ile Arg Met
                100                 105                 110

Ala Asp Gln Tyr Ile Glu Val Pro Gly Gly Thr Asn Asn Asn Asn Tyr
            115                 120                 125

Ala Asn Val Asp Leu Ile Val Asp Ile Ala Glu Arg Ala Asp Val Asp
        130                 135                 140

Ala Val Trp Ala Gly Trp Gly His Ala Ser Glu Asn Pro Leu Leu Pro
145                 150                 155                 160

Glu Lys Leu Ser Gln Ser Lys Arg Lys Val Ile Phe Ile Gly Pro Pro
                165                 170                 175

Gly Asn Ala Met Arg Ser Leu Gly Asp Lys Ile Ser Ser Thr Ile Val
                180                 185                 190

Ala Gln Ser Ala Lys Val Pro Cys Ile Pro Trp Ser Gly Thr Gly Val
            195                 200                 205

Asp Thr Val His Val Asp Glu Lys Thr Gly Leu Val Ser Val Asp Asp
        210                 215                 220

Asp Ile Tyr Gln Lys Gly Cys Cys Thr Ser Pro Glu Asp Gly Leu Gln
225                 230                 235                 240

Lys Ala Lys Arg Ile Gly Phe Pro Val Met Ile Lys Ala Ser Glu Gly
                245                 250                 255

Gly Gly Gly Lys Gly Ile Arg Gln Val Glu Arg Glu Glu Asp Phe Ile
                260                 265                 270

Ala Leu Tyr His Gln Ala Ala Asn Glu Ile Pro Gly Ser Pro Ile Phe
            275                 280                 285

Ile Met Lys Leu Ala Gly Arg Ala Arg His Leu Glu Val Gln Leu Leu
        290                 295                 300

Ala Asp Gln Tyr Gly Thr Asn Ile Ser Leu Phe Gly Arg Asp Cys Ser
305                 310                 315                 320

Val Gln Arg Arg His Gln Lys Ile Ile Glu Glu Ala Pro Val Thr Ile
                325                 330                 335

-continued

```
Ala Lys Ala Glu Thr Phe His Glu Met Glu Lys Ala Ala Val Arg Leu
            340                 345                 350

Gly Lys Leu Val Gly Tyr Val Ser Ala Gly Thr Val Glu Tyr Leu Tyr
            355                 360                 365

Ser His Asp Asp Gly Lys Phe Tyr Phe Leu Glu Leu Asn Pro Arg Leu
            370                 375                 380

Gln Val Glu His Pro Thr Thr Glu Met Val Ser Gly Val Asn Leu Pro
385                 390                 395                 400

Ala Ala Gln Leu Gln Ile Ala Met Gly Ile Pro Met His Arg Ile Ser
            405                 410                 415

Asp Ile Arg Thr Leu Tyr Gly Met Asn Pro His Ser Ala Ser Glu Ile
            420                 425                 430

Asp Phe Glu Phe Lys Thr Gln Asp Ala Thr Lys Lys Gln Arg Arg Pro
            435                 440                 445

Ile Pro Lys Gly His Cys Thr Ala Cys Arg Ile Thr Ser Glu Asp Pro
            450                 455                 460

Asn Asp Gly Phe Lys Pro Ser Gly Gly Thr Leu His Glu Leu Asn Phe
465                 470                 475                 480

Arg Ser Ser Asn Val Trp Gly Tyr Phe Ser Val Gly Asn Asn Gly
            485                 490                 495

Asn Ile His Ser Phe Ser Asp Ser Gln Phe Gly His Ile Phe Ala Phe
            500                 505                 510

Gly Glu Asn Arg Gln Ala Ser Arg Lys His Met Val Val Ala Leu Lys
            515                 520                 525

Glu Leu Ser Ile Arg Gly Asp Phe Arg Thr Thr Val Glu Tyr Leu Ile
            530                 535                 540

Lys Leu Leu Glu Thr Glu Asp Phe Glu Asp Asn Thr Ile Thr Thr Gly
545                 550                 555                 560

Trp Leu Asp Asp Leu Ile Thr His Lys Met Thr Ala Glu Lys Pro Asp
            565                 570                 575

Pro Thr Leu Ala Val Ile Cys Gly Ala Ala Thr Lys Ala Phe Leu Ala
            580                 585                 590

Ser Glu Glu Ala Arg His Lys Tyr Ile Glu Ser Leu Gln Lys Gly Gln
            595                 600                 605

Val Leu Ser Lys Asp Leu Leu Gln Thr Met Phe Pro Val Asp Phe Ile
610                 615                 620

His Glu Gly Lys Arg Tyr Lys Phe Thr Val Ala Lys Ser Gly Asn Asp
625                 630                 635                 640

Arg Tyr Thr Leu Phe Ile Asn Gly Ser Lys Cys Asp Ile Ile Leu Arg
            645                 650                 655

Gln Leu Ser Asp Gly Gly Leu Leu Ile Ala Ile Gly Gly Lys Ser His
            660                 665                 670

Thr Ile Tyr Trp Lys Glu Val Ala Ala Thr Arg Leu Ser Val Asp
            675                 680                 685

Ser Met Thr Thr Leu Leu Glu Val Glu Asn Asp Pro Thr Gln Leu Arg
            690                 695                 700

Thr Pro Ser Pro Gly Lys Leu Val Lys Phe Leu Val Glu Asn Gly Glu
705                 710                 715                 720

His Ile Ile Lys Gly Gln Pro Tyr Ala Glu Ile Glu Val Met Lys Met
            725                 730                 735

Gln Met Pro Leu Val Ser Gln Glu Asn Gly Ile Val Gln Leu Leu Lys
            740                 745                 750
```

```
Gln Pro Gly Ser Thr Ile Val Ala Gly Asp Ile Met Ala Ile Met Thr
            755                 760                 765

Leu Asp Asp Pro Ser Lys Val Lys His Ala Leu Pro Phe Glu Gly Met
    770                 775                 780

Leu Pro Asp Phe Gly Ser Pro Val Ile Glu Gly Thr Lys Pro Ala Tyr
785                 790                 795                 800

Lys Phe

<210> SEQ ID NO 121
<211> LENGTH: 453
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 121

Met Arg Phe Asn Lys Ile Leu Ile Ala Asn Arg Gly Glu Ile Ala Leu
  1               5                  10                  15

Arg Ile Leu Arg Thr Cys Glu Glu Leu Gly Ile Gly Thr Ile Ala Val
             20                  25                  30

His Ser Thr Val Asp Arg Asn Ala Leu His Val Gln Leu Ala Asp Glu
         35                  40                  45

Ala Val Cys Ile Gly Glu Ala Ala Ser Ser Lys Ser Tyr Leu Asn Ile
     50                  55                  60

Pro Asn Ile Ile Ala Ala Ala Leu Thr Arg Asn Ala Ser Ala Ile His
 65                  70                  75                  80

Pro Gly Tyr Gly Phe Leu Ala Glu Asn Ala Arg Phe Ala Glu Ile Cys
                 85                  90                  95

Ala Asp His His Leu Thr Phe Ile Gly Pro Ser Pro Asp Ser Ile Arg
            100                 105                 110

Ala Met Gly Asp Lys Ser Thr Ala Lys Glu Thr Met Gln Arg Val Gly
        115                 120                 125

Val Pro Thr Ile Pro Gly Ser Asp Gly Leu Leu Thr Asp Val Asp Ser
    130                 135                 140

Ala Ala Lys Val Ala Ala Glu Ile Gly Tyr Pro Val Met Ile Lys Ala
145                 150                 155                 160

Thr Ala Gly Gly Gly Gly Arg Gly Met Arg Leu Val Arg Glu Pro Ala
                165                 170                 175

Asp Leu Glu Lys Leu Phe Leu Ala Ala Gln Gly Glu Ala Glu Ala Ala
            180                 185                 190

Phe Gly Asn Pro Gly Leu Tyr Leu Glu Lys Phe Ile Asp Arg Pro Arg
        195                 200                 205

His Val Glu Gly Gln Ile Leu Ala Asp Ala Tyr Gly Asn Val Val His
    210                 215                 220

Leu Gly Glu Arg Asp Cys Ser Ile Gln Arg Arg His Gln Lys Leu Leu
225                 230                 235                 240

Glu Glu Ala Pro Ser Pro Ala Leu Ser Ala Asp Leu Arg Gln Lys Met
                245                 250                 255

Gly Asp Ala Ala Val Lys Val Ala Gln Ala Ile Gly Tyr Ile Gly Ala
            260                 265                 270

Gly Thr Val Glu Phe Leu Val Asp Ala Thr Gly Asn Phe Tyr Phe Met
        275                 280                 285

Glu Met Asn Thr Arg Ile Gln Val Glu His Pro Val Thr Glu Met Ile
    290                 295                 300
```

```
Thr Gly Leu Asp Leu Ile Ala Glu Gln Ile Arg Ile Ala Gln Gly Glu
305                 310                 315                 320

Ala Leu Arg Phe Arg Gln Ala Asp Ile Gln Leu Arg Gly His Ala Ile
                325                 330                 335

Glu Cys Arg Ile Asn Ala Glu Asp Pro Glu Tyr Asn Phe Arg Pro Asn
                340                 345                 350

Pro Gly Arg Ile Thr Gly Tyr Leu Pro Pro Gly Pro Gly Val Arg
                355                 360                 365

Val Asp Ser His Val Tyr Thr Asp Tyr Glu Ile Pro Pro Tyr Tyr Asp
370                 375                 380

Ser Leu Ile Gly Lys Leu Ile Val Trp Gly Ala Thr Arg Glu Glu Ala
385                 390                 395                 400

Ile Ala Arg Met Gln Arg Ala Leu Arg Glu Cys Ala Ile Thr Gly Leu
                405                 410                 415

Pro Thr Thr Leu Ser Phe His Gln Leu Met Leu Gln Met Pro Glu Phe
                420                 425                 430

Leu Arg Gly Glu Leu Tyr Thr Asn Phe Val Glu Gln Val Met Leu Pro
                435                 440                 445

Arg Ile Leu Lys Ser
450

<210> SEQ ID NO 122
<211> LENGTH: 593
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 122

Met Lys Phe Asp Lys Ile Leu Ile Ala Asn Arg Gly Glu Ile Ala Leu
1               5                   10                  15

Arg Ile Leu Arg Ala Cys Glu Glu Met Gly Ile Ala Thr Ile Ala Val
                20                  25                  30

His Ser Thr Val Asp Arg Asn Ala Leu His Val Gln Leu Ala Asp Glu
                35                  40                  45

Ala Val Cys Ile Gly Glu Pro Ala Ser Ala Lys Ser Tyr Leu Asn Ile
50                  55                  60

Pro Asn Ile Ile Ala Ala Leu Thr Arg Asn Ala Ser Ala Ile His
65                  70                  75                  80

Pro Gly Tyr Gly Phe Leu Ser Glu Asn Ala Lys Phe Ala Glu Ile Cys
                85                  90                  95

Ala Asp His His Ile Ala Phe Ile Gly Pro Thr Pro Glu Ala Ile Arg
                100                 105                 110

Leu Met Gly Asp Lys Ser Thr Ala Lys Glu Thr Met Gln Lys Ala Gly
                115                 120                 125

Val Pro Thr Val Pro Gly Ser Glu Gly Leu Val Glu Thr Glu Gln Glu
130                 135                 140

Gly Leu Glu Leu Ala Lys Asp Ile Gly Tyr Pro Val Met Ile Lys Ala
145                 150                 155                 160

Thr Ala Gly Gly Gly Gly Arg Gly Met Arg Leu Val Arg Ser Pro Asp
                165                 170                 175

Glu Phe Val Lys Leu Phe Leu Ala Ala Gln Gly Glu Ala Gly Ala Ala
                180                 185                 190

Phe Gly Asn Ala Gly Val Tyr Ile Glu Lys Phe Ile Glu Arg Pro Arg
                195                 200                 205
```

```
His Ile Glu Phe Gln Ile Leu Ala Asp Asn Tyr Gly Asn Val Ile His
            210                 215                 220

Leu Gly Glu Arg Asp Cys Ser Ile Gln Arg Arg Asn Gln Lys Leu Leu
225                 230                 235                 240

Glu Glu Ala Pro Ser Pro Ala Leu Asp Ser Asp Leu Arg Glu Lys Met
                245                 250                 255

Gly Gln Ala Ala Val Lys Ala Ala Gln Phe Ile Asn Tyr Ala Gly Ala
            260                 265                 270

Gly Thr Ile Glu Phe Leu Leu Asp Arg Ser Gly Gln Phe Tyr Phe Met
            275                 280                 285

Glu Met Asn Thr Arg Ile Gln Val Glu His Pro Val Thr Glu Met Val
290                 295                 300

Thr Gly Val Asp Leu Leu Val Glu Gln Ile Arg Ile Ala Gln Gly Glu
305                 310                 315                 320

Arg Leu Arg Leu Thr Gln Asp Gln Val Val Leu Arg Gly His Ala Ile
                325                 330                 335

Glu Cys Arg Ile Asn Ala Glu Asp Pro Asp His Asp Phe Arg Pro Ala
                340                 345                 350

Pro Gly Arg Ile Ser Gly Tyr Leu Pro Pro Gly Gly Pro Gly Val Arg
            355                 360                 365

Ile Asp Ser His Val Tyr Thr Asp Tyr Gln Ile Pro Pro Tyr Tyr Asp
370                 375                 380

Ser Leu Ile Gly Lys Leu Ile Val Trp Gly Pro Asp Arg Ala Thr Ala
385                 390                 395                 400

Ile Asn Arg Met Lys Arg Ala Leu Arg Glu Cys Ala Ile Thr Gly Leu
                405                 410                 415

Pro Thr Thr Ile Gly Phe His Gln Arg Ile Met Glu Asn Pro Gln Phe
            420                 425                 430

Leu Gln Gly Asn Val Ser Thr Ser Phe Val Gln Glu Met Asn Lys Pro
            435                 440                 445

Leu Asp Phe Asn Glu Ile Arg Gln Leu Leu Thr Thr Ile Ala Gln Thr
450                 455                 460

Asp Ile Ala Glu Val Thr Leu Lys Ser Asp Asp Phe Glu Leu Thr Val
465                 470                 475                 480

Arg Lys Ala Val Gly Val Asn Asn Ser Val Pro Val Val Thr Ala
                485                 490                 495

Pro Leu Ser Gly Val Val Gly Ser Gly Leu Pro Ser Ala Ile Pro Ile
            500                 505                 510

Val Ala His Ala Ala Pro Ser Pro Ser Pro Glu Pro Gly Thr Ser Arg
            515                 520                 525

Ala Ala Asp His Ala Val Thr Ser Ser Gly Ser Gln Pro Gly Ala Lys
530                 535                 540

Ile Ile Asp Gln Lys Leu Ala Glu Val Ala Ser Pro Met Val Gly Thr
545                 550                 555                 560

Phe Tyr Arg Ala Pro Ala Pro Gly Glu Ala Val Phe Val Glu Val Gly
                565                 570                 575

Asp Arg Ile Arg Gln Gly Gln Thr Val Cys Ile Ile Glu Ala Met Lys
                580                 585                 590

Met

<210> SEQ ID NO 123
<211> LENGTH: 605
<212> TYPE: PRT
<213> ORGANISM: Artificial Sequence
```

-continued

```
<220> FEATURE:
<223> OTHER INFORMATION: Description of Artificial Sequence:  Synthetic
      Peptide

<400> SEQUENCE: 123

Met Leu Asp Lys Ile Val Ile Ala Asn Arg Gly Glu Ile Ala Leu Arg
 1               5                  10                  15

Ile Leu Arg Ala Cys Lys Glu Leu Gly Ile Lys Thr Val Ala Val His
             20                  25                  30

Ser Ser Ala Asp Arg Asp Leu Lys His Val Leu Leu Ala Asp Glu Thr
         35                  40                  45

Val Cys Ile Gly Pro Ala Pro Ser Val Lys Ser Tyr Leu Asn Ile Pro
     50                  55                  60

Ala Ile Ile Ser Ala Ala Glu Ile Thr Gly Ala Val Ala Ile His Pro
 65                  70                  75                  80

Gly Tyr Gly Phe Leu Ser Glu Asn Ala Asn Phe Ala Glu Gln Val Glu
                 85                  90                  95

Arg Ser Gly Phe Ile Phe Ile Gly Pro Lys Ala Glu Thr Ile Arg Leu
            100                 105                 110

Met Gly Asp Lys Val Ser Ala Ile Ala Ala Met Lys Lys Ala Gly Val
        115                 120                 125

Pro Cys Val Pro Gly Ser Asp Gly Pro Leu Gly Asp Asp Met Asp Lys
    130                 135                 140

Asn Arg Ala Ile Ala Lys Arg Ile Gly Tyr Pro Val Ile Ile Lys Ala
145                 150                 155                 160

Ser Gly Gly Gly Gly Arg Gly Met Arg Val Val Arg Gly Asp Ala
                165                 170                 175

Glu Leu Ala Gln Ser Ile Ser Met Thr Arg Ala Glu Ala Lys Ala Ala
                180                 185                 190

Phe Ser Asn Asp Met Val Tyr Met Glu Lys Tyr Leu Glu Asn Pro Arg
            195                 200                 205

His Val Glu Ile Gln Val Leu Ala Asp Gly Gln Gly Asn Ala Ile Tyr
        210                 215                 220

Leu Ala Glu Arg Asp Cys Ser Met Gln Arg Arg His Gln Lys Val Val
225                 230                 235                 240

Glu Glu Ala Pro Ala Pro Gly Ile Thr Pro Glu Leu Arg Arg Tyr Ile
                245                 250                 255

Gly Glu Arg Cys Ala Lys Ala Cys Val Asp Ile Gly Tyr Arg Gly Ala
            260                 265                 270

Gly Thr Phe Glu Phe Leu Phe Glu Asn Gly Glu Phe Tyr Phe Ile Glu
        275                 280                 285

Met Asn Thr Arg Ile Gln Val Glu His Pro Val Thr Glu Met Ile Thr
    290                 295                 300

Gly Val Asp Leu Ile Lys Glu Gln Met Arg Ile Ala Ala Gly Gln Pro
305                 310                 315                 320

Leu Ser Ile Lys Gln Glu Glu Val His Val Arg Gly His Ala Val Glu
                325                 330                 335

Cys Arg Ile Asn Ala Glu Asp Pro Asn Thr Phe Leu Pro Ser Pro Gly
            340                 345                 350

Lys Ile Thr Arg Phe His Ala Pro Gly Gly Phe Gly Val Arg Trp Glu
        355                 360                 365

Ser His Ile Tyr Ala Gly Tyr Thr Val Pro Pro Tyr Tyr Asp Ser Met
    370                 375                 380
```

-continued

```
Ile Gly Lys Leu Ile Cys Tyr Gly Glu Asn Arg Asp Val Ala Ile Ala
385                 390                 395                 400

Arg Met Lys Asn Ala Leu Gln Glu Leu Ile Ile Asp Gly Ile Lys Thr
                405                 410                 415

Asn Val Asp Leu Gln Ile Arg Ile Met Asn Asp Glu Asn Phe Gln His
            420                 425                 430

Gly Gly Thr Asn Ile His Tyr Leu Glu Lys Lys Leu Gly Leu Gln Glu
        435                 440                 445

Lys Met Asp Ile Arg Lys Ile Lys Lys Leu Ile Glu Leu Val Glu Glu
    450                 455                 460

Ser Gly Ile Ser Glu Leu Glu Ile Ser Glu Gly Glu Ser Val Arg
465                 470                 475                 480

Ile Ser Arg Ala Ala Pro Ala Ala Ser Phe Pro Val Met Gln Gln Ala
                485                 490                 495

Tyr Ala Ala Pro Met Met Gln Gln Pro Ala Gln Ser Asn Ala Ala Ala
            500                 505                 510

Pro Ala Thr Val Pro Ser Met Glu Ala Pro Ala Ala Ala Glu Ile Ser
        515                 520                 525

Gly His Ile Val Arg Ser Pro Met Val Gly Thr Phe Tyr Arg Thr Pro
    530                 535                 540

Ser Pro Asp Ala Lys Ala Phe Ile Glu Val Gly Gln Lys Val Asn Val
545                 550                 555                 560

Gly Asp Thr Leu Cys Ile Val Glu Ala Met Lys Met Asn Gln Ile
                565                 570                 575

Glu Ala Asp Lys Ser Gly Thr Val Lys Ala Ile Leu Val Glu Ser Gly
            580                 585                 590

Gln Pro Val Glu Phe Asp Glu Pro Leu Val Val Ile Glu
        595                 600                 605

<210> SEQ ID NO 124
<211> LENGTH: 703
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 124

Met Leu Ser Ala Ala Leu Arg Thr Leu Lys His Val Leu Tyr Tyr Ser
 1               5                  10                  15

Arg Gln Cys Leu Met Val Ser Arg Asn Leu Gly Ser Val Gly Tyr Asp
                20                  25                  30

Pro Asn Glu Lys Thr Phe Asp Lys Ile Leu Val Ala Asn Arg Gly Glu
            35                  40                  45

Ile Ala Cys Arg Val Ile Arg Thr Cys Lys Lys Met Gly Ile Lys Thr
     50                  55                  60

Val Ala Ile His Ser Asp Val Asp Ala Ser Ser Val His Val Lys Met
 65                  70                  75                  80

Ala Asp Glu Ala Val Cys Val Gly Pro Ala Pro Thr Ser Lys Ser Tyr
                85                  90                  95

Leu Asn Met Asp Ala Ile Met Glu Ala Ile Lys Lys Thr Arg Ala Gln
            100                 105                 110

Ala Val His Pro Gly Tyr Gly Phe Leu Ser Glu Asn Lys Glu Phe Ala
        115                 120                 125

Arg Cys Leu Ala Ala Glu Asp Val Phe Ile Gly Pro Asp Thr His
    130                 135                 140
```

-continued

```
Ala Ile Gln Ala Met Gly Asp Lys Ile Glu Ser Lys Leu Leu Ala Lys
145                 150                 155                 160

Lys Ala Glu Val Asn Thr Ile Pro Gly Phe Asp Gly Val Val Lys Asp
            165                 170                 175

Ala Glu Glu Ala Val Arg Ile Ala Arg Glu Ile Gly Tyr Pro Val Met
            180                 185                 190

Ile Lys Ala Ser Ala Gly Gly Gly Lys Gly Met Arg Ile Ala Trp
        195                 200                 205

Asp Asp Glu Glu Thr Arg Ile Asp Gly Phe Arg Leu Ser Ser Gln Glu
        210                 215                 220

Ala Ala Ser Ser Phe Gly Asp Asp Arg Leu Leu Ile Glu Lys Phe Ile
225                 230                 235                 240

Asp Asn Pro Arg His Ile Glu Thr Ile Gln Val Leu Gly Asp Lys His
            245                 250                 255

Gly Asn Ala Leu Trp Leu Asn Glu Arg Glu Cys Ser Ile Gln Arg Arg
        260                 265                 270

Asn Gln Lys Val Val Glu Glu Ala Pro Ser Ile Phe Leu Asp Ala Glu
        275                 280                 285

Thr Arg Arg Ala Met Gly Glu Gln Ala Val Ala Leu Ala Arg Ala Val
        290                 295                 300

Lys Tyr Ser Ser Ala Gly Thr Val Glu Phe Leu Val Asp Ser Lys Lys
305                 310                 315                 320

Asn Phe Tyr Phe Leu Glu Met Asn Thr Arg Leu Gln Val Glu His Pro
            325                 330                 335

Val Thr Glu Cys Ile His Trp Pro Gly Pro Ser Pro Gly Lys Thr Val
            340                 345                 350

Leu Gln Glu His Leu Ser Gly Thr Asn Lys Leu Ile Phe Ala Phe Asn
        355                 360                 365

Gly Trp Ala Val Glu Cys Arg Val Tyr Ala Glu Asp Pro Tyr Lys Ser
        370                 375                 380

Phe Gly Leu Pro Ser Ile Gly Arg Leu Ser Gln Tyr Gln Glu Pro Leu
385                 390                 395                 400

His Leu Pro Gly Val Arg Val Asp Ser Gly Ile Gln Pro Gly Ser Asp
            405                 410                 415

Ile Ser Ile Tyr Tyr Asp Pro Met Ile Ser Lys Leu Ile Thr Tyr Gly
            420                 425                 430

Ser Asp Arg Thr Glu Ala Leu Lys Arg Met Ala Asp Ala Leu Asp Asn
        435                 440                 445

Tyr Val Ile Arg Gly Val Thr His Asn Ile Ala Leu Leu Arg Glu Val
        450                 455                 460

Ile Ile Asn Ser Arg Phe Val Lys Gly Asp Ile Ser Thr Lys Phe Leu
465                 470                 475                 480

Ser Asp Val Tyr Pro Asp Gly Phe Lys Gly His Met Leu Thr Lys Ser
            485                 490                 495

Glu Lys Asn Gln Leu Leu Ala Ile Ser Ser Leu Phe Val Ala Phe Gln
        500                 505                 510

Leu Arg Ala Gln His Phe Gln Glu Asn Ser Arg Met Pro Val Ile Lys
        515                 520                 525

Pro Asp Ile Ala Asn Trp Glu Leu Ser Val Lys Leu His Asp Lys Val
530                 535                 540

His Thr Val Val Ala Ser Asn Asn Gly Ser Val Phe Ser Val Glu Val
545                 550                 555                 560
```

```
Asp Gly Ser Lys Leu Asn Val Thr Ser Thr Trp Asn Leu Ala Ser Pro
            565                 570                 575

Leu Leu Ser Val Ser Val Asp Gly Thr Gln Arg Thr Val Gln Cys Leu
            580                 585                 590

Ser Arg Glu Ala Gly Gly Asn Met Ser Ile Gln Phe Leu Gly Thr Val
            595                 600                 605

Tyr Lys Val Asn Ile Leu Thr Arg Leu Ala Ala Glu Leu Asn Lys Phe
            610                 615                 620

Met Leu Glu Lys Val Thr Glu Asp Thr Ser Ser Val Leu Arg Ser Pro
625                 630                 635                 640

Met Pro Gly Val Val Ala Val Ser Val Lys Pro Gly Asp Ala Val
            645                 650                 655

Ala Glu Gly Gln Glu Ile Cys Val Ile Glu Ala Met Lys Met Gln Asn
            660                 665                 670

Ser Met Thr Ala Gly Lys Thr Gly Thr Val Lys Ser Val His Cys Gln
            675                 680                 685

Ala Gly Asp Thr Val Gly Glu Gly Asp Leu Leu Val Glu Leu Glu
            690                 695                 700

<210> SEQ ID NO 125
<211> LENGTH: 722
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 125

Met Pro Tyr Arg Glu Arg Phe Cys Ala Ile Arg Trp Cys Arg Asn Ser
1               5                   10                  15

Gly Arg Ser Ser Gln Gln Leu Leu Trp Thr Leu Lys Arg Ala Pro Val
            20                  25                  30

Tyr Ser Gln Gln Cys Leu Val Val Ser Arg Ser Leu Ser Ser Val Glu
        35                  40                  45

Tyr Glu Pro Glu Lys Glu Lys Thr Phe Asp Lys Ile Leu Ile Ala Asn
    50                  55                  60

Arg Gly Glu Ile Ala Cys Arg Val Ile Lys Thr Cys Arg Lys Met Gly
65                  70                  75                  80

Ile Arg Thr Val Ala Ile His Ser Asp Val Asp Ala Ser Ser Val His
                85                  90                  95

Val Lys Met Ala Asp Glu Ala Val Cys Val Gly Pro Ala Pro Thr Ser
            100                 105                 110

Lys Ser Tyr Leu Asn Met Asp Ala Ile Met Glu Ala Ile Lys Lys Thr
        115                 120                 125

Gly Ala Gln Ala Val His Pro Gly Tyr Gly Phe Leu Ser Glu Asn Lys
    130                 135                 140

Glu Phe Ala Lys Cys Leu Ala Ala Glu Asp Val Thr Phe Ile Gly Pro
145                 150                 155                 160

Asp Thr His Ala Ile Gln Ala Met Gly Asp Lys Ile Glu Ser Lys Leu
                165                 170                 175

Leu Ala Lys Arg Ala Lys Val Asn Thr Ile Pro Gly Phe Asp Gly Val
            180                 185                 190

Leu Lys Asp Ala Asp Glu Ala Val Arg Ile Ala Arg Glu Ile Gly Tyr
        195                 200                 205

Pro Val Met Ile Lys Ala Ser Ala Gly Gly Gly Gly Lys Gly Met Arg
    210                 215                 220
```

-continued

```
Ile Pro Trp Asp Asp Glu Glu Thr Arg Asp Gly Phe Arg Phe Ser Ser
225                 230                 235                 240

Gln Glu Ala Ala Ser Ser Phe Gly Asp Asp Arg Leu Leu Ile Glu Lys
            245                 250                 255

Phe Ile Asp Asn Pro Arg His Ile Glu Ile Gln Val Leu Gly Asp Lys
        260                 265                 270

His Gly Asn Ala Leu Trp Leu Asn Glu Arg Glu Cys Ser Ile Gln Arg
    275                 280                 285

Arg Asn Gln Lys Val Val Glu Glu Ala Pro Ser Ile Phe Leu Asp Pro
290                 295                 300

Glu Thr Arg Arg Ala Met Gly Glu Gln Ala Val Ala Trp Pro Lys Ala
305                 310                 315                 320

Val Lys Tyr Ser Ser Ala Gly Thr Val Glu Phe Leu Val Asp Ser Gln
                325                 330                 335

Lys Asn Phe Tyr Phe Leu Glu Met Asn Thr Arg Leu Gln Val Glu His
            340                 345                 350

Pro Val Thr Glu Cys Ile Thr Gly Leu Asp Leu Val Gln Glu Met Ile
        355                 360                 365

Leu Val Ala Lys Gly Tyr Pro Leu Arg His Lys Gln Glu Asp Ile Pro
370                 375                 380

Ile Ser Gly Trp Ala Val Glu Cys Arg Val Tyr Ala Glu Asp Pro Tyr
385                 390                 395                 400

Lys Ser Phe Gly Leu Pro Ser Ile Gly Arg Leu Ser Gln Tyr Gln Glu
                405                 410                 415

Pro Ile His Leu Pro Gly Val Arg Val Asp Ser Gly Ile Gln Pro Gly
            420                 425                 430

Ser Asp Ile Ser Ile Tyr His Asp Pro Met Ile Ser Lys Leu Val Thr
        435                 440                 445

Tyr Gly Ser Asp Arg Ala Glu Ala Leu Lys Arg Met Glu Asp Ala Leu
    450                 455                 460

Asp Ser Tyr Val Ile Arg Gly Val Thr His Asn Ile Pro Leu Leu Arg
465                 470                 475                 480

Glu Val Ile Ile Asn Thr Arg Phe Val Lys Gly Asp Ile Ser Thr Lys
                485                 490                 495

Phe Leu Ser Asp Val Tyr Pro Asp Gly Phe Lys Gly His Met Leu Thr
            500                 505                 510

Pro Ser Glu Arg Asp Gln Leu Leu Ala Ile Ala Ser Ser Leu Phe Val
        515                 520                 525

Ala Ser Gln Leu Arg Ala Gln Arg Phe Gln Glu His Ser Arg Val Pro
    530                 535                 540

Val Ile Arg Pro Asp Val Ala Lys Trp Glu Leu Ser Val Lys Leu His
545                 550                 555                 560

Asp Glu Asp His Thr Val Ala Ser Asn Gly Pro Thr Phe Asn
                565                 570                 575

Val Glu Val Asp Gly Ser Lys Leu Asn Val Thr Ser Thr Trp Asn Leu
            580                 585                 590

Ala Ser Pro Leu Leu Ser Val Asn Val Asp Gly Thr Gln Arg Thr Val
        595                 600                 605

Gln Cys Leu Ser Pro Asp Ala Gly Gly Asn Met Ser Ile Gln Phe Leu
    610                 615                 620

Gly Thr Val Tyr Lys Val His Ile Leu Thr Lys Leu Ala Ala Glu Leu
625                 630                 635                 640
```

```
Asn Lys Phe Met Leu Glu Lys Val Pro Lys Asp Thr Ser Ser Val Leu
                645                 650                 655

Arg Ser Pro Lys Pro Gly Val Val Ala Val Ser Val Lys Pro Gly
            660                 665                 670

Asp Met Val Ala Glu Gly Gln Glu Ile Cys Val Ile Glu Ala Met Lys
                675                 680                 685

Met Gln Asn Ser Met Thr Ala Gly Lys Met Gly Lys Val Lys Leu Val
                690                 695                 700

His Cys Lys Ala Gly Asp Thr Val Gly Glu Gly Asp Leu Leu Val Glu
705                 710                 715                 720

Leu Glu

<210> SEQ ID NO 126
<211> LENGTH: 694
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 126

Met Ser Gln Arg Lys Phe Ala Gly Leu Arg Asp Asn Phe Asn Leu Leu
1               5                   10                  15

Gly Glu Lys Asn Lys Ile Leu Val Ala Asn Arg Gly Glu Ile Pro Ile
                20                  25                  30

Arg Ile Phe Arg Thr Ala His Glu Leu Ser Met Gln Thr Val Ala Ile
            35                  40                  45

Tyr Ser His Glu Asp Arg Leu Ser Thr His Lys Gln Lys Ala Asp Glu
    50                  55                  60

Ala Tyr Val Ile Gly Glu Val Gly Gln Tyr Thr Pro Val Gly Ala Tyr
65                  70                  75                  80

Leu Ala Ile Asp Glu Ile Ile Ser Ile Ala Gln Lys His Gln Val Asp
                85                  90                  95

Phe Ile His Pro Gly Tyr Gly Phe Leu Ser Glu Asn Ser Glu Phe Ala
            100                 105                 110

Asp Lys Val Val Lys Ala Gly Ile Thr Trp Ile Gly Pro Pro Ala Glu
        115                 120                 125

Val Ile Asp Ser Val Gly Asp Lys Val Ser Ala Arg Asn Leu Ala Ala
    130                 135                 140

Lys Ala Asn Val Pro Thr Val Pro Gly Thr Pro Gly Pro Ile Glu Thr
145                 150                 155                 160

Val Glu Glu Ala Leu Asp Phe Val Asn Glu Tyr Gly Tyr Pro Val Ile
                165                 170                 175

Ile Lys Ala Ala Phe Gly Gly Gly Arg Gly Met Arg Val Val Arg
            180                 185                 190

Glu Gly Asp Asp Val Ala Asp Ala Phe Gln Arg Ala Thr Ser Glu Ala
        195                 200                 205

Arg Thr Ala Gly Phe Asn Gly Thr Cys Phe Val Glu Arg Phe Leu Asp
    210                 215                 220

Lys Pro Lys His Ile Glu Val Gln Leu Leu Ala Asp Asn His Gly Asn
225                 230                 235                 240

Val Val His Leu Phe Glu Arg Asp Cys Ser Val Gln Arg Arg His Gln
                245                 250                 255

Lys Val Val Glu Val Ala Pro Ala Lys Thr Leu Pro Arg Glu Val Arg
            260                 265                 270
```

-continued

```
Asp Ala Ile Leu Thr Asp Ala Val Lys Leu Ala Lys Glu Cys Gly Tyr
        275                 280                 285

Arg Asn Ala Gly Thr Ala Glu Phe Leu Val Asp Asn Gln Asn Arg His
    290                 295                 300

Tyr Phe Ile Glu Ile Asn Pro Arg Ile Gln Val Glu His Thr Ile Thr
305                 310                 315                 320

Glu Glu Ile Thr Gly Ile Asp Ile Val Ala Ala Gln Ile Gln Ala Ala
                325                 330                 335

Gly Ala Ser Leu Pro Gln Leu Gly Leu Phe Gln Asp Lys Ile Thr Thr
                340                 345                 350

Arg Gly Phe Ala Ile Gln Cys Arg Ile Thr Thr Glu Asp Pro Ala Lys
            355                 360                 365

Asn Phe Gln Pro Asp Thr Gly Arg Ile Glu Val Tyr Arg Ser Ala Gly
370                 375                 380

Gly Asn Gly Val Arg Leu Asp Gly Gly Asn Ala Tyr Ala Gly Thr Ile
385                 390                 395                 400

Ile Ser Pro His Tyr Asp Ser Met Leu Val Lys Cys Ser Cys Ser Gly
                405                 410                 415

Ser Thr Tyr Glu Ile Val Arg Arg Lys Met Ile Arg Ala Leu Ile Glu
                420                 425                 430

Phe Arg Ile Arg Gly Val Lys Thr Asn Ile Pro Phe Leu Leu Thr Leu
            435                 440                 445

Leu Thr Asn Pro Val Phe Ile Glu Gly Thr Tyr Trp Gly Thr Phe Ile
450                 455                 460

Asp Asp Thr Pro Gln Leu Phe Gln Met Val Ser Ser Gln Asn Arg Ala
465                 470                 475                 480

Gln Lys Leu Leu His Tyr Leu Ala Asp Val Ala Asp Asn Gly Ser Ser
                485                 490                 495

Ile Lys Gly Gln Ile Gly Leu Pro Lys Leu Lys Ser Asn Pro Ser Val
                500                 505                 510

Pro His Ser Tyr Asn Met Tyr Pro Arg Val Tyr Glu Asp Phe Gln Lys
            515                 520                 525

Met Arg Glu Thr Tyr Gly Asp Leu Ser Val Leu Pro Thr Arg Ser Phe
530                 535                 540

Leu Ser Pro Leu Glu Thr Asp Glu Glu Ile Glu Val Val Ile Glu Gln
545                 550                 555                 560

Gly Lys Thr Leu Ile Ile Lys Leu Gln Ala Val Gly Asp Leu Asn Lys
                565                 570                 575

Lys Thr Gly Glu Arg Glu Val Tyr Phe Asp Leu Asn Gly Glu Met Arg
                580                 585                 590

Lys Ile Arg Val Ala Asp Arg Ser Gln Lys Val Glu Thr Val Thr Lys
            595                 600                 605

Ser Lys Ala Asp Met His Asp Pro Leu His Ile Gly Ala Pro Met Ala
610                 615                 620

Gly Val Ile Val Glu Val Lys Val His Lys Gly Ser Leu Ile Lys Lys
625                 630                 635                 640

Gly Gln Pro Val Ala Val Leu Ser Ala Met Lys Met Glu Met Ile Ile
                645                 650                 655

Ser Ser Pro Ser Asp Gly Gln Val Lys Glu Val Phe Val Ser Asp Gly
                660                 665                 670

Glu Asn Val Asp Ser Ser Asp Leu Leu Val Leu Leu Glu Asp Gln Val
            675                 680                 685
```

```
Pro Val Glu Thr Lys Ala
        690

<210> SEQ ID NO 127
<211> LENGTH: 170
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 127

Asn Ala Ile Asp Asp Val Leu Thr Val Ala Leu Phe Pro Gln Pro Gly
  1               5                  10                  15

Leu Lys Phe Leu Glu Asn Arg His Asn Pro Ala Ala Phe Glu Pro Val
             20                  25                  30

Pro Gln Ala Glu Ala Ala Gln Pro Val Ala Lys Ala Glu Lys Pro Ala
         35                  40                  45

Ala Ser Gly Val Tyr Thr Val Glu Val Glu Gly Lys Ala Phe Val Val
     50                  55                  60

Lys Val Ser Asp Gly Gly Asp Val Ser Gln Leu Thr Ala Ala Ala Pro
 65                  70                  75                  80

Ala Pro Ala Pro Ala Pro Ala Pro Ala Ser Ala Pro Ala Ala Ala Ala
                 85                  90                  95

Pro Ala Gly Ala Gly Thr Pro Val Thr Ala Pro Leu Ala Gly Thr Ile
            100                 105                 110

Trp Lys Val Leu Ala Ser Glu Gly Gln Thr Val Ala Ala Gly Glu Val
            115                 120                 125

Ile Leu Ile Leu Glu Ala Met Lys Met Glu Thr Glu Ile Arg Ala Ala
        130                 135                 140

Gln Ala Gly Thr Val Arg Gly Ile Ala Val Lys Ala Gly Asp Ala Val
145                 150                 155                 160

Ala Val Gly Asp Thr Leu Met Thr Leu Ala
                165                 170

<210> SEQ ID NO 128
<211> LENGTH: 123
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 128

Met Lys Leu Lys Val Thr Val Asn Gly Thr Ala Tyr Asp Val Asp Val
  1               5                  10                  15

Asp Val Asp Lys Ser His Glu Asn Pro Met Gly Thr Ile Leu Phe Gly
             20                  25                  30

Gly Gly Thr Gly Gly Ala Pro Ala Pro Arg Ala Ala Gly Ala Gly Ala
         35                  40                  45

Gly Lys Ala Gly Glu Gly Glu Ile Pro Ala Pro Leu Ala Gly Thr
     50                  55                  60

Val Ser Lys Ile Leu Val Lys Glu Gly Asp Thr Val Lys Ala Gly Gln
 65                  70                  75                  80

Thr Val Leu Val Leu Glu Ala Met Lys Met Glu Thr Glu Ile Asn Ala
                 85                  90                  95

Pro Thr Asp Gly Lys Val Glu Lys Val Leu Val Lys Glu Arg Asp Ala
            100                 105                 110
```

```
-continued
Val Gln Gly Gly Gln Gly Leu Ile His Ile Gly
    115                 120
```